US011603545B2

(12) United States Patent
Li et al.

(10) Patent No.: US 11,603,545 B2
(45) Date of Patent: Mar. 14, 2023

(54) RECOMBINANT YEAST STRAIN FOR PRODUCING NERVONIC ACIDS AND APPLICATION THEREOF

(71) Applicants: QINGDAO INSTITUTE OF BIOENERGY AND BIOPROCESS TECHNOLOGY, CHINESE ACADEMY OF SCIENCES, Shandong (CN); ZHEJIANG ZHENYUAN PHARMACEUTICAL CO., LTD., Zhejiang (CN)

(72) Inventors: Fuli Li, Shanghai (CN); Shian Wang, Shanghai (CN); Weiming Fan, Shanghai (CN); Huimin Meng, Shanghai (CN); Kai Zhang, Shanghai (CN); Jiaxin Li, Shanghai (CN)

(73) Assignees: ZHEJIANG ZHENYUAN BIOTECH CO. LTD., Shaoxing (CN); QINDAO INSTITUTE OF BIOENERGY AND BIOPROCESS TECHNOLOGY, CHINESE ACADEMY OF SCIENCES, Qingdao (CN)

( * ) Notice: Subject to any disclaimer, the term of this patent is extended or adjusted under 35 U.S.C. 154(b) by 65 days.

(21) Appl. No.: 17/046,672

(22) PCT Filed: Apr. 8, 2019

(86) PCT No.: PCT/CN2019/081736
§ 371 (c)(1),
(2) Date: Oct. 9, 2020

(87) PCT Pub. No.: WO2019/196791
PCT Pub. Date: Oct. 17, 2019

(65) Prior Publication Data

US 2021/0032665 A1 Feb. 4, 2021

(30) Foreign Application Priority Data

Apr. 9, 2018 (CN) ........................ 201810309632.4

(51) Int. Cl.

| | |
|---|---|
| ***C12P 7/6409*** | (2022.01) |
| ***C12N 1/16*** | (2006.01) |
| ***C12N 9/04*** | (2006.01) |
| ***C12N 9/02*** | (2006.01) |
| ***C12N 9/08*** | (2006.01) |
| ***C12N 9/10*** | (2006.01) |
| ***C12N 9/18*** | (2006.01) |

(52) U.S. Cl.
CPC .............. *C12P 7/6409* (2013.01); *C12N 1/16* (2013.01); *C12N 9/0006* (2013.01); *C12N 9/0008* (2013.01); *C12N 9/0051* (2013.01); *C12N 9/0065* (2013.01); *C12N 9/1029* (2013.01); *C12N 9/18* (2013.01); *C12Y 101/01049* (2013.01); *C12Y 102/01003* (2013.01); *C12Y 108/01007* (2013.01); *C12Y 111/01009* (2013.01); *C12Y 114/19001* (2013.01); *C12Y 203/0102* (2013.01); *C12Y 301/01004* (2013.01)

(58) Field of Classification Search
None
See application file for complete search history.

(56) References Cited

U.S. PATENT DOCUMENTS

2007/0087420 A1* 4/2007 MaCool ................ C12P 7/6463
435/254.2
2013/0143282 A1* 6/2013 Stephanopoulos .. C12N 9/0097
435/254.2

FOREIGN PATENT DOCUMENTS

WO WO2006/055322 5/2006
WO WO2017/070065 4/2017

OTHER PUBLICATIONS

Kizer et al. Appl Environ Microbiol. May 2008;74(10):3229-41. (Year: 2008).*
Prather et al. Curr Opin Biotechnol. Oct. 2008;19(5):468-74. (Year: 2008).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Fan Yong et al, Biosynthesis of nervonic acid and perspectives for its production by microalgae and other microorganisms Applied Microbiology and Biotechnology, vol. 102, No. 7, Feb. 24, 2018.

* cited by examiner

*Primary Examiner* — Christian L Fronda
(74) *Attorney, Agent, or Firm* — Adam Warwick Bell

(57) ABSTRACT

The present invention discloses an engineering yeast strain for producing nervonic acids. The yeast strain over-expresses the genes related to enzymes required in a synthetic process of long-chain unsaturated fatty acids, such as fatty acid elongase, desaturase, diacylglycerol acyltransferase and the like, and optionally, further adjusts and controls the synthesis and decomposition route of triglyceride, the synthesis and decomposition route of sphingomyelin, and the synthesis and decomposition route and the oxidation-reduction balanced route of lipid subcell levels. The recombinant yeast strain can produce microorganism oil; and the content of the prepared nervonic acids accounts for 39.6% of the total fatty acids.

20 Claims, 5 Drawing Sheets

Specification includes a Sequence Listing.

SEQUENCE LISTING

```
<160> NUMBER OF SEQ ID NOS: 127

<210> SEQ ID NO 1
<211> LENGTH: 44
<212> TYPE: DNA
<213> ORGANISM: artificial sequence
<220> FEATURE:
<223> OTHER INFORMATION: primer

<400> SEQUENCE: 1

actttttgca gtactaaccg cagactatcg actcacaata ctac                    44


<210> SEQ ID NO 2
<211> LENGTH: 41
<212> TYPE: DNA
<213> ORGANISM: artificial sequence
<220> FEATURE:
<223> OTHER INFORMATION: primer

<400> SEQUENCE: 2

gcaagaccgg caacgtgggg ttactcaatc attcggaact c                       41


<210> SEQ ID NO 3
<211> LENGTH: 43
<212> TYPE: DNA
<213> ORGANISM: artificial sequence
<220> FEATURE:
<223> OTHER INFORMATION: primer

<400> SEQUENCE: 3

catagcacgc gtgtagatac ctaagcagcc atgccagaca tac                     43


<210> SEQ ID NO 4
<211> LENGTH: 42
<212> TYPE: DNA
<213> ORGANISM: artificial sequence
<220> FEATURE:
```

-continued

<223> OTHER INFORMATION: primer

<400> SEQUENCE: 4
gaattaaaca cacatcaaca atggtgaaaa acgtggacca ag 42

<210> SEQ ID NO 5
<211> LENGTH: 45
<212> TYPE: DNA
<213> ORGANISM: artificial sequence
<220> FEATURE:
<223> OTHER INFORMATION: primer

<400> SEQUENCE: 5
actttttgca gtactaaccg cagatgagaa tctctctact ttgtg 45

<210> SEQ ID NO 6
<211> LENGTH: 40
<212> TYPE: DNA
<213> ORGANISM: artificial sequence
<220> FEATURE:
<223> OTHER INFORMATION: primer

<400> SEQUENCE: 6
gcaagaccgg caacgtgggg tcagttgtag cagtaattgc 40

<210> SEQ ID NO 7
<211> LENGTH: 44
<212> TYPE: DNA
<213> ORGANISM: artificial sequence
<220> FEATURE:
<223> OTHER INFORMATION: primer

<400> SEQUENCE: 7
actttttgca gtactaaccg cagatgcaat tacggttgat tttg 44

<210> SEQ ID NO 8
<211> LENGTH: 42
<212> TYPE: DNA
<213> ORGANISM: artificial sequence
<220> FEATURE:
<223> OTHER INFORMATION: primer

<400> SEQUENCE: 8
gcaagaccgg caacgtgggg ttagttaaaa cagtagcggt tg 42

<210> SEQ ID NO 9
<211> LENGTH: 45
<212> TYPE: DNA
<213> ORGANISM: artificial sequence
<220> FEATURE:
<223> OTHER INFORMATION: primer

<400> SEQUENCE: 9
actttttgca gtactaaccg cagatgaaat tctctccact tttgc 45

<210> SEQ ID NO 10
<211> LENGTH: 43
<212> TYPE: DNA
<213> ORGANISM: artificial sequence
<220> FEATURE:
<223> OTHER INFORMATION: primer

<400> SEQUENCE: 10
gcaagaccgg caacgtgggg ttacataaga agagcggcaa aac 43

-continued

<210> SEQ ID NO 11
<211> LENGTH: 45
<212> TYPE: DNA
<213> ORGANISM: artificial sequence
<220> FEATURE:
<223> OTHER INFORMATION: primer

<400> SEQUENCE: 11 acttttgca gtactaaccg cagatgaagt tctcggctac cattc 45

<210> SEQ ID NO 12
<211> LENGTH: 42
<212> TYPE: DNA
<213> ORGANISM: artificial sequence
<220> FEATURE:
<223> OTHER INFORMATION: primer

<400> SEQUENCE: 12
gcaagaccgg caacgtgggg ttagttgtaa cagtagtcgg ag 42

<210> SEQ ID NO 13
<211> LENGTH: 45
<212> TYPE: DNA
<213> ORGANISM: artificial sequence
<220> FEATURE:
<223> OTHER INFORMATION: primer

<400> SEQUENCE: 13 acttttgca gtactaaccg cagatcgcaa acttcctgct gcttc 45

<210> SEQ ID NO 14
<211> LENGTH: 48
<212> TYPE: DNA
<213> ORGANISM: artificial sequence
<220> FEATURE:
<223> OTHER INFORMATION: primer

<400> SEQUENCE: 14
gcaagaccgg caacgtgggg ttaaccagag tactgatagc agtattcc 48

<210> SEQ ID NO 15
<211> LENGTH: 44
<212> TYPE: DNA
<213> ORGANISM: artificial sequence
<220> FEATURE:
<223> OTHER INFORMATION: primer

<400> SEQUENCE: 15 acttttgca gtactaaccg cagatgcagt ttacgccctt attc 44

<210> SEQ ID NO 16
<211> LENGTH: 46
<212> TYPE: DNA
<213> ORGANISM: artificial sequence
<220> FEATURE:
<223> OTHER INFORMATION: primer

<400> SEQUENCE: 16
gcaagaccgg caacgtgggg tcatttactt gaatcaacac aatatc 46

<210> SEQ ID NO 17
<211> LENGTH: 40
<212> TYPE: DNA
<213> ORGANISM: artificial sequence
<220> FEATURE:
<223> OTHER INFORMATION: primer

<400> SEQUENCE: 17 acttttgca gtactaaccg caggcttcta tcccccatta 40

<210> SEQ ID NO 18
<211> LENGTH: 43
<212> TYPE: DNA
<213> ORGANISM: artificial sequence
<220> FEATURE:
<223> OTHER INFORMATION: primer

<400> SEQUENCE: 18
gcaagaccgg caacgtgggg ctatctcatg gtcaccagct cct 43

<210> SEQ ID NO 19
<211> LENGTH: 40
<212> TYPE: DNA
<213> ORGANISM: artificial sequence
<220> FEATURE:
<223> OTHER INFORMATION: primer

<400> SEQUENCE: 19 acttttgca gtactaaccg cagtccgccg agaaaaccaa 40

<210> SEQ ID NO 20
<211> LENGTH: 42
<212> TYPE: DNA
<213> ORGANISM: artificial sequence
<220> FEATURE:
<223> OTHER INFORMATION: primer

<400> SEQUENCE: 20
gcaagaccgg caacgtgggg ttagggcttt ttgaggaggg tc 42

<210> SEQ ID NO 21
<211> LENGTH: 40
<212> TYPE: DNA
<213> ORGANISM: artificial sequence
<220> FEATURE:
<223> OTHER INFORMATION: primer

<400> SEQUENCE: 21
gaattaaaca cacatcaaca atggagtctg gacctatgcc 40

<210> SEQ ID NO 22
<211> LENGTH: 41
<212> TYPE: DNA
<213> ORGANISM: artificial sequence
<220> FEATURE:
<223> OTHER INFORMATION: primer

<400> SEQUENCE: 22
catagcacgc gtgtagatac ctactgggcc tttttttgag c 41

<210> SEQ ID NO 23
<211> LENGTH: 41
<212> TYPE: DNA
<213> ORGANISM: artificial sequence
<220> FEATURE:
<223> OTHER INFORMATION: primer

<400> SEQUENCE: 23
catagcacgc gtgtagatac ttaagatcgg ccgttctgca c 41

<210> SEQ ID NO 24
<211> LENGTH: 41

-continued

<212> TYPE: DNA
<213> ORGANISM: artificial sequence
<220> FEATURE:
<223> OTHER INFORMATION: primer

<400> SEQUENCE: 24
gaattaaaca cacatcaaca atgacctctg tgaacgtgaa g 41

<210> SEQ ID NO 25
<211> LENGTH: 44
<212> TYPE: DNA
<213> ORGANISM: artificial sequence
<220> FEATURE:
<223> OTHER INFORMATION: primer

<400> SEQUENCE: 25
actttttgca gtactaaccg cagacctctg tgaacgtgaa gctg 44

<210> SEQ ID NO 26
<211> LENGTH: 41
<212> TYPE: DNA
<213> ORGANISM: artificial sequence
<220> FEATURE:
<223> OTHER INFORMATION: primer

<400> SEQUENCE: 26
gcaagaccgg caacgtgggg ttaagatcgg ccgttctgca c 41

<210> SEQ ID NO 27
<211> LENGTH: 44
<212> TYPE: DNA
<213> ORGANISM: artificial sequence
<220> FEATURE:
<223> OTHER INFORMATION: primer

<400> SEQUENCE: 27
actttttgca gtactaaccg cagacctcta tcaacgtgaa gctg 44

<210> SEQ ID NO 28
<211> LENGTH: 40
<212> TYPE: DNA
<213> ORGANISM: artificial sequence
<220> FEATURE:
<223> OTHER INFORMATION: primer

<400> SEQUENCE: 28
gcaagaccgg caacgtgggg ttaagatcgg ccgttttggg 40

<210> SEQ ID NO 29
<211> LENGTH: 44
<212> TYPE: DNA
<213> ORGANISM: artificial sequence
<220> FEATURE:
<223> OTHER INFORMATION: primer

<400> SEQUENCE: 29
actttttgca gtactaaccg cagaacatgt ctgtgctgac cctg 44

<210> SEQ ID NO 30
<211> LENGTH: 40
<212> TYPE: DNA
<213> ORGANISM: artificial sequence
<220> FEATURE:
<223> OTHER INFORMATION: primer

<400> SEQUENCE: 30

-continued gcaagaccgg caacgtgggg ttactcggcc ttggtggcct 40

<210> SEQ ID NO 31
<211> LENGTH: 47
<212> TYPE: DNA
<213> ORGANISM: artificial sequence
<220> FEATURE:
<223> OTHER INFORMATION: primer

<400> SEQUENCE: 31
actttttgca gtactaaccg cagatcatca agaacaacaa caacggc 47

<210> SEQ ID NO 32
<211> LENGTH: 42
<212> TYPE: DNA
<213> ORGANISM: artificial sequence
<220> FEATURE:
<223> OTHER INFORMATION: primer

<400> SEQUENCE: 32
gcaagaccgg caacgtgggg ttagtctcgc ttggtgggct tc 42

<210> SEQ ID NO 33
<211> LENGTH: 43
<212> TYPE: DNA
<213> ORGANISM: artificial sequence
<220> FEATURE:
<223> OTHER INFORMATION: primer

<400> SEQUENCE: 33
actttttgca gtactaaccg cagtctgtgc tgaccctgca gga 43

<210> SEQ ID NO 34
<211> LENGTH: 40
<212> TYPE: DNA
<213> ORGANISM: artificial sequence
<220> FEATURE:
<223> OTHER INFORMATION: primer

<400> SEQUENCE: 34
gcaagaccgg caacgtgggg ttagtcggcc ttggtggcct 40

<210> SEQ ID NO 35
<211> LENGTH: 43
<212> TYPE: DNA
<213> ORGANISM: artificial sequence
<220> FEATURE:
<223> OTHER INFORMATION: primer

<400> SEQUENCE: 35
actttttgca gtactaaccg cagtcctccg tggtcgagac ctg 43

<210> SEQ ID NO 36
<211> LENGTH: 46
<212> TYPE: DNA
<213> ORGANISM: artificial sequence
<220> FEATURE:
<223> OTHER INFORMATION: primer

<400> SEQUENCE: 36
gcaagaccgg caacgtgggg ttaacccaga ataccctcag agtcag 46

<210> SEQ ID NO 37
<211> LENGTH: 44
<212> TYPE: DNA
<213> ORGANISM: artificial sequence -continued
<220> FEATURE:
<223> OTHER INFORMATION: primer

<400> SEQUENCE: 37 acttttgca gtactaaccg cagaccgtca agacccgatc caac 44

<210> SEQ ID NO 38
<211> LENGTH: 50
<212> TYPE: DNA
<213> ORGANISM: artificial sequence
<220> FEATURE:
<223> OTHER INFORMATION: primer

<400> SEQUENCE: 38
gcaagaccgg caacgtgggg ttacataata gatttacctc gctggatgtc 50

<210> SEQ ID NO 39
<211> LENGTH: 43
<212> TYPE: DNA
<213> ORGANISM: artificial sequence
<220> FEATURE:
<223> OTHER INFORMATION: primer

<400> SEQUENCE: 39 acttttgca gtactaaccg caggccaccc ccctgcctcc tac 43

<210> SEQ ID NO 40
<211> LENGTH: 45
<212> TYPE: DNA
<213> ORGANISM: artificial sequence
<220> FEATURE:
<223> OTHER INFORMATION: primer

<400> SEQUENCE: 40
gcaagaccgg caacgtgggg ttactcctcc ttagagtggt cgccg 45

<210> SEQ ID NO 41
<211> LENGTH: 44
<212> TYPE: DNA
<213> ORGANISM: artificial sequence
<220> FEATURE:
<223> OTHER INFORMATION: primer

<400> SEQUENCE: 41 acttttgca gtactaaccg cagtctctgt ctgcctctga gaag 44

<210> SEQ ID NO 42
<211> LENGTH: 40
<212> TYPE: DNA
<213> ORGANISM: artificial sequence
<220> FEATURE:
<223> OTHER INFORMATION: primer

<400> SEQUENCE: 42
gcaagaccgg caacgtgggg ttatcggacc atggccattc 40

<210> SEQ ID NO 43
<211> LENGTH: 44
<212> TYPE: DNA
<213> ORGANISM: artificial sequence
<220> FEATURE:
<223> OTHER INFORMATION: primer

<400> SEQUENCE: 43 acttttgca gtactaaccg cagtctgtga cctctaccgt ggag 44

<210> SEQ ID NO 44
<211> LENGTH: 40
<212> TYPE: DNA
<213> ORGANISM: artificial sequence
<220> FEATURE:
<223> OTHER INFORMATION: primer

<400> SEQUENCE: 44
gcaagaccgg caacgtgggg tcatctcacg atggccattc 40

<210> SEQ ID NO 45
<211> LENGTH: 44
<212> TYPE: DNA
<213> ORGANISM: artificial sequence
<220> FEATURE:
<223> OTHER INFORMATION: primer

<400> SEQUENCE: 45
actttttgca gtactaaccg cagaattttc atcatctggc ttac 44

<210> SEQ ID NO 46
<211> LENGTH: 42
<212> TYPE: DNA
<213> ORGANISM: artificial sequence
<220> FEATURE:
<223> OTHER INFORMATION: primer

<400> SEQUENCE: 46
gcaagaccgg caacgtgggg tcaggcctcc aggcttatcc ag 42

<210> SEQ ID NO 47
<211> LENGTH: 40
<212> TYPE: DNA
<213> ORGANISM: artificial sequence
<220> FEATURE:
<223> OTHER INFORMATION: primer

<400> SEQUENCE: 47
actttttgca gtactaaccg cagagtgaag gccccgtcaa 40

<210> SEQ ID NO 48
<211> LENGTH: 43
<212> TYPE: DNA
<213> ORGANISM: artificial sequence
<220> FEATURE:
<223> OTHER INFORMATION: primer

<400> SEQUENCE: 48
gcaagaccgg caacgtgggg ctaattatcc ttcgtatctt ctg 43

<210> SEQ ID NO 49
<211> LENGTH: 40
<212> TYPE: DNA
<213> ORGANISM: artificial sequence
<220> FEATURE:
<223> OTHER INFORMATION: primer

<400> SEQUENCE: 49
tctcaagggc atcggtcgac caacttttct tgtcgacctg 40

<210> SEQ ID NO 50
<211> LENGTH: 32
<212> TYPE: DNA
<213> ORGANISM: artificial sequence
<220> FEATURE:
<223> OTHER INFORMATION: primer

<400> SEQUENCE: 50
cacgctccat ttagcgtgtc gtgtttttgt tg 32

<210> SEQ ID NO 51
<211> LENGTH: 40
<212> TYPE: DNA
<213> ORGANISM: artificial sequence
<220> FEATURE:
<223> OTHER INFORMATION: primer

<400> SEQUENCE: 51
tctcaagggc atcggtcgac agagaccggg ttggcggcgc 40

<210> SEQ ID NO 52
<211> LENGTH: 41
<212> TYPE: DNA
<213> ORGANISM: artificial sequence
<220> FEATURE:
<223> OTHER INFORMATION: primer

<400> SEQUENCE: 52
caacgtgggg ctgcggttag tactgcaaaa agtgctggtc g 41

<210> SEQ ID NO 53
<211> LENGTH: 40
<212> TYPE: DNA
<213> ORGANISM: artificial sequence
<220> FEATURE:
<223> OTHER INFORMATION: primer

<400> SEQUENCE: 53
tctcaagggc atcggtcgac aaggagtttg gcgcccgttt 40

<210> SEQ ID NO 54
<211> LENGTH: 37
<212> TYPE: DNA
<213> ORGANISM: artificial sequence
<220> FEATURE:
<223> OTHER INFORMATION: primer

<400> SEQUENCE: 54
cacgctccat tgctgtagat atgtcttgtg tgtaagg 37

<210> SEQ ID NO 55
<211> LENGTH: 39
<212> TYPE: DNA
<213> ORGANISM: artificial sequence
<220> FEATURE:
<223> OTHER INFORMATION: primer

<400> SEQUENCE: 55
tctcaagggc atcggtcgac tttgtgcaag tgtgtgtgt 39

<210> SEQ ID NO 56
<211> LENGTH: 30
<212> TYPE: DNA
<213> ORGANISM: artificial sequence
<220> FEATURE:
<223> OTHER INFORMATION: primer

<400> SEQUENCE: 56
cacgctccat agtagatgtg taagtgtgta 30

<210> SEQ ID NO 57

```
<211> LENGTH: 40
<212> TYPE: DNA
<213> ORGANISM: artificial sequence
<220> FEATURE:
<223> OTHER INFORMATION: primer

<400> SEQUENCE: 57

tctcaagggc atcggtcgac cgcagtagga tgtcctgcac                              40


<210> SEQ ID NO 58
<211> LENGTH: 46
<212> TYPE: DNA
<213> ORGANISM: artificial sequence
<220> FEATURE:
<223> OTHER INFORMATION: primer

<400> SEQUENCE: 58

gtgtagatac tgttgatgtg tgtttaattc aagaatgaat atagag                      46


<210> SEQ ID NO 59
<211> LENGTH: 30
<212> TYPE: DNA
<213> ORGANISM: artificial sequence
<220> FEATURE:
<223> OTHER INFORMATION: primer

<400> SEQUENCE: 59

ctaaccgcag ccccacgttg ccggtcttgc                                        30


<210> SEQ ID NO 60
<211> LENGTH: 41
<212> TYPE: DNA
<213> ORGANISM: artificial sequence
<220> FEATURE:
<223> OTHER INFORMATION: primer

<400> SEQUENCE: 60

gctgtcaaac atgagaattc ggacacgggc atctcacttg c                           41


<210> SEQ ID NO 61
<211> LENGTH: 30
<212> TYPE: DNA
<213> ORGANISM: artificial sequence
<220> FEATURE:
<223> OTHER INFORMATION: primer

<400> SEQUENCE: 61

cacatcaaca gtatctacac gcgtgctatg                                        30


<210> SEQ ID NO 62
<211> LENGTH: 44
<212> TYPE: DNA
<213> ORGANISM: artificial sequence
<220> FEATURE:
<223> OTHER INFORMATION: primer

<400> SEQUENCE: 62

gctgtcaaac atgagaattc ctaccttgct cgaatgactt attg                        44


<210> SEQ ID NO 63
<211> LENGTH: 31
<212> TYPE: DNA
<213> ORGANISM: artificial sequence
<220> FEATURE:
<223> OTHER INFORMATION: primer

<400> SEQUENCE: 63
```

atctacagca atggagcgtg tgttctgagt c 31

<210> SEQ ID NO 64
<211> LENGTH: 38
<212> TYPE: DNA
<213> ORGANISM: artificial sequence
<220> FEATURE:
<223> OTHER INFORMATION: primer

<400> SEQUENCE: 64
gctgtcaaac atgagaattc atttcttgac ctcatcaa 38

<210> SEQ ID NO 65
<211> LENGTH: 49
<212> TYPE: DNA
<213> ORGANISM: artificial sequence
<220> FEATURE:
<223> OTHER INFORMATION: primer

<400> SEQUENCE: 65
ctcacatcac atccgaacat aaacaaccat gaaaaagcct gaactcacc 49

<210> SEQ ID NO 66
<211> LENGTH: 48
<212> TYPE: DNA
<213> ORGANISM: artificial sequence
<220> FEATURE:
<223> OTHER INFORMATION: primer

<400> SEQUENCE: 66
acaagaatct ttttattgtc agtactgact attcctttgc cctcggac 48

<210> SEQ ID NO 67
<211> LENGTH: 41
<212> TYPE: DNA
<213> ORGANISM: artificial sequence
<220> FEATURE:
<223> OTHER INFORMATION: primer

<400> SEQUENCE: 67
tacaaccaca cacatccaca atggaacccg aaactaagaa g 41

<210> SEQ ID NO 68
<211> LENGTH: 40
<212> TYPE: DNA
<213> ORGANISM: artificial sequence
<220> FEATURE:
<223> OTHER INFORMATION: primer

<400> SEQUENCE: 68
agggcccttt ttatagagtc ttatacacta gcggaccctg 40

<210> SEQ ID NO 69
<211> LENGTH: 40
<212> TYPE: DNA
<213> ORGANISM: artificial sequence
<220> FEATURE:
<223> OTHER INFORMATION: primer

<400> SEQUENCE: 69
tacaaccaca cacatccaca atgccctcct acgaagctcg 40

<210> SEQ ID NO 70
<211> LENGTH: 48
<212> TYPE: DNA

<213> ORGANISM: artificial sequence
<220> FEATURE:
<223> OTHER INFORMATION: primer

<400> SEQUENCE: 70
agggcccttt ttatagagtc ctaacagtta atcttctggt aagcctcc 48

<210> SEQ ID NO 71
<211> LENGTH: 21
<212> TYPE: DNA
<213> ORGANISM: artificial sequence
<220> FEATURE:
<223> OTHER INFORMATION: primer

<400> SEQUENCE: 71
aattccgtcg tcgcctgagt c 21

<210> SEQ ID NO 72
<211> LENGTH: 21
<212> TYPE: DNA
<213> ORGANISM: artificial sequence
<220> FEATURE:
<223> OTHER INFORMATION: primer

<400> SEQUENCE: 72
gtcgaccgat gcccttgaga g 21

<210> SEQ ID NO 73
<211> LENGTH: 46
<212> TYPE: DNA
<213> ORGANISM: artificial sequence
<220> FEATURE:
<223> OTHER INFORMATION: primer

<400> SEQUENCE: 73
tctcaagggc atcggtcgac cccggggtgg taatcgaccg actaac 46

<210> SEQ ID NO 74
<211> LENGTH: 41
<212> TYPE: DNA
<213> ORGANISM: artificial sequence
<220> FEATURE:
<223> OTHER INFORMATION: primer

<400> SEQUENCE: 74
actcaggcga cgacggaatt tgacgaggtc tggatggaag g 41

<210> SEQ ID NO 75
<211> LENGTH: 22
<212> TYPE: DNA
<213> ORGANISM: artificial sequence
<220> FEATURE:
<223> OTHER INFORMATION: primer

<400> SEQUENCE: 75
gatctcggca gtctctcgga tg 22

<210> SEQ ID NO 76
<211> LENGTH: 20
<212> TYPE: DNA
<213> ORGANISM: artificial sequence
<220> FEATURE:
<223> OTHER INFORMATION: primer

<400> SEQUENCE: 76
tgttcggaaa tcaacggatg 20

<210> SEQ ID NO 77
<211> LENGTH: 40
<212> TYPE: DNA
<213> ORGANISM: artificial sequence
<220> FEATURE:
<223> OTHER INFORMATION: primer

<400> SEQUENCE: 77
catccgttga tttccgaaca tttgagccga ggcagatttg 40

<210> SEQ ID NO 78
<211> LENGTH: 47
<212> TYPE: DNA
<213> ORGANISM: artificial sequence
<220> FEATURE:
<223> OTHER INFORMATION: primer

<400> SEQUENCE: 78
tccgagagac tgccgagatc cccgggtcag agagaaggac tatggag 47

<210> SEQ ID NO 79
<211> LENGTH: 38
<212> TYPE: DNA
<213> ORGANISM: artificial sequence
<220> FEATURE:
<223> OTHER INFORMATION: primer

<400> SEQUENCE: 79
gaattctcat gtttgacagc ttatcatcga tgataagc 38

<210> SEQ ID NO 80
<211> LENGTH: 21
<212> TYPE: DNA
<213> ORGANISM: artificial sequence
<220> FEATURE:
<223> OTHER INFORMATION: primer

<400> SEQUENCE: 80
gtcgaccgat gcccttgaga g 21

<210> SEQ ID NO 81
<211> LENGTH: 20
<212> TYPE: DNA
<213> ORGANISM: artificial sequence
<220> FEATURE:
<223> OTHER INFORMATION: primer

<400> SEQUENCE: 81
ccccacgttg ccggtcttgc 20

<210> SEQ ID NO 82
<211> LENGTH: 22
<212> TYPE: DNA
<213> ORGANISM: artificial sequence
<220> FEATURE:
<223> OTHER INFORMATION: primer

<400> SEQUENCE: 82
ctgcggttag tactgcaaaa ag 22

<210> SEQ ID NO 83
<211> LENGTH: 1545
<212> TYPE: DNA
<213> ORGANISM: Yarrowia lipolytica
<220> FEATURE:

-continued

<223> OTHER INFORMATION: Yarrowia lipolytica DGAT1

<400> SEQUENCE: 83

```
atgactatcg actcacaata ctacaagtcg cgagacaaaa acgacacggc acccaaaatc     60
gcgggaatcc gatatgcccc gctatcgaca ccattactca accgatgtga gaccttctct    120
ctggtctggc acattttcag cattcccact ttcctcacaa ttttcatgct atgctgcgca    180
attccactgc tctggccatt tgtgattgcg tatgtagtgt acgctgttaa agacgactcc    240
ccgtccaacg gaggagtggt caagcgatac tcgcctattt caagaaactt cttcatctgg    300
aagctctttg gccgctactt ccccataact ctgcacaaga cggtggatct ggagcccacg    360
cacacatact accctctgga cgtccaggag tatcacctga ttgctgagag atactggccg    420
cagaacaagt acctccgagc aatcatctcc accatcgagt actttctgcc cgccttcatg    480
aaacggtctc tttctatcaa cgagcaggag cagcctgccg agcgagatcc tctcctgtct    540
cccgtttctc ccagctctcc gggttctcaa cctgacaagt ggattaacca cgacagcaga    600
tatagccgtg gagaatcatc tggctccaac ggccacgcct cgggctccga acttaacggc    660
aacggcaaca atggcaccac taaccgacga cctttgtcgt ccgcctctgc tggctccact    720
gcatctgatt ccacgcttct taacgggtcc ctcaactcct acgccaacca gatcattggc    780
gaaaacgacc cacagctgtc gcccacaaaa ctcaagccca ctggcagaaa atacatcttc    840
ggctaccacc cccacggcat tatcggcatg ggagcctttg gtggaattgc caccgaggga    900
gctggatggt ccaagctctt tccgggcatc cctgtttctc ttatgactct caccaacaac    960
ttccgagtgc ctctctacag agagtacctc atgagtctgg gagtcgcttc tgtctccaag   1020
aagtcctgca aggccctcct caagcgaaac cagtctatct gcattgtcgt tggtggagca   1080
caggaaagtc ttctggccag acccggtgtc atggacctgg tgctactcaa gcgaaagggt   1140
tttgttcgac ttggtatgga ggtcggaaat gtcgcccttg ttcccatcat ggcctttggt   1200
gagaacgacc tctatgacca ggttagcaac gacaagtcgt ccaagctgta ccgattccag   1260
cagtttgtca agaacttcct tggattcacc cttcctttga tgcatgcccg aggcgtcttc   1320
aactacgatg tcggtcttgt cccctacagg cgacccgtca acattgtggt tggttccccc   1380
attgacttgc cttatctccc acaccccacc gacgaagaag tgtccgaata ccacgaccga   1440
tacatcgccg agctgcagcg aatctacaac gagcacaagg atgaatattt catcgattgg   1500
accgaggagg gcaaaggagc cccagagttc cgaatgattg agtaa                   1545
```

<210> SEQ ID NO 84
<211> LENGTH: 1449
<212> TYPE: DNA
<213> ORGANISM: Yarrowia lipolytica
<220> FEATURE:
<223> OTHER INFORMATION: gene SCD

<400> SEQUENCE: 84

```
atggtgaaaa acgtggacca agtggatctc tcgcaggtcg acaccattgc ctccggccga     60
gatgtcaact acaaggtcaa gtacacctcc ggcgttaaga tgagccaggg cgcctacgac    120
gacaagggcc gccacatttc cgagcagccc ttcacctggg ccaactggca ccagcacatc    180
aactggctca acttcattct ggtgattgcg ctgcctctgt cgtcctttgc tgccgctccc    240
ttcgtctcct tcaactggaa gaccgccgcg tttgctgtcg gctattacat gtgcaccggt    300
ctcggtatca ccgccggcta ccaccgaatg tgggcccatc gagcctacaa ggccgctctg    360
cccgttcgaa tcatccttgc tctgtttgga ggaggagctg tcgagggctc catccgatgg    420
```

```
tgggcctcgt ctcaccgagt ccaccaccga tggaccgact ccaacaagga cccttacgac    480
gcccgaaagg gattctggtt ctcccacttt ggctggatgc tgcttgtgcc caaccccaag    540
aacaagggcc gaactgacat ttctgacctc aacaacgact gggttgtccg actccagcac    600
aagtactacg tttacgttct cgtcttcatg gccattgttc tgcccaccct cgtctgtggc    660
tttggctggg gcgactggaa gggaggtctt gtctacgccg gtatcatgcg atacaccttt    720
gtgcagcagg tgactttctg tgtcaactcc cttgcccact ggattggaga gcagcccttc    780
gacgaccgac gaactccccg agaccacgct cttaccgccc tggtcacctt tggagagggc    840
taccacaact tccaccacga gttcccctcg gactaccgaa acgccctcat ctggtaccag    900
tacgacccca ccaagtggct catctggacc ctcaagcagg ttggtctcgc ctgggacctc    960
cagaccttct cccagaacgc catcgagcag ggtctcgtgc agcagcgaca gaagaagctg   1020
gacaagtggc gaaacaacct caactggggt atccccattg agcagctgcc tgtcattgag   1080
tttgaggagt tccaagagca ggccaagacc cgagatctgg ttctcatttc tggcattgtc   1140
cacgacgtgt ctgcctttgt cgagcaccac cctggtggaa aggccctcat tatgagcgcc   1200
gtcggcaagg acggtaccgc tgtcttcaac ggaggtgtct accgacactc caacgctggc   1260
cacaacctgc ttgccaccat gcgagtttcg gtcattcgag gcggcatgga ggttgaggtg   1320
tggaagactg cccagaacga aaagaaggac cagaacattg tctccgatga gagtggaaac   1380
cgaatccacc gagctggtct ccaggccacc cgggtcgaga accccggtat gtctggcatg   1440
gctgcttag                                                           1449
```

<210> SEQ ID NO 85
<211> LENGTH: 1647
<212> TYPE: DNA
<213> ORGANISM: Yarrowia lipolytica
<220> FEATURE:
<223> OTHER INFORMATION: gene PLA2-1

<400> SEQUENCE: 85

```
atgagaatct ctctactttg tgttgcaact ctttgcagct ctgtcttggc cctctacaca     60
ccccaacgtg gaacatgtcc ttcttcacct ctacttcgac aagccaaggg acttcaaagc    120
gatgaagcag agtacatgtc cagccgtcgg aacaagacca aacctgcctt gagtaccttt    180
ctgaaaaagc aaaacattga caatttcgat gtcgattcct tcctcgaacg ggcgtccccc    240
aagttggctg tggctgccgc tggaggaggc ctgagagcca cttatatggg catgggtaca    300
ttccaggcac tcgacaaccg aacagagaac tccactcttg ccggttacct ccaggccgtc    360
gactacatgt cgggattgtc tgggggttcg tggctagtag gctacctagc tatcaacgat    420
tatccagatt tccagactct tttccacgcg tttgacggca ttttcaatct tccaggatcc    480
atgggaactc tgggaatgct agctaaagtg ttcattgact cccttcagaa actcaaggct    540
ggttatcaga cgtcggtcac tgaccagtgg ggaagactta tctacctgtt gttgggcaac    600
gctgggctgc taaaagcaga ttttaattgg tcggacatcc gaaatctgac ctccttcaca    660
tctcatgaaa tgcccttccc catcattctt ggtaccactg tttttcccgg ctcttctttc    720
gacgtggagt acataaccta taacaactcg atcatggaaa tgactccata tgagttcgga    780
acatgggaca aaaacatccg ggagttcatc gacatgcagt atctgggcac tgaaatggaa    840
aacggcaccc ccgtgggtga atgtaccacc aattacgaca acgccggcct tctgatgggc    900
atttcttcca acgtgttcaa tgcgggtcta gacggacttg gaatcgacgg aatttttgga    960
```

-continued

```
atcttggtcg aagatcttat gaaactgctg gaaatcatca acgacgcctc ttaccgcctc   1020
ggtgtcattt ctcctaaccc gttctacaag caggatgaca ttccttcgaa ccagaccatc   1080
tccagaggtc tactagtgtg tgacggaggc tttgatctcg aaactatccc catcctgccc   1140
tttttgcaac ccgaacgaga agttgatgtt gtcatctcca tggatccttc tctagacagc   1200
cccgagggat ggcccactgg agaatgtatc agacataccg cagccaaaag tcaatgggag   1260
tttggagagg gagtgttccc ccagattccc gacaatgtca ccttcatcaa cgacaacctc   1320
accaccaagc ctgtcttctt tggttgcaac atcaccaacc tgaagaagta cgataacacc   1380
gacagatact ctccggtcat cgtctacgta cccatgcaca acatttccta cgtgtccaac   1440
ttctccactg gaaagctctt gtataccaag gaggaaagct tcggaaccgt caacaatgcg   1500
tacaacatga tgacaaggac aaacttgacc gaagatgaag aatggggcaa atgcctaggt   1560
tgcgtttcca ttctccgaga gctgcagaga ttgaatgaga ccgtgccgga ttgtgagagg   1620
tgtttcagca attactgcta caactga                                       1647
```

<210> SEQ ID NO 86
<211> LENGTH: 1653
<212> TYPE: DNA
<213> ORGANISM: Yarrowia lipolytica
<220> FEATURE:
<223> OTHER INFORMATION: gene PLA2-2

<400> SEQUENCE: 86

```
atgcaattac ggttgatttt gacggcattt gcctctttgg caattgcaga ctacactcct     60
gtgcgagttc catgtccctc caccaatctt acgcgtcctg ccattggact gaatcctgac    120
gaatctgctt acattgagca gcgacatacc aagaccagag aaagcctcaa gacatttctg    180
aagactctag aaagttcctc ttttgatgtt gatgcctttc tgaatgagag gtctcccaag    240
atcgccgttg caattgctgg aggaggagta agagcttctc tgtttggagc cggagttttg    300
gctggtctgg atggtcgagt ttcccaaaac ggtaccgggg gtctgcttca ggcaacagac    360
tacatttctg gtctttctgg gggctcctgg cttgttggac tgctctgttt gtctgactgg    420
atagccgctg accagctagt tggaatgagc gagaaaatga agttcccagg catgcttgac    480
acttttggca tgatgctcaa gattctcaca gacaccatgg ctaagaaaaa ggccggctac    540
cagacatccg tggttgatca gtggggcaga ctgttccatt ttgtgactgc cgaagctggt    600
ttgaactaca cggatccgac atggagtgga attcgcaacc tgagctcgtt cctggacttc    660
tccatgccct ttcctataat cacctcaact tctttatttc caggaacctc gtttgacgtc    720
acccatatcg actatatcaa ccccatggtt gaaatgacac ccttcgagtt cggaagctgg    780
gacagaaact tccgttactt cgctgacact gtgtttctgg gcacggagat ggaagacgcg    840
aagcccctga atcagtgtgt gcgtaattac gacaatcacg gtctattcct gggttcttca    900
ggtggaatct tcaatgctga cgtgatcggc ggatttgaaa tgaaaggctt acatgcgata    960
tttttgtctg gagtcttgga gtatcttgat cttgtcaacg aaggtgagtt ccgagtagga   1020
cttattcaga accccttcta caagatggca catctagtct ccaaccagac aatctccagg   1080
ttcatgtact tgtgcgatgg agggtttgag aagcaacaaa acattccttt gcttcctttt   1140
cttcagcctg aacgagaaat agatcttctc tttgccactg atccatcaac agatactatg   1200
gatggtcatg gatggcccaa tggagcttct ctgagacaca caaaggagaa gagtgacctg   1260
gagtttggca aaggaattta ccctgaaatt cccgaggagg acgagtactt gagcagaaac   1320
ttgtccatgc aacctgcctt ctttggctgc gatatcgctt ctctgaaaca gtacaacaat   1380
```

```
acgcaacggt atgcccctgt gattgtcaac attcccatgg gaaacctgac gtatgcttcg   1440

aatttctcga ctggtaagtt cttttacact catgaagaaa cccagggaac ctatttgaat   1500

gcctacaata tggccactag gtccaacttg accgaggacg agaattggaa cgtgtgtcta   1560

gggtgcgtat cactgttgcg cgaatttcag agacggtcca gtgaaatccc cgaccaatgt   1620

cagacctgct tcaaccgcta ctgttttaac taa                                1653


<210> SEQ ID NO 87
<211> LENGTH: 1917
<212> TYPE: DNA
<213> ORGANISM: Yarrowia lipolytica
<220> FEATURE:
<223> OTHER INFORMATION: gene PLA2-3

<400> SEQUENCE: 87

atgaaattct ctccactttt gctggcgacc gtgggtctgg cccagagctt ctattcgccc     60

accgactcgt acgcgcccgg gtcggtcgac tgtccctcca actccaccca gattgtgcga    120

aagggcgagg gcctttcttc gcaggaacga gagtgggtcc agaaccgaca cgaacagacc    180

cgaccggagc tgctcaacta cctgaaacgg gtgggcttta agtcggtgga cccggaccag    240

ttcctgggcc aggacactaa tatcaccatc ggactgtcct tttctggagg aggatacaga    300

gccatgttgg cgggagcagg ccaatttgcg gctctggacg cgcgaacacc caacgccacc    360

gaaccgggcc atgtgggagg tctggtccag gccgccacct atctggtggg tctttcgggc    420

ggaaactgga tggtgggatc tgtggtcatc aacaacttca ccaccattcc cgacctgcaa    480

cactcgtccg acgtgtggga cctggaacac tccatgatca accccggcgg aatcaacatc    540

ttcaagaccg gctcttattg ggacgacatc aacgacgacg tcaacgacaa gcagcacgcc    600

ggatacaaca cctctttcac cgacatctgg ggccgaggtc tgtcgtacca gttcttcaac    660

gcttccaaca ccgcccgact cacctggtcc gagatccaga actacgacca cttcaagaac    720

cactctatgc cctaccccat tgttgtggcc gacggccgag cccccggaac ccgaatcatc    780

tccggaaact ccaccatttt cgagctggcc ccgttcgagg tcggctcctg ggaccccaat    840

gtctactcct ttgccaagac cgagtggctg ggaaccaaca tgaccaacgg ccgacccaac    900

ggaacctgtg tgcatggctt tgacaacgcc ggtttcattg tgggaacctc ttcttccctg    960

ttcaaccagt tcattctcca gctcaactcc accggagtaa ccggagtggt ctacgacctg   1020

gcccactcta tcctcaagcg tctggataag gactcggacg atatcgccat ctactcgccc   1080

aaccccttca agggcatgtc ctacctcggc aactcgtcca ttgcccaaac cgagtatctg   1140

gatctggtcg acggaggaga agatggacag aatgtgccct actaccctct gctgcagccc   1200

gagagagccg tcgacgtggt catctcctac gacaactccg ccgacaccga ctttaactgg   1260

cccaacggaa cctccgctgt ccagacatac cgacgacagt ttgagaacca ggccaatggc   1320

accattttcc cctacgtgcc cgacgtgaac acattcatca atgagaacct gacttctcga   1380

cccgccttct ttggctgtga cgtgcagaac atgacctcgc tggacaagaa cggttatacc   1440

gacgtcaact cttccgccgc ccttcccccct ctcattgtct acattgctaa ctacccctgg   1500

accttttttct ccaacacatc gaccatgtcc aagctgtcgt acaacaagaa ggaggttgcc   1560

ggcatgatcg agaacggcta ctccacctcc acccagttca acggaaccgt ggaccccgac   1620

tggcctgtgt gtcttggctg tgctctgctc aagcgagagg ccacccgacg aaaccagtct   1680

ctgggctctg actgtgacaa gtgcttctcc aagtactgct ggaacggaaa gactgacgat   1740
```

gatgccgaaa aggctctgaa gtttgctccc gccatctatg ccaacggccc taacgtttct 1800
tccaacgcct caattggcca ggcttcgtcc acctccaagc ccaagaagaa cggcgccgag 1860
ggtctggttc cgggtatggc tgccattgcc attggttttg ccgctcttct tatgtaa 1917

<210> SEQ ID NO 88
<211> LENGTH: 1710
<212> TYPE: DNA
<213> ORGANISM: Yarrowia lipolytica
<220> FEATURE:
<223> OTHER INFORMATION: gene PLA2-4

<400> SEQUENCE: 88
atgaagttct cggctaccat tctgaccgcc ctggcagcct cggcggttgc caactacgcc 60
cccatcaagg tggagtgtcc aaaagatgtc aacatctccc gaccagcaga cggcctgagc 120
caccaggagg ccgactacat caatgaacga cacaaaaaga cctccaaggc gctcagagag 180
tacctcggtg ggctcgacat caaggcccga ggcaacaaca ccttcgacac ggactctttt 240
ctgaacgaaa cctcccccaa gctcgccatt gcggctgccg gaggaggttt ccgggccatg 300
ctggttggag caggcgtcat tgctgccctg gacaagcgtg tggacgaaaa caacaagaac 360
ggaggctttc tgcagtccgc agactatctg gccggtttgt ctggaggagc ttggctcgtg 420
ggatctctgg tcctcaacga ctggcctact gtgcctgaga tccaggctga cccccaaatc 480
tggtacctca acaagtcctt ggtgggctca gtcgaacccg gatccatgaa caccgtcggc 540
ctcttcgcca aggtgcttgc agataccacc tccaagcttg ctgccggcta ccagacctcg 600
ctgaccgacc aatggggacg actggtgtca taccagacca tcaactcttc gcacaccaag 660
ggcggtctgg atgccaccga ggtgacctgg tctggcatca gaaacatctc ctctttcgtt 720
gaccatgaaa tgccctttcc catcattctg ggcacatctc ttttccccgg aacttctcac 780
gatgttgacc agattaaatt caacaactcc atcatcgaaa tgacccccta cgagtgggga 840
acctgggaca agaacatccg gcaatttgtc gacaccgagt acctgggtac cgagatgtcc 900
gacggaaagc ccacaggaaa ctgtacccga cgatacgata acgccggctt cctgatggga 960
acctcctcct caattttcaa catggacatg aagactctgg gctttggcgg ctttgagagc 1020
gtgctactgc aggatctctt ctccgctctg gatattgtca acgagggctc tttcaacgtg 1080
gctgtttaca accccaaccc tttctaccaa caggttggca tgcagaccaa tcagaccatc 1140
tccaaggctc tgtacgtgtg tgacggaggt ttcgacaagg agaccattcc cattctgcct 1200
ttccttcagc ccgagagaga ggtcgatgtt gtcattgcca tcgacccttc cactgatact 1260
gaggaaagct ggcccgatgg agagtctctt cgagccaccc agaacaagtc cgactgggag 1320
tttggagacg acgtgtttcc caagatcccc tctaacgaga ccttcatcag caagaatctg 1380
actaccaagc ctgtcttctt cggctgcaac accaccaatc tcaagacgta caaggactcg 1440
gatcgatact ctcccgtcat tgtctacgtg cccatgtctg acatcaccta cccctccaac 1500
ttctccaccg gcaagctgtc ctacaccaac gaggaacagc agcgaaccat caacaacggc 1560
tacaacatga tgactcgaag caacggaacc gaggattcca actgggacaa gtgtctgggc 1620
tgtgtgactc tgctgcgaga gttccagcga cgggactcgg atgttcccaa tgactgtgag 1680
cagtgtttct ccgactactg ttacaactaa 1710

<210> SEQ ID NO 89
<211> LENGTH: 1623
<212> TYPE: DNA
<213> ORGANISM: Yarrowia lipolytica
<220> FEATURE:
<223> OTHER INFORMATION: gene PLA2-5

<400> SEQUENCE: 89

```
atgatcgcaa acttcctgct gcttctggtg ctggtcacct tcgctgcagc ctcctacact      60
ccctccaagg gaagctgcca atacgacacc aacctgcttc gagaagcctc cagtatctct     120
cctgatgagg ccaactacgt tgcctccaag cagtccagtt ccgattccgc tttccagagc     180
tacctcaaga acgtcaacat ccctggtctg gatgtgaacc agtctgccaa cattgccctt     240
tccttctctg gaggaggata tcgagctatg ttgtccggtg ctggccaatt ttctgctctg     300
gatagccgaa acgagatcgc caacactatg ggaggtcttt tacaggcatc caactatctt     360
gtcggatgct ctggaggtgg atggctggtc ggcactattg ccatgaacaa cttccctact     420
atcgctgagg tccgatccaa ctctgacctg tggaagatca atgacaatgt tcccgagctt     480
actaaccctc tttcttggtt ggcgtttggt agatatgctg gcattgttac tgctgccctt     540
ggaaagcgtt tggccggatt taaaatctct ttcaccgacg agtggggtct gctcgtgggg     600
cgaaatcttg ttgataagaa cggcccatac tctacctggt ccgacatcaa ggtcacccaa     660
tcttacctgt ccaacgagat tcccttccct atcattgtcg gtaccactct gaacagcgct     720
gatgagcagg aggctcagat tactatcgac aacccttga ttgagatgac cccccattgag     780
ttcggctcct tcgacaagtc catcaaatct ttcttcacta cttctgctat tggtacttct     840
gtttctaacg gccagcccac ctcttcccga tgtgtcactg gcttcgacaa tgcccagttc     900
ctgctgggaa ccacatccag tcttttccag ggtgtcagtg gatggcagaa gactatgctg     960
aacattgttg ggctcttaa cggcaacatc gcacccagtg ccatctatca ccccaaccct    1020
ttcaaggatg ccagctcggt ccaggctcct ttcaacggtg actctctcta tgcttcagac    1080
ggaggttatt ctggcatggt tcttccccctg tggcccctta tgcagccatc tcgaaacgtg    1140
gacttggtat tctcattcga taacagcgca ggaggtccca acaatgctcc tagtggagtc    1200
actctggcta acgtgaagca gaaggtcaca aacgagatgg gcgaaggagt gttccccgag    1260
gttcccagca gcgaggagta cattgccaac taccttgtca agccagtgtg gctcggatgt    1320
gaagtttcca agctcaaaaa aatccccaac acagatcgat acgttcctct tgtcatcaca    1380
atggccaacc accagatcaa ctacaactct cttcagcaga ctgacaagat ggactatagc    1440
tctgatgagc aaactggtat gatctctaac ggttttgcag tcgcttctaa caatggtgac    1500
ctgaagtggg cccagtgtgt cggctgtgcg ggtattctcc gagagttcca gagaactggt    1560
aaggaactcc ctgaaacctg ccaggcttgt ctcaaggaat actgctatca gtactctggt    1620
taa                                                                   1623
```

<210> SEQ ID NO 90
<211> LENGTH: 3009
<212> TYPE: DNA
<213> ORGANISM: Yarrowia lipolytica
<220> FEATURE:
<223> OTHER INFORMATION: gene PLA2-6

<400> SEQUENCE: 90

```
atgcagttta cgcccttatt cctgcatttg gtggccactc ttgccgcttc ccctggcggc      60
acatatgagc ccaaacatgt tgattgtccc ccaaccgtac tggttcgaga ggccaacgat     120
accctcaatc ccaaagagaa agactacatg gaccggcgat ggctgcagac tcagcaagaa     180
catgtcaagt ttatggaacg tctcgacatt cccgacttca acgtctcctt cttggacgaa     240
```

-continued

```
gtccccccctg tcgtgatggg aactgccttc tctggaggtg gttatcgatc catgttgaca    300
ggagcaggtg tcgttgctgc catggacgcc cgtgtaaacg ggtctcttga ccttggcgcg    360
ctgggtggtc tcttccaagc aatgtcctac ttggtgggct tgtccagtgg aagttggttg    420
ttgacctctc tctttctgaa cgacaacttc actgttcctg accttcaggc tgctcctaac    480
ctctggagtc tcgagaactc attctggggt ggagaacgaa tgaaggacgt ccagcttgac    540
aaccccgttc ccaaccctgg tattattgat aacaacggaa ccgagagtga caacagttct    600
cttgtcattg gatctggcct gacagatcgt ctgagctctc gactgaagaa tctcgtcaat    660
ctagctcctc ggaacatcgt ttccgactca atcaagcacc actggaatcg acgaccttcg    720
accggtggag ctgaggttgt caaaaaacatt aacctcaacg acatgttggc caaacgacct    780
aactctggta tcgctgagcg tcttcgaaac atgcctccaa tcggtgagag catttccaat    840
ggtcggcgta ctcgtcctag cactggtttt gctgaccgtc tgagaaacag accgaagact    900
ggaatctctg acagactaca ccaccgtccc agtactggac tctctgatcg gctgcgaaac    960
aggcccagta ctggcgtttc cgacacctgg aagaatcgac ccaagactgg ctatgctgat   1020
cggctcaaga attctcaacg gccccacttc gatctcgccc aacgactcag aaatagaccc   1080
aagacaggaa tatatgataa cgtcgacaag ggatctctc gaataaaacc tgggttgtct   1140
gatgcccgaa aggctcttga caaacacatt ccttcgaaac cttcaatggg tgacttcttt   1200
aaccagagaa gacgtcagtc tgatctcgaa aagctcttgg agtacgtttc tcctgacttc   1260
ctctgtgacc tagactattc agagttcctg aagtaccttg accctctgta tacttattac   1320
cacctggaga atgagatcaa gcagaccctg tactacttcc tgatgatcaa ggaagaggtc   1380
gacctgaaat ccagtgctgg ttttgtgacc actatcactg attactgggg tcgagcactc   1440
gcccgtcagc tgcttcctga ttctcgagga ggacagggta ctacctggtc cgatgttcaa   1500
atcacacctc agttcatgaa cgcatctgtg cctttcccta tcatggttgc gattggtcga   1560
gagccctccg agtctaacag tacctacatg atctctcctc tttggtcgac tctcttcgaa   1620
atgactccct tcgagtttgg atcttggaac ccttctttaa acgccttctc tgacactcga   1680
taccttggtt catccctcta taatgggacc cccgtcaaca atgttaccct tgagcctgtt   1740
ccctcaactg agcccgtttg tgtcttggga tatgataatg ctggtttcct tgccggcact   1800
tcttcctctg tcttcaatga tcctttcgag aattcgggta tcgatcagga ctacattcga   1860
gagctcttta ctggtatcat tgatgccctt gagaatttca atacctcttt ctggggtgaa   1920
ttcttttcta cagagaacag cactgtccct gaaactgatc ttacttggcg ggacgccgac   1980
tatgccatct tctcacccaa ccccttcctt gggtttgact ctaacgccac cactgataag   2040
ttttctgagt ccaaacatct tttcctggct gatggtggtg aggatggcca gctggttccc   2100
ttcgagcccc tacttcagga acagcgtaat gttgatgtca tcttcgccat tgatgcgtct   2160
tcgaacactg aggacaactt cccagatgga actgcgctgc gtatgtcaca agagagatac   2220
ctttcggagg attctgagca ggcggctggc atatcgtttc cccagctggc tgcagagttt   2280
ggcaatgaac ctgttttcct tggatgtttc ataaactcgt cttactcggt accacccaag   2340
gggagagcct acagctataa ctatcgacga gaccgtcctg ccgagcccaa tatgactatt   2400
cctgtatatc ctcctcctcc cccgttcgat ttccctaact ctacctttga tcctaactcc   2460
actttttcaa atgttagtat ggcttccagg gctcactgga gagccagaca gattcctgtt   2520
tccaacggca ctactaatga tacgggacct ataattcgcc ctcgacctcg ccctcgaccc   2580
cggccctcac gaccccggcc tatcatcgaa gatggtcgtg actatgacgc tgactatcct   2640
```

tatgaccaca ctacccctat tggtgccatt ccagtcatgc ctcctacaaa tgtttccacc 2700
gacccctttg tcaacgttac tgttggtgtc gacaagtacc ctcctctcat tgtgtatatc 2760
ccaaacagct accaatctta ctggaccggt gatagtactt tccaggttga gttttccacc 2820
gaggatgttg ccggctacat taccaacggc tacaatctga tgaccagaca gaactccact 2880
gtcgaccccg actggaataa gtgcgttggt tgtgccacta ttctccgggc ttatcaggga 2940
gccaacaaga ccatcccaga cttttgcatg ggatgtttcg atcgatattg tgttgattca 3000
agtaaatga 3009

<210> SEQ ID NO 91
<211> LENGTH: 1413
<212> TYPE: DNA
<213> ORGANISM: Yarrowia lipolytica
<220> FEATURE:
<223> OTHER INFORMATION: gene ylGSR

<400> SEQUENCE: 91
atggcttcta tcccccatta tgactatctg gttatcggcg gaggctctgg aggtgttgct 60
tctgctcgtc gagccgcctc gtacggcgcc aaaacactgc tgatcgaggg caaggcgctg 120
ggaggcacct gcgtcaacgt gggctgtgtg cccaaaaagg tcatgtggaa cgcgtccgat 180
ctggcgggcc gaatccgaca ggccaaggag tacggcttcc ccgacgtgga ccccaagtac 240
gccgacaact ttgactggtc cggattcaag gccaagcgag acgcttacgt caagcgactc 300
aatggaatct acgaacgaaa cctccagaag gagggcgtcg agtacgtgtt tggctgggcc 360
accctctaca agcaggaggg ccaggagttc cccctggtac atgtcaagag cgacgacggc 420
aataccaagc tgtattctgc caagaagatt atgattgcca ccggcggaaa gccccgtctg 480
cccgacgtgc ctggagccga gtacggcatt gactccgacg gcttctttgc tctcgagacc 540
cagcccaagc gagtggcggt ggttggagga ggctacattg gcgtggagct ggctggtgtc 600
ttccacggac tcaactccga gaccaccctc ttctgccgag gccagacggt gctccgagcg 660
ttcgacatca tgatccagga caccatcacc gactactacg tcaaggaggg catcaacgtg 720
ctcaagggct ccggcgtcaa gaagattgtc aagaaggaca atggcgagct gctcgtcacc 780
tacgagcagg atggcgccga gaaggatatc actcttgact cacttatttg gaccattgga 840
cgagagcctc tcaaggacac cctcaacctc ggcgagtttg gcatcaagac caacaagcgg 900
ggctacattg aggtcgacga gtaccagcga tcgtccgttg acaacattta ctcgcttgga 960
gacgtttgcg gcaaggtcga gctaaccccc atggctattg ctgccggacg aaagctgtcc 1020
aaccggctgt ttggtcccac agagttcaag aaccagaagc aggactacac cgatgttcct 1080
tctgccgtct tttcccaccc cgaggttggc tccatcggta tcaccgaggc tgccgccaag 1140
gagcagtatg gcgaggagaa cgtcaaggtc tacacctcca agtttgtcgc catgtactac 1200
gccatgctcg aggagaaggc tcccaccgcc tacaagctgg tgtgtgccgg caaggacgag 1260
aaggttgttg gtctgcacat tgttggcgct gactctgccg agattctgca gggtttcggc 1320
gtggccattc gaatgggagc caccaaggcc gatttcgaca atgttgtggc tatccatccc 1380
acttctgccg aggagctggt gaccatgaga tag 1413

<210> SEQ ID NO 92
<211> LENGTH: 507
<212> TYPE: DNA
<213> ORGANISM: Yarrowia lipolytica
<220> FEATURE:

<223> OTHER INFORMATION: gene ylGPO

<400> SEQUENCE: 92

```
atgtccgccg agaaaaccaa taccgctttc tacaacctcg ctccactcga caagaacgga     60
gagcctttcc ccttcaagca gcttgagggc aaggtcgtgc tcatcgtgaa cgtcgcctcc    120
aagtgtggct ttactcccca atacaagggc cttgaggagg tctaccagaa gtacaaggat    180
cagggattca ccatcatcgg cttcccctgc aaccagtttg gtggccaaga gcctggttcc    240
gctgacgaga tctcctcctt ctgtcagctg aactacggcg tcactttccc cgttcttcag    300
aagatcaacg tcaacggcaa cgacgccgac cccgtctacg tctacctgaa ggagcagaag    360
gctggtctgc tgggcttccg aggaatcaag tggaactttg agaagttcct ggttgataag    420
cacggtaacg tcgtcgaccg atatgcttcc ctcaagaccc ccgccggcct cgaatccacc    480
atcgagaccc tcctcaaaaa gccctaa                                         507
```

<210> SEQ ID NO 93
<211> LENGTH: 828
<212> TYPE: DNA
<213> ORGANISM: artificial sequence
<220> FEATURE:
<223> OTHER INFORMATION: gene MaLCE

<400> SEQUENCE: 93

```
atggagtctg gacctatgcc tgccggaatt ccctttcccg agtactacga cttcttcatg     60
gactggaaga cccctcttgc tatcgctgcc acttacactg tggctgtggg cctgtttaac    120
cctaaggtgg gcaaggtgtc tagagtggtg gccaagtctg ccaatgctaa gcccgccgag    180
agaactcaat ctggagccgc catgaccgct tttgtgttcg tgcacaacct gatcctgtgc    240
gtgtactctg gcatcacctt ctaccacatg ttccccgcca tggtgaagaa cttccgaacc    300
cacactctgc acgaggccta ttgtgacacc gaccagtctc tgtggaacaa cgcccttggc    360
tattggggct acctgttcta cctgtctaag ttctacgagg tgatcgacac catcatcatc    420
atcctgaagg gccgacgatc ttctctgctg cagacctacc atcatgctgg agccatgatc    480
accatgtggt ctggcatcaa ctaccaggct acccccatct ggatcttcgt ggtgttcaac    540
tctttcatcc acaccatcat gtactgctac tacgccttca cctctatcgg ctttcatccc    600
cccggcaaaa agtacctgac ctctatgcag atcacccagt tcctggtggg cattaccatc    660
gccgtgtctt acctgtttgt gcccggctgc atcagaactc ctggcgccca aatggctgtg    720
tggatcaacg tgggctacct gttccctctg acctacctgt ttgtggactt cgccaagcga    780
acctactcta agcgaaccgc catcgccgct caaaaaaagg cccagtag                  828
```

<210> SEQ ID NO 94
<211> LENGTH: 1521
<212> TYPE: DNA
<213> ORGANISM: artificial sequence
<220> FEATURE:
<223> OTHER INFORMATION: gene AtFAE1

<400> SEQUENCE: 94

```
atgacctctg tgaacgtgaa gctgctgtac cgatacgtgc tgaccaactt cttcaacctg     60
tgcctgtttc ccctgactgc ctttcttgcc ggaaaagcct ctcgactgac catcaacgac    120
ctgcacaact tcctgtctta cctgcagcac aacctgatca ccgtgaccct gctgtttgcc    180
ttcaccgtgt tcggactggt gctgtacatt gtgacccgac ccaaccctgt gtatctggtg    240
gactactctt gttacctgcc ccccctcac cttaaagtgt ctgtgtctaa ggtgatggac    300
```

-continued

```
atcttctacc agatccgaaa ggccgacacc tcttctagaa acgtggcctg cgacgaccct    360
tcttctctgg acttcctgcg aaagatccag gagagatctg gcctgggcga cgaaacttac    420
tctcccgaag gcctgattca tgtgcctccc cgaaaaactt tcgccgcctc tagagaagag    480
accgagaagg tgattatcgg cgccctggag aacctgttcg agaacaccaa ggtgaacccc    540
cgagagatcg gcattctggt ggtgaactct tctatgttca accccacccc ctctctttct    600
gccatggtgg tgaacacctt caagctgcga tctaacatca agtctttcaa cctgggcggc    660
atgggatgtt ctgctggagt gatcgccatc gacctggcta aggacctgct gcacgtgcac    720
aagaacacct acgccctggt ggtgtctacc gagaacatca cccagggcat ctacgctggc    780
gagaaccgat ctatgatggt gtctaactgc ctgttcagag ttggaggagc cgccattctg    840
ctgtctaaca agtctggcga ccgacgacga tctaagtaca agctggtgca caccgtgcga    900
actcatactg gcgctgacga caagtctttc cgatgcgtgc agcaggagga tgatgagtct    960
ggcaagatcg gcgtgtgcct gtctaaggac atcaccaacg tggctggcac taccctgact   1020
aagaacatcg ccactctggg ccctctgatt ctgcctctgt ctgagaagtt cctgttcttc   1080
gccaccttcg tggccaagaa gctgctgaag gacaagatca agcactacta cgtgcccgac   1140
ttcaaacttg ccgtggacca cttttgcatc catgctggcg gcagagctgt tattgacgag   1200
ctggagaaga accttggcct gtctcccatt gatgtggagg cctctcgatc taccettcac   1260
cgattcggca acacctcttc ttcttctatc tggtacgagc tggcctacat cgaagccaag   1320
ggccgaatga agaagggcaa caaggcctgg caaattgctc tgggctctgg cttcaagtgc   1380
aactctgccg tgtgggtggc tctgagaaac gtgaaggcct ctgccaattc tccttggcag   1440
cactgcattg accgataccc cgtgaagatc gactctgacc tgtctaagtc taagacccac   1500
gtgcagaacg gccgatctta a                                             1521
```

<210> SEQ ID NO 95
<211> LENGTH: 1521
<212> TYPE: DNA
<213> ORGANISM: artificial sequence
<220> FEATURE:
<223> OTHER INFORMATION: gene BtFAE1

<400> SEQUENCE: 95

```
atgacctctg tgaacgtgaa gctgatctac cactacgtga tcaccaacct gttcaacctg     60
tgcttcttcc ccctgactgc tatcgttgcc ggcaaagctt ctcgactgac cattgacgac    120
ctgcaccacc tgtactactc ttacctgcag cacaacctga ttaccatcgc ccccctgttt    180
gcctttaccg tgttcggctc tgtgctgtac attgccaccc gacctaagcc tgtgtacctg    240
gtggagtact cttgttacct gccccccact cactgtcgat cttctatctc taaggtgatg    300
gacatcttct accaggtgcg aaaggccgac ccctctagaa atggcacctg cgacgactct    360
tcttggctgg acttcctgcg aaagatccag gagcgatctg gcctgggaga tgagactcat    420
ggccctgagg gactgcttca cgtgcctccc agaaaaacct ttgccgccgc tagagaagaa    480
accgagaagg tgattatcgg cgccctggag aacctgttcg agaacaccaa ggtgaacccc    540
aaggacatcg gcatcctggt ggtgaactct tctatgttca accccacccc ctctctttct    600
gccatggtgg tgaacacctt caagctgcga tctaacgtgc gatctttcaa cctgggaggc    660
atgggatgtt ctgctggcgt gatcgctatt gacctggcca aagacctgct gcacgtgcac    720
aagaacacct acgccctggt ggtgtctacc gagaacatca cctacaacat ctacgccggc    780
```

-continued

```
gacaacaagt ctatgatggt gtctaactgc ctgttccgag tgggaggagc cgctattctg    840

ctgtctaaca agccccgaga ccgacgacga tctaagtacg agctggtgca caccgtgcga    900

actcataccg gagctgacga caagtctttc cgatgcgtgc aacagggcga tgacgagtct    960

ggaaagaccg gcgtgtctct gtctaaggac atcaccgacg tggctggaag aaccgtgaag   1020

aagaacatct ctaccctggg ccctctgatt ctgcctctgt ctgagaagct gctgttcttc   1080

gtgaccttca tgggcaagaa gctgttcaag gacaagatca agcactacta cgtgcccgac   1140

ttcaagcttg ccatcgacca cttctgtatc cacgctggcg gacgagctgt gattgatgtg   1200

ctggagaaga accttggact ggcccctatt gatgtggagg cctctcgatc tacccttcac   1260

cgattcggca acacctcttc ttcttctatc tggtacgagc tggcctacat cgaagctaag   1320

ggccgaatga agaagggcaa caaggtgtgg caaatcgctc tgggctctgg cttcaagtgc   1380

aactctgccg tttgggtggc cctgagaaat gtgaaggcct ctcgaaagtc tccttgggag   1440

cactgcattg accgataccc cgtgaagatc gactacgact ctgccaagtc tgaggtgaga   1500

gtgcagaacg gccgatctta a                                             1521
```

<210> SEQ ID NO 96
<211> LENGTH: 1521
<212> TYPE: DNA
<213> ORGANISM: artificial sequence
<220> FEATURE:
<223> OTHER INFORMATION: gene CgKCS

<400> SEQUENCE: 96

```
atgacctcta tcaacgtgaa gctgctgtac cactacgtgc tgaccaactt cttcaacctg     60

tgcctgttcc ccctgactgc ttttcctgcc ggcaaggctt ctcaactgac caccaacgac    120

ctgcaccacc tgtactctta cctgcaccac aacctgatca ccgtgaccct gctgtttgcc    180

ttcaccgtgt tcggctctat cctgtacatc gtgaccagac ccaagcctgt gtacctggtg    240

gactactctt gttacctgcc ccccagacat ctgtcttgcg gcatctctcg agtgatggag    300

atcttctacg agatccgaaa gtctgacccc tctcgagagg tgcctttcga cgacccttct    360

tctctggagt tcctgcgaaa gatccaggag cgatctggac tgggagacga gacttatgga    420

ccccagggac tggttcatga tatgcccctg cgaatgaatt ttgccgccgc ccgagaagaa    480

actgagcagg tgatcaacgg agccctggag aagctgttcg agaacaccaa ggtgaacccc    540

cgagagattg gcatcctggt ggtgaactct tctatgttca accccacccc ctctctttct    600

gccatggtgg tgaacacctt caagctgcga tctaacatca agtctttctc tctgggcggc    660

atgggatgtt ctgccggcat catcgctatc gacctggcta aggacctgct gcacgtgcac    720

aagaacacct acgccctggt ggtgtctacc gagaacatca cccactctac ctacaccggc    780

gacaaccgat ctatgatggt gtctaactgc ctgttcagaa tgggcggagc cgccattctg    840

ctgtctaaca aggctggcga ccgacgacga tctaagtaca agctggccca cactgtgaga    900

actcacaccg gcgctgacga tcagtctttc cgatgcgtgc gacaggagga tgatgacaga    960

ggcaagatcg gcgtgtgcct gtctaaagac atcaccgccg tggccggaaa aaccgtgacc   1020

aagaacatcg ctaccctggg acctcttgtg ctgcctctgt ctgagaagtt cctgtacgtg   1080

gtgtctctga tggccaagaa gctgttcaag aacaagatca agcacaccta cgtgcccgat   1140

ttcaagctgg ccatcgacca cttctgcatc catgctggcg gaagagctgt gattgacgtg   1200

ctggagaaga acctggccct gtctcctgtg gatgtggagg cttctcgatc taccctgcac   1260

cgattcggca acacctcttc ttcttctatc tggtacgagc tggcctacat cgaagccaag   1320
```

ggccgaatga agaagggcaa caaggtgtgg caaatcgcca tcggctctgg cttcaagtgc 1380
aactctgccg tttgggtggc cctgtgtaat gtgaagccct ctgtgaactc tccttgggag 1440
cactgcattg acagataccc cgtggagatc aactacggct cttctaagtc tgagacccga 1500
gcccaaaacg gccgatctta a 1521

<210> SEQ ID NO 97
<211> LENGTH: 804
<212> TYPE: DNA
<213> ORGANISM: artificial sequence
<220> FEATURE:
<223> OTHER INFORMATION: gene rELO2

<400> SEQUENCE: 97
atgaacatgt ctgtgctgac cctgcaggag tacgagttcg agaagcagtt caacgagaac 60
gaggccattc agtggatgca ggagaactgg aagaagtcct tcctgttctc cgccctgtac 120
gccgccttca ttttcggcgg ccgacacctg atgaacaagc gagccaagtt cgagctgcga 180
aagcccctgg tcctgtggtc tctgaccctg gccgtcttct ctatcttcgg tgccctgcga 240
accggtgcct acatgctgta cattctgatg accaagggcc tgaagcagtc cgtctgtgac 300
cagtccttct acaacggtcc cgtctctaag ttctgggcct acgccttcgt cctgtccaag 360
gcccccgagc tgggtgacac cattttcatc attctgcgaa agcagaagct gattttcctg 420
cactggtacc accacattac cgtcctgctg tactcctggt actcctacaa ggacatggtc 480
gccggcggtg gctggttcat gaccatgaac tacggcgtgc acgccgtcat gtactcctac 540
tacgccctgc gagccgccgg cttccgagtc tctcgaaagt tcgccatgtt cattaccctg 600
tctcagatta cccagatgct gatgggttgt gtcatcaact acctggtctt caactggatg 660
cagcacgaca acgaccagtg ttactcccac ttccagaaca ttttctggtc ctccctgatg 720
tacctgtctt acctgctgct gttctgccac ttcttcttcg aggcctacat tggtaaagtg 780
aagaaggcca ccaaggccga gtaa 804

<210> SEQ ID NO 98
<211> LENGTH: 972
<212> TYPE: DNA
<213> ORGANISM: artificial sequence
<220> FEATURE:
<223> OTHER INFORMATION: gene CpLCE

<400> SEQUENCE: 98
atgatcatca agaacaacaa caacggctac ttcattgaca acgtcaacaa gatctgggag 60
atccccatca actctgagca catggacatc ctgaaggaga tcccctggtt caagtacctg 120
accctgccca ttgagcgaaa ctggaacggc atgaagctgt tcctgtggac caacgacaac 180
tactacctgg cccacaccat ctgcatcatc tacgccttct tcatctactt cggtcccaag 240
atcatggaga agcgaaagcc cttcaagctg gagaagcccc tgaagtactg gaacctgttc 300
ctggccctgt tctctttcat cggcaccctg cgactgatgc cctacgtgct gaccaacctg 360
attaagtacg gcttcgtctc ttctatctgc tcccccccca ttgccccccct gaccaagggc 420 cctgccggcc tgtggctgtc tctgttcatc tattccaagt acattgagct gatcgacacc 480
ttcttcatca ttgcccgaaa gaagtctctg tccttcctgc actggttcca ccacctgacc 540
gtgctgctgt acacctggga cgcctacgtc tgttgtcaga ccattggtgt cttcttctgt 600
gccattaact acttcgtgca ctccatcatg tacttctact actacctgtc ctcctgtggc 660

-continued

```
aagcgaccca agtggggtat gatcattacc attctgcaga tcgtccagat gattattggc    720

accattctga ccacctccgg tatgtactac tcttacaagc accccttcgc caacgtgttc    780

cccgtcgagt acctgtccca gcccctgaag gtcggttgcc acttcatccg aaccaacggt    840

gtcttcgcct gcctgatgta catctcttac ttcgccctgt tcttcgactt cttcatcaag    900

cgatacatca ccaagggcac ccccctggcc gagtgggtca ccgctaacaa gaagcccacc    960

aagcgagact aa                                                        972
```

<210> SEQ ID NO 99
<211> LENGTH: 795
<212> TYPE: DNA
<213> ORGANISM: artificial sequence
<220> FEATURE:
<223> OTHER INFORMATION: gene gELOVL6

<400> SEQUENCE: 99

```
atgtctgtgc tgaccctgca ggagtacgag ttcgagaagc agttcaacga gaacgaggcc     60

atccagtgga tgcaggagaa ctggaagaag tctttcctgt tctctgccct gtacgccgcc    120

ttcgtcttcg gcggccgaca cctgatgaac aagcgagcca agttcgagct gcgaaagccc    180

ctggtgctgt ggtctctgac cctggccgtg ttctccattt tcggcgccct gcgaaccggc    240

gcctacatgg tctacaccgt gatgaccaag ggcctgaagc actccgtctg tgaccagggc    300

ttctacaacg gccccgtctc caagttctgg gcctacgcct tcgtcctgtc taaggccccc    360

gagctgggtg acaccatctt cattatcctg cgaaagcaga agctgatttt cctgcactgg    420

taccaccaca ttaccgtcct gctgtactcc tggtactcct acaaggacat ggtggccggc    480

ggtggttggt tcatgaccat gaactactct gtgcactctg tgatgtactc ctactacgcc    540

ctgcgagccg ccggcttccg agtctctcga aagttcgcca tgttcatcac cctgtcccag    600

attctgcaga tgctggtggg ctgtgtcatt aactacctgg tgttccagtg gatgcagcac    660

gaccagtgcc actcccactt ccagaacatc ttctggtcct ctctgatgta cctgtcctac    720

ttcgtcctgt tctgccactt cttcttcgag gcctacatcg gctctaagat gcgaaaggcc    780

accaaggccg actaa                                                     795
```

<210> SEQ ID NO 100
<211> LENGTH: 1434
<212> TYPE: DNA
<213> ORGANISM: artificial sequence
<220> FEATURE:
<223> OTHER INFORMATION: gene D9DMB

<400> SEQUENCE: 100

```
atgtcctccg tggtcgagac ctgtaagacc ctgcccgtgc aggcctctcg actggtgccc     60

accgccgtca aggaggaggt ccccaccgac cacaacgtcc ccgacaacta cgtgtcctgg    120

accctgaaga accagaagcc cctgcccccc atcgtgctgg ccaacctgct gcagaacatc    180

gagtggctga ccttcatcat tctgaccatc accccctcca tcgccatcta cggtctgttc    240

accgtcaaca tgcagtggaa gaccttcgtg tggtctgtca tgtactactt catcaccggc    300

ctgggcatca ccgccggcta ccaccgactg tggtctcacc gatcctacaa cgcctctaag    360

cccctgcagt acttcctggc cgtcgccggc accggtgccg ttgagggttc catcaagtgg    420

tggtgccgaa agcaccgagc ccaccaccga tacaccgaca ccgacctgga cccctacaac    480

gccaacaagg gtttcttctt ctcccacgtg ggctggatgc tggtcaagcc ccgagacaag    540

cccggtgtgg ccgacatttc tgacctgcga aagtccgagg tcattcagtg gcagcaccga    600
```

```
tggtacgtgt ggctgattgt gggtgccggt ctgctgctgc ccaccgtggt cgctggtctg    660

ggctggggag actgggccgg tggtttcttc tttgccggtg ccgcccgact gaccttcgtg    720

caccactcta ccttctgtgt caactctctg gcccactggc tgggtgagac cccctttcgac   780

gacaagcact ctccccgaga ccacttcatt accgccctgg tcaccgtggg cgagggctac    840

cacaacttcc accaccagtt ccccatggac taccgaaacg ccattcgatg gtaccagtac    900

gaccccacca agtggttcat ttggatgtgc tccaagttcg gcctggcctc tcacctgaag    960

gtcttccccg agaacgaggt gcgaaagggc gagctgacca tgcagctgaa gaagctgcga   1020

gagacccagg acgtgctgac ctgggccccc gacgtggagg gactgcctgt gatttcttgg   1080

gagtccttct ctgagcagtc cgtcacccga cccctgatca tcgtcgccgg cttcatccac   1140

gacgtctctg acttcatcga cgagcacccc ggtggccgac acctgattat taagtacatt   1200

ggtaaagacg ccaccccgc cttcttcggc ggcgtttacg accactccaa cgccgcccac    1260

aacctgctgt ccatgaagcg agtcggtgcc ctgcacggcg gcatccagca cggactgcag   1320

gacatgtcta ttcccccgc ccagcgactg cgaatcgccc gatacaacga gctggccggc    1380

tctccctaca actcctctac cgccacctct gactctgagg gtattctggg ttaa         1434
```

<210> SEQ ID NO 101
<211> LENGTH: 1020
<212> TYPE: DNA
<213> ORGANISM: artificial sequence
<220> FEATURE:
<223> OTHER INFORMATION: gene CeFAT6

<400> SEQUENCE: 101

```
atgaccgtca agacccgatc caacattgcc aagaagatcg agaaggacgg tggccccgag     60

acccagtacc tggccgtgga ccccaacgag atcattcagc tgcaggagga gtctaagaag    120

atcccctaca agatggagat cgtctggcga aacgtggccc tgttcgccgc cctgcacttc    180

gccgctgcca tcggactgta ccagctgatt ttcgaggcca agtggcagac cgtgattttc    240

accttcctgc tgtacgtctt cggtggtttc ggcattaccg ccggtgccca ccgactgtgg    300

tctcacaagt cctacaaggc caccaccccc atgcgaattt tcctgatgat cctgaacaac    360

attgccctgc agaacgacgt cattgagtgg gcccgagacc accgatgtca ccacaagtgg    420

accgacaccg acgccgaccc ccacaacacc acccgaggtt tcttcttcgc ccacatgggc    480

tggctgctgg tgcgaaagca cccccaggtg aaggagcagg gtgccaagct ggacatgtcc    540

gacctgctgt ctgaccccgt cctggtgttc cagcgaaagc actacttccc cctggtcatc    600

ctgtgttgtt tcattctgcc caccattatc cccgtctact tctggaagga gaccgccttc    660

atcgccttct acaccgccgg taccttccga tactgcttca ccctgcacgc cacctggtgt    720

atcaactccg ccgcccacta cttcggttgg aagccctacg actcctccat tacccccgtg    780

gagaacgtgt tcaccaccat cgccgccgtc ggcgagggcg gtcataactt ccaccacacc    840

ttcccccagg actaccgaac ctccgagtac tctctgaagt acaactggac ccgagtgctg    900

atcgacaccg ccgccgccct gggactggtg tacgaccgaa agaccgcctg tgacgagatc    960

atcggccgac aggtgtctaa ccacggctgt gacatccagc gaggtaaatc tattatgtaa   1020
```

<210> SEQ ID NO 102
<211> LENGTH: 1338
<212> TYPE: DNA
<213> ORGANISM: artificial sequence
<220> FEATURE:

-continued

<223> OTHER INFORMATION: gene MaOLE2

<400> SEQUENCE: 102
atggccaccc ccctgcctcc taccttcacc gtgcccgcct cctccaccga gacccgacga 60
gaccccctgc cccacgacgt gctgcctcct ctgttcaacg gtgagaaggt caacatcctg 120
aacatttgga agtacctgga ctggaagcac gtcatcggcc tgctggtgac ccccctggtc 180
gccctttacg gtatgtgtac caccgagctg cacaccaaga ccctggtctg gtccatcgtg 240
tactacttcg ccaccggcct gggtatcacc gccggttacc accgactgtg ggcccaccga 300
gcctacaacg ccggtcccgc tatgtccttc gccctggccc tgttcggcgc cggagctgtt 360
gagggctcta tcaagtggtg gtcccgaggc caccgagccc accaccgatg gaccgacacc 420
gagaaggacc cctactccgc ccaccgaggt gtgttctact ctcacctggg ttggctgctg 480
atcaagcgac ccggttggaa gattggtcac gccgacgtcg acgacctgaa caagaacccc 540
ctggtccagt ggcagcacaa gcactacctg atcctggtca ttctgatggg tctggtgttc 600
cccaccgccg tcgccggtct gggatggggt gactggcgag gtggctactt ctacgccgcc 660
attctgcgac tgatcttcgt gcaccacgcc accttctgcg tgaactctct ggcccactgg 720
ctgggcgacg gccctttcga cgaccgacac accccccgag accacttcat caccgccttc 780
ctgaccctgg gcgagggtta ccacaacttc caccaccagt tcccccagga ctaccgatcc 840
gccatccgat tctaccagta cgaccccacc aagtggctga ttgccacctg cgccttcttc 900
ggtttcgcct ctcacctgaa gaccttcccc gagaacgaga ttaagaaggg caagctgcag 960
atgattgaga aggaggtgct ggagaagaag accaagctgc agtggggtac ccccatcgcc 1020
gacctgccca tcctgtcctt cgaggacttc cagcacgcct gcaagaacga ccgaaagcag 1080
tggatcctgc tggagggcgt cgtctacgac gtcgccgact tcatgaccga gcaccccggt 1140
ggcgagaagt acatcaagat gggcgtgggt aaagacatga cctccgcctt caacggcggt 1200
atgtacgacc actctaacgc cgcccgaaac ctgctgtctc tgatgcgagt cgccgtcgtc 1260
gagttcggtg gcgaggtcga ggcccagaag tcccgaccct ctgtgaccgt gtacggcgac 1320
cactctaagg aggagtaa 1338

<210> SEQ ID NO 103
<211> LENGTH: 918
<212> TYPE: DNA
<213> ORGANISM: artificial sequence
<220> FEATURE:
<223> OTHER INFORMATION: gene AtADS1

<400> SEQUENCE: 103
atgtctctgt ctgcctctga gaaggaggag aacaacaaga agatggccgc cgacaaggcc 60
gagatgggtc gaaagaagcg agccatgtgg gagcgaaagt ggaagcgact ggacattgtg 120
aaggccttcg cctccctgtt cgtccacttc ctgtgtctgc tggcccccttt caacttcacc 180 tggcccgccc tgcgagtggc cctgattgtg tacaccgtgg gtggcctggg catcaccgtg 240
tcttaccacc gaaacctggc ccaccgatcc ttcaaggtcc ccaagtggct ggagtacttc 300
ttcgcctact gcggcctgct ggccattcag ggcgacccca ttgactgggt gtctacccac 360
cgataccacc accagttcac cgactccgac cgagaccccc actcccccaa cgagggtttc 420
tggttctctc acctgctgtg gctgttcgac accggctacc tggtcgagaa gtgcggccga 480
cgaaccaacg tcgaggacct gaagcgacag tggtactaca agttcctgca gcgaaccgtc 540
ctgtaccaca ttctgacctt cggtttcctg ctgtactact tcggtggtct gtctttcctg 600

-continued acctggggta tgggtattgg tgtcgccatg gagcaccacg tcacctgcct gattaactct 660
ctgtgtcacg tgtggggttc tcgaacctgg aagaccaacg acacctcccg aaacgtgtgg 720
tggctgtccg tgttctcttt cggcgagtcc tggcacaaca accaccacgc cttcgagtcc 780
tccgcccgac agggtctgga gtggtggcag attgacatct cttggtacat tgtccgattc 840
ctggagatca tcggcctggc caccgacgtg aagctgccct ccgagtctca gcgacgacga 900
atggccatgg tccgataa 918

<210> SEQ ID NO 104
<211> LENGTH: 924
<212> TYPE: DNA
<213> ORGANISM: artificial sequence
<220> FEATURE:
<223> OTHER INFORMATION: gene AtADS2

<400> SEQUENCE: 104
atgtctgtga cctctaccgt ggaggagaac caccagaaga acccctctac ccctgctgct 60
gtggaggaaa agaagaagcg acgatgggtg ttctgggatc gacgatggcg acgactggac 120
tacgtgaagt tctctgcctc tttcaccgtg cactctctgg ctcttcttgc ccccttctac 180
ttcacttggt ctgccctgtg ggtgaccttc ctgttctaca ccattggcgg cctgggcatt 240
actgtgtctt accaccgaaa cctggcccac cgatctttca aggtgcccaa gtggctggaa 300
tacctgctgg cttattgtgc cctgctggcc attcaaggtg accctatcga ctgggtgtct 360
acccaccgat accaccacca gttcaccgac tctgaacgag atccccactc tcctaaagag 420
ggcttctggt tctctcacct gctgtggatc tacgactctg cctacctggt gtctaaatgc 480
ggccgacgag ccaatgtgga ggatctgaag cgacagtggt tctaccgatt cctgcagaag 540
accgtgctgt tccacattct tggcctgggc ttcttcctgt tttacctggg cggcatgtct 600
tttgtgacct ggggaatggg agtgggagct gccctggaag ttcatgtgac ctgcctgatc 660
aactctctgt gccacatctg ggggaacccga acctggaaaa ccaacgacac ctctcgaaac 720
gtgtggtggc tgtctgtgtt ctctttcggc gagtcttggc acaacaacca ccacgccttc 780
gagtcttctg ctcgacaggg actggaatgg tggcagatcg acatctcttg gtacatcgtg 840
cgattcttcg agatcatcgg cctggccacc gatgttaaag tgcccaccga agcccaacga 900
agacgaatgg ccatcgtgag atga 924

<210> SEQ ID NO 105
<211> LENGTH: 1488
<212> TYPE: DNA
<213> ORGANISM: artificial sequence
<220> FEATURE:
<223> OTHER INFORMATION: gene EcAldH

<400> SEQUENCE: 105
atgaacttcc accacttggc ttactggcaa gacaaggctt tgtctttggc tatcgaaaac 60
agattgttca tcaacggtga atacactgct gctgctgaaa acgaaacttt cgaaactgtt 120
gacccagtta ctcaagctcc attggctaag atcgctagag gtaagtctgt tgacatcgac 180
agagctatgt ctgctgctag aggtgttttc gaaagaggtg actggtcttt gtcttctcca 240
gctaagagaa aggctgtttt gaacaagttg gctgacttga tggaagctca cgctgaagaa 300
ttggctttgt tggaaacttt ggacactggt aagccaatca gacactcttt gagagacgac 360
atcccaggtg ctgctagagc tatcagatgg tacgctgaag ctatcgacaa ggtttacggt 420
gaagttgcta ctacttcttc tcacgaattg gctatgatcg ttagagaacc agttggtgtt 480
atcgctgcta tcgttccatg gaacttccca ttgttgttga cttgttggaa gttgggtcca 540
gctttggctg ctggtaactc tgttatcttg aagccatctg aaaagtctcc attgtctgct 600
atcagattgg ctggtttggc taaggaagct ggtttgccag acggtgtttt gaacgttgtt 660
actggtttcg gtcacgaagc tggtcaagct ttgtctagac acaacgacat cgacgctatc 720
gctttcactg gttctactag aactggtaag caattgttga aggacgctgg tgactctaac 780
atgaagagag tttggttgga agctggtggt aagtctgcta acatcgtttt cgctgactgt 840
ccagacttgc aacaagctgc ttctgctact gctgctggta tcttctacaa ccaaggtcaa 900
gtttgtatcg ctggtactag attgttgttg gaagaatcta tcgctgacga attcttggct 960
ttgttgaagc aacaagctca aaactggcaa ccaggtcacc cattggaccc agctactact 1020
atgggtactt tgatcgactg tgctcacgct gactctgttc actctttcat cagagaaggt 1080
gaatctaagg gtcaattgtt gttggacggt agaaacgctg gtttggctgc tgctatcggt 1140
ccaactatct tcgttgacgt tgacccaaac gcttctttgt ctagagaaga aatcttcggt 1200
ccagttttgg ttgttactag attcacttct gaagaacaag ctttgcaatt ggctaacgac 1260
tctcaatacg gtttgggtgc tgctgtttgg actagagact tgtctagagc tcacagaatg 1320
tctagaagat tgaaggctgg ttctgttttc gttaacaact acaacgacgg tgacatgact 1380
gttccattcg gtggttacaa gcaatctggt aacggtagag acaagtcttt gcacgctttg 1440
gaaaagttca ctgaattgaa gactatctgg atctctttgg aagcttaa 1488

<210> SEQ ID NO 106
<211> LENGTH: 1518
<212> TYPE: DNA
<213> ORGANISM: artificial sequence
<220> FEATURE:
<223> OTHER INFORMATION: gene ScZwf

<400> SEQUENCE: 106
atgagtgaag gccccgtcaa attcgaaaaa aataccgtca tatctgtctt tggtgcgtca 60
ggtgatctgg caaagaagaa gacttttccc gccttatttg ggcttttcag agaaggttac 120
cttgatccat ctaccaagat cttcggttat gcccggtcca aattgtccat ggaggaggac 180
ctgaagtccc gtgtcctacc ccacttgaaa aaacctcacg gtgaagccga tgactctaag 240
gtcgaacagt tcttcaagat ggtcagctac atttcgggaa attacgacac agatgaaggc 300
ttcgacgaat taagaacgca gatcgagaaa ttcgagaaaa gtgccaacgt cgatgtccca 360
caccgtctct tctatctggc cttgccgcca agcgtttttt tgacggtggc caagcagatc 420
aagagtcgtg tgtacgcaga gaatggcatc acccgtgtaa tcgtagagaa acctttcggc 480
cacgacctgg cctctgccag ggagctgcaa aaaaacctgg ggcccctctt taaagaagaa 540
gagttgtaca gaattgacca ttacttgggt aaagagttgg tcaagaatct tttagtcttg 600
aggttcggta accagttttt gaatgcctcg tggaatagag acaacattca aagcgttcag 660
atttcgttta aagagaggtt cggcaccgaa ggccgtggcg gctatttcga ctctataggc 720
ataatcagag acgtgatgca gaaccatctg ttacaaatca tgactctctt gactatggaa 780
agaccggtgt cttttgaccc ggaatctatt cgtgacgaaa aggttaaggt tctaaaggcc 840
gtggccccca tcgacacgga cgacgtcctc ttgggccagt acggtaaatc tgaggacggg 900
tctaagcccg cctacgtgga tgatgacact gtagacaagg actctaaatg tgtcactttt 960
gcagcaatga ctttcaacat cgaaaacgag cgttgggagg gcgtccccat catgatgcgt 1020
gccggtaagg ctttgaatga gtccaaggtg gagatcagac tgcagtacaa agcggtcgca 1080
tcgggtgtct tcaaagacat tccaaataac gaactggtca tcagagtgca gcccgatgcc 1140
gctgtgtacc taaagtttaa tgctaagacc cctggtctgt caaatgctac ccaagtcaca 1200
gatctgaatc taacttacgc aagcaggtac caagactttt ggattccaga ggcttacgag 1260
gtgttgataa gagacgccct actgggtgac cattccaact ttgtcagaga tgacgaattg 1320
gatatcagtt ggggcatatt caccccatta ctgaagcaca tagagcgtcc ggacggtcca 1380
acaccggaaa tttaccccta cggatcaaga ggtccaaagg gattgaagga atatatgcaa 1440
aaacacaagt atgttatgcc cgaaaagcac ccttacgctt ggcccgtgac taagccagaa 1500
gatacgaagg ataattag 1518

<210> SEQ ID NO 107
<211> LENGTH: 1130
<212> TYPE: DNA
<213> ORGANISM: Yarrowia lipolytica
<220> FEATURE:
<223> OTHER INFORMATION: promoter gene GPAT

<400> SEQUENCE: 107
caacttttct tgtcgacctg agataccgag gttgcgcagg ggatcaactt ttgtgtctca 60
gagggaccca agtgcgtacg gagagtacag tacatactgt agctaacggt agcaggcgaa 120
ctactggtac atacctcccc cggaatatgt acaggcataa tgcgtatctg tgggacatgt 180
ggtcgttgcg ccattatgta agcagcgtgt actcctctga ctgtccatat ggtttgctcc 240
atctcaccct catcgttttc attgttcaca ggcggccaca aaaaaactgt cttctctcct 300
tctctcttcg ccttagtcta ctcggaccag ttttagttta gcttggcgcc actggataaa 360
tgagacctca ggccttgtga tgaggaggtc acttatgaag catgttagga ggtgcttgta 420
tggatagaga agcacccaaa ataataagaa taataataaa acagggggcg ttgtcatttc 480
atatcgtgtt ttcaccatca atacacctcc aaacaatgcc cttcatgtgg ccagccccaa 540
tattgtcctg tagttcaact ctatgcagct cgtatcttat tgagcaagta aaactctgtc 600
agccgatatt gcccgacccg cgacaagggt caacaaggtg gtgtaaggcc ttcgcagaag 660
tcaaaactgt gccaaacaaa catctagagt ctctttggtg tttctcgcat atatttaatc 720
ggctgtctta cgtatttggc ctcggtaccg gactaatttc ggatcatccc caatacgctt 780
tttcttcgca gctgtcaaca gtgtccatga tctatccacc taaatgggtc atatgaggcg 840
tataatttcg tggtgctgat aataattccc atatatttga cacaaaactt cccccccctag 900 acatacatct cacaatctca cttcttgtgc ttctgtcaca catctcctcc agctgacttc 960
aactcacacc tctgccccag ttggtctaca gcggtataag gtttctctgc atagaggtgc 1020
accactcctc ccgatacttg tttgtgtgac ttgtgggtca cgacatatat atctacacac 1080
attgcgccac cctttggttc ttccagcaca acaaaaacac gacacgctaa 1130

<210> SEQ ID NO 108
<211> LENGTH: 522
<212> TYPE: DNA
<213> ORGANISM: Yarrowia lipolytica
<220> FEATURE:
<223> OTHER INFORMATION: promoter gene TEF1

<400> SEQUENCE: 108
agagaccggg ttggcggcgc atttgtgtcc caaaaaacag ccccaattgc cccaattgac 60

-continued

```
cccaaattga cccagtagcg ggcccaaccc cggcgagagc ccccttctcc ccacatatca    120

aacctccccc ggttcccaca cttgccgtta agggcgtagg gtactgcagt ctggaatcta    180

cgcttgttca gactttgtac tagtttcttt gtctggccat ccgggtaacc catgccggac    240

gcaaaataga ctactgaaaa ttttttttgct ttgtggttgg gactttagcc aagggtataa   300

aagaccaccg tccccgaatt acctttcctc ttcttttctc tctctccttg tcaactcaca    360

cccgaaatcg ttaagcattt ccttctgagt ataagaatca ttcaaaatgg tgagtttcag    420

aggcagcagc aattgccacg ggctttgagc acacggccgg gtgtggtccc attcccatcg    480

acacaagacg ccacgtcatc cgaccagcac tttttgcagt ac                       522
```

<210> SEQ ID NO 109
<211> LENGTH: 1002
<212> TYPE: DNA
<213> ORGANISM: Yarrowia lipolytica
<220> FEATURE:
<223> OTHER INFORMATION: promoter gene EXP1

<400> SEQUENCE: 109

```
aaggagtttg gcgcccgttt tttcgagccc cacacgtttc ggtgagtatg agcggcggca     60

gattcgagcg tttccggttt ccgcggctgg acgagagccc atgatggggg ctcccaccac    120

cagcaatcag ggccctgatt acacacccac ctgtaatgtc atgctgttca tcgtggttaa    180

tgctgctgtg tgctgtgtgt gtgtgttgtt tggcgctcat tgttgcgtta tgcagcgtac    240

accacaatat tggaagctta ttagcctttc tattttttcg tttgcaaggc ttaacaacat    300

tgctgtggag agggatgggg atatggaggc cgctggaggg agtcggagag gcgttttgga    360

gcggcttggc ctggcgccca gctcgcgaaa cgcacctagg acccttttggc acgccgaaat   420

gtgccacttt tcagtctagt aacgccttac ctacgtcatt ccatgcatgc atgtttgcgc    480

ctttttttccc ttgcccttga tcgccacaca gtacagtgca ctgtacagtg gaggttttgg   540

gggggtctta gatgggagct aaaagcggcc tagcggtaca ctagtgggat tgtatggagt    600

ggcatggagc ctaggtggag cctgacagga cgcacgaccg gctagcccgt gacagacgat    660

gggtggctcc tgttgtccac cgcgtacaaa tgtttgggcc aaagtcttgt cagccttgct    720

tgcgaaccta attcccaatt ttgtcacttc gcacccccat tgatcgagcc ctaacccctg    780

cccatcaggc aatccaatta agctcgcatt gtctgccttg tttagtttgg ctcctgcccg    840

tttcggcgtc cacttgcaca aacacaaaca agcattatat ataaggctcg tctctccctc    900

ccaaccacac tcactttttt gcccgtcttc ccttgctaac acaaaagtca agaacacaaa    960

caaccacccc aacccccctta cacacaagac atatctacag ca                      1002
```

<210> SEQ ID NO 110
<211> LENGTH: 438
<212> TYPE: DNA
<213> ORGANISM: Yarrowia lipolytica
<220> FEATURE:
<223> OTHER INFORMATION: promoter gene EYK1

<400> SEQUENCE: 110

```
tttgtgcaag tgtgtgtgtg tgtgtgtgtg tggtgtgttt gtgtgttaga acggatgttc     60

tggtgagtgt gagtgtgtag ttgtgtgatg agaccttggt gccaccccaa ggtatatata    120

tataacacct ccaggagctc taaaaaggca tctacttttc tctatactgt acgtttcaat    180

ctggggaagc ggaatcccaa aagggaaagc cgccgcatta agctccacag ccttgcataa    240

tccgatgacc tgactagtgc ggacaaagac tattatttcg aggcaaggcc accacgtacc    300
```

gcggtcccaa acttttgcaa agctgaaaac agcgtggggg tcaacgtgga tcagaaagag 360
gggcagatca gcttctataa gaagctcctt tccccacaat tggcccacac gacacttcta 420
cacacttaca catctact 438

<210> SEQ ID NO 111
<211> LENGTH: 931
<212> TYPE: DNA
<213> ORGANISM: Yarrowia lipolytica
<220> FEATURE:
<223> OTHER INFORMATION: promoter gene GPD

<400> SEQUENCE: 111
cgcagtagga tgtcctgcac gggtcttttt gtggggtgtg gagaaagggg tgcttggaga 60
tggaagccgg tagaaccggg ctgcttgggg ggatttgggg ccgctgggct ccaaagaggg 120
gtaggcattt cgttggggtt acgtaattgc ggcatttggg tcctgcgcgc atgtcccatt 180
ggtcagaatt agtccggata ggagacttat cagccaatca cagcgccgga tccacctgta 240
ggttgggttg ggtgggagca cccctccaca gagtagagtc aaacagcagc agcaacatga 300
tagttggggg tgtgcgtgtt aaaggaaaaa aaaagaagct tgggttatat tcccgctcta 360
tttagaggtt gcgggataga cgccgacgga gggcaatggc gccatggaac cttgcggata 420
tcgatacgcc gcggcggact gcgtccgaac cagctccagc agcgtttttt ccgggccatt 480
gagccgactg cgaccccgcc aacgtgtctt ggcccacgca ctcatgtcat gttggtgttg 540
ggaggccact ttttaagtag cacaaggcac ctagctcgca gcaaggtgtc cgaaccaaag 600
aagcggctgc agtggtgcaa acggggcgga aacggcggga aaaagccacg ggggcacgaa 660
ttgaggcacg ccctcgaatt tgagacgagt cacggcccca ttcgcccgcg caatggctcg 720
ccaacgcccg gtcttttgca ccacatcagg ttaccccaag ccaaaccttt gtgttaaaaa 780
gcttaacata ttataccgaa cgtaggtttg ggcgggcttg ctccgtctgt ccaaggcaac 840
atttatataa gggtctgcat cgccggctca attgaatctt ttttcttctt ctcttctcta 900
tattcattct tgaattaaac acacatcaac a 931

<210> SEQ ID NO 112
<211> LENGTH: 407
<212> TYPE: DNA
<213> ORGANISM: Yarrowia lipolytica
<220> FEATURE:
<223> OTHER INFORMATION: terminator sequence XPR2

<400> SEQUENCE: 112
ccccacgttg ccggtcttgc ctcctactac ctgtccatca atgacgaggt tctcacccct 60
gcccaggtcg aggctcttat tactgagtcc aacaccggtg ttcttcccac caccaacctc 120
aagggctctc ccaacgctgt tgcctacaac ggtgttggca tttaggcaat taacagatag 180
tttgccggtg ataattctct taacctccca cactcctttg acataacgat ttatgtaacg 240
aaactgaaat ttgaccagat attgttgtaa atagaaaatc tggcttgtag gtggcaaaat 300
gcggcgtctt tgttcatcaa ttccctctgt gactactcgt catcccttta tgttcgactg 360
tcgtatttct tattttccat acatatgcaa gtgagatgcc cgtgtcc 407

<210> SEQ ID NO 113
<211> LENGTH: 500
<212> TYPE: DNA
<213> ORGANISM: Yarrowia lipolytica
<220> FEATURE:

-continued

<223> OTHER INFORMATION: terminator sequence LIP1t

<400> SEQUENCE: 113

```
ggttcatgag aagataaata tataaataca ttgagatatt aaatgcgcta gattagagag     60

cctcatactg ctcggagaga agccaagacg agtactcaaa ggggattaca ccatccatat    120

ccacagacac aagctgggga aaggttctat atacactttc cggaataccg tagtttccga    180

tgttatcaat gggggcagcc aggatttcag gcacttcggt gtctcggggt gaaatggcgt    240

tcttggcctc catcaagtcg taccatgtct tcatttgcct gtcaaagtaa aacagaagca    300

gatgaagaat gaacttgaag tgaaggacgt gactacaaca gcctgcctgg tcaaccacat    360

cattcatgtt gctgatgatc ttctgaatca gctgaagagg gtactctgtc tcaatcagat    420

caccaaattt ggggtgcagt agggcacatg atcgaagcat gagtgcagta gtagcacaat    480

aagtcattcg agcaaggtag                                                500
```

<210> SEQ ID NO 114
<211> LENGTH: 500
<212> TYPE: DNA
<213> ORGANISM: Yarrowia lipolytica
<220> FEATURE:
<223> OTHER INFORMATION: terminator sequence PQX3t

<400> SEQUENCE: 114

```
atggagcgtg tgttctgagt cgatgttttc tatggagttg tgagtgttag tagacatgat     60

gggtttatat atgatgaatg aatagatgtg attttgattt gcacgatgga attgagaact    120

ttgtaaacgt acatgggaat gtatgaatgt gggggttttg tgactggata actgacggtc    180

agtggacgcc gttgttcaaa tatccaagag atgcgagaaa ctttgggtca agtgaacatg    240

tcctctctgt tcaagtaaac catcaactat gggtagtata tttagtaagg acaggagttg    300

agagaggaaa gttgccattc tttggagtcc cagaaacgta ttttcgcgtt ccaagatcaa    360

attagtagag taatacgggc acgggaatcc attcatagtc tcaattttcc cataggtgtg    420

ctacaaggtg ttgagatgtg gtacagtacc accatgattc gagataaaga gcccagaagt    480

cattgatgag gtcaagaaat                                                500
```

<210> SEQ ID NO 115
<211> LENGTH: 1026
<212> TYPE: DNA
<213> ORGANISM: artificial sequence
<220> FEATURE:
<223> OTHER INFORMATION: Hygromycin (Hgr) resistance selection marker
      gene

<400> SEQUENCE: 115

```
atgaaaaagc ctgaactcac cgccacgtct gtcgagaagt ttctgatcga aaagttcgac     60

agcgtctccg acctgatgca gctctcggag ggcgaagaat ctcgtgcttt cagcttcgat    120

gtaggagggc gtggatatgt cctgcgggta aatagctgcg ccgatggttt ctacaaagat    180

cgttatgttt atcggcactt tgcatcggcc gcgctcccga ttccggaagt gcttgacatt    240

ggggaattta gcgagagcct gacctattgc atctcccgcc gtgcacaggg tgtcacgttg    300

caagacctgc ctgaaaccga actgcccgct gttctgcagc cggtcgcgga ggccatggat    360

gcgatcgctg cggccgatct tagccagacg agcgggttcg gcccattcgg accgcaagga    420

atcggtcaat acactacatg gcgtgatttc atatgcgcga ttgctgatcc ccatgtgtat    480

cactggcaaa ctgtgatgga cgacaccgtc agtgcgtccg tcgcgcaggc tctcgatgag    540
```

```
ctgatgcttt gggccgagga ctgccccgaa gtccggcacc tcgtgcacgc ggatttcggc    600

tccaacaatg tcctgacgga caatggccgc ataacagcgg tcattgactg gagcgaggcg    660

atgttcgggg attcccaata cgaggtcgcc aacatcttct tctggaggcc gtggttggct    720

tgtatggagc agcagacgcg ctacttcgag cggaggcatc cggagcttgc aggatcgccg    780

cggctccggg cgtatatgct ccgcattggt cttgaccaac tctatcagag cttggttgac    840

ggcaatttcg atgatgcagc ttgggcgcag ggtcgatgcg acgcaatcgt ccgatccgga    900

gccgggactg tcgggcgtac acaaatcgcc cgcagaagcg cggccgtctg gaccgatggc    960

tgtgtagaag tactcgccga tagtggaaac cgacgcccca gcactcgtcc gagggcaaag   1020

gaatag                                                              1026
```

<210> SEQ ID NO 116
<211> LENGTH: 1218
<212> TYPE: DNA
<213> ORGANISM: Yarrowia lipolytica
<220> FEATURE:
<223> OTHER INFORMATION: gene LEU

<400> SEQUENCE: 116

```
atggaacccg aaactaagaa gaccaagact gactccaaga agattgttct tctcggcggc     60

gacttctgtg gccccgaggt gattgccgag gccgtcaagg tgctcaagtc tgttgctgag    120

gcctccggca ccgagtttgt gttcgaggac cgactcattg gaggagctgc cattgagaag    180

gagggcgagc ccatcaccga cgctactctc gacatctgcc gaaaggctga ctctattatg    240

ctcggtgctg tcggaggcgc tgccaacacc gtatggacca ctcccgacgg acgaaccgac    300

gtgcgacccg agcagggtct cctcaagctg cgaaaggacc tgaacctgta cgccaacctg    360

cgaccctgcc agctgctgtc gcccaagctc gccgatctct cccccatccg aaacgttgag    420

ggcaccgact tcatcattgt ccgagagctc gtcggaggta tctactttgg agagcgaaag    480

gaggatgacg gatctggcgt cgcttccgac accgagacct actccgttcc tgaggttgag    540

cgaattgccc gaatggccgc cttcctggcc cttcagcaca acccccctct tcccgtgtgg    600

tctcttgaca aggccaacgt gctggcctcc tctcgacttt ggcgaaagac tgtcactcga    660

gtcctcaagg acgaattccc ccagctcgag ctcaaccacc agctgatcga ctcggccgcc    720

atgatcctca tcaagcagcc ctccaagatg aatggtatca tcatcaccac caacatgttt    780

ggcgatatca tctccgacga ggcctccgtc atccccggtt ctctgggtct gctgccctcc    840

gcctctctgg cttctctgcc cgacaccaac gaggcgttcg gtctgtacga gccctgtcac    900

ggatctgccc ccgatctcgg caagcagaag gtcaacccca ttgccaccat tctgtctgcc    960

gccatgatgc tcaagttctc tcttaacatg aagcccgccg gtgacgctgt tgaggctgcc   1020

gtcaaggagt ccgtcgaggc tggtatcact accgccgata tcggaggctc ttcctccacc   1080

tccgaggtcg gagacttgtt gccaacaagg tcaaggagct gctcaagaag gagtaagtcg   1140

tttctacgac gcattgatgg aaggagcaaa ctgacgcgcc tgcgggttgg tctaccggca   1200

gggtccgcta gtgtataa                                                 1218
```

<210> SEQ ID NO 117
<211> LENGTH: 855
<212> TYPE: DNA
<213> ORGANISM: Yarrowia lipolytica
<220> FEATURE:
<223> OTHER INFORMATION: gene URA3

<400> SEQUENCE: 117

```
atgccctcct acgaagctcg agctaacgtc cacaagtccg cctttgccgc tcgagtgctc     60

aagctcgtgg cagccaagaa aaccaacctg tgtgcttctc tggatgttac caccaccaag    120

gagctcattg agcttgccga taaggtcgga ccttatgtgt gcatgatcaa aacccatatc    180

gacatcattg acgacttcac ctacgccggc actgtgctcc ccctcaagga acttgctctt    240

aagcacggtt tcttcctgtt cgaggacaga aagttcgcag atattggcaa cactgtcaag    300

caccagtacc ggtgtcaccg aatcgccgag tggtccgata tcaccaacgc ccacggtgta    360

cccggaaccg gaatcattgc tggcctgcga gctggtgccg aggaaactgt ctctgaacag    420

aagaaggagg acgtctctga ctacgagaac tcccagtaca aggagttcct agtcccctct    480

cccaacgaga agctggccag aggtctgctc atgctggccg agctgtcttg caagggctct    540

ctggccactg gcgagtactc caagcagacc attgagcttg cccgatccga ccccgagttt    600

gtggttggct tcattgccca gaaccgacct aagggcgact ctgaggactg gcttattctg    660

acccccgggg tgggtcttga cgacaaggga gacgctctcg gacagcagta ccgaactgtt    720

gaggatgtca tgtctaccgg aacggatatc ataattgtcg gccgaggtct gtacggccag    780

aaccgagatc ctattgagga ggccaagcga taccagaagg ctggctggga ggcttaccag    840

aagattaact gttag                                                     855
```

<210> SEQ ID NO 118
<211> LENGTH: 619
<212> TYPE: DNA
<213> ORGANISM: Yarrowia lipolytica
<220> FEATURE:
<223> OTHER INFORMATION: homologous recombination fragment pex10-up

<400> SEQUENCE: 118

```
gtggtaatcg accgactaac catttttagc tgacaaacac ttgctaactc ctataacgaa     60

tgaatgacta acttggcata ttgttaccaa gtattacttg ggatatagtt gagtgtaacc    120

attgctaaga atccaaactg gagcttctaa aggtctggga gtcgccgtat gtgttcatat    180

cgaaatcaaa gaaatcataa tcgcaacaga attcaaaatc aagcagatta atatccatta    240

ttgtactcgg atcgtgacat atctgatatg atctcggata tgatctctga ctgtttactg    300

ggagatttgt tgaagatttg ttgaggttat ctgaaaagta gacaatagag acaaaatgac    360

gatatcaaga actgaatcgg gccgaaatac tcggtatcat tcccttcagc agtaactgta    420

ttgctctatc aatgcgacga gatacctcca caattaatac tgtatacgct ctaccactca    480

tatctccaat gctaaaatat attcatgccc aggacctctg tgcactgcta tgcagcacag    540

tgttgtcgat tgaattggtc gtgtctggtc cctgatgctc tgtgtctcgc tgactagtcc    600

ttccatccag acctcgtca                                                 619
```

<210> SEQ ID NO 119
<211> LENGTH: 962
<212> TYPE: DNA
<213> ORGANISM: Yarrowia lipolytica
<220> FEATURE:
<223> OTHER INFORMATION: homologous recombination fragment pex10-dow

<400> SEQUENCE: 119

```
tttgagccga ggcagatttg ggttgcttag taagcagacg tggcgttgca agtagatgtg     60

gcaaatgggg acgaagattc cgaggggata tcatagttcc aaggggatgt catcatttgc    120

cagctttcgc cgccactttt gacgagtttt tgtgggtcaa ataagtttag ttgaactttt    180
```

```
caaatttcag ttggcatttt gttaatagaa agggtgccgg tgctgggggg ttcattcctc    240

gggttgcaga tatcctatct gtcttagggg tatctctttc aatcgacaag atgtagttgg    300

gtaacaatta tttattaata ttctctccat ccagtacagt actaacatct tgacatctca    360

gcacaagtgc atcttcccaa gtgtttgttg gagaggttgt tgggtattac ttaggaaaca    420

gaacacagta cgtggagatc ttggatacat cgtacatgga ggttatccat aaaaaagacc    480

ctccaggact agttacaatg ccgttagatg aggaaatcca caaccctgat tcactatgaa    540

catattatct tcccccaaac ttgcgatata tggcccttga tgatagcctt gattttaccc    600

ttgatggtac ctccacgacc aaccgatctg ctgtttgaag agatattttc aaatttgaag    660

tgctcagatc tactaaacat gagtccagta attctttccg tctttccgat ttccgatatt    720

cccttttta gcccgacttt tcactgctcc catgtcaaac gattaggact tgggagacaa    780

tcccactgtc aaaatcaccc cgatattctc tgtaaaacaa gtacttcttc cacgtgatct    840

tcaaatacct cttccacgtg accttcaaat acctcttcaa gtacctcttc cacgcgacct    900

tcaaagtccc ttcaaatacc cttctcaatt ctccccttct cctccatagt ccttctctct    960

ga                                                                   962
```

```
<210> SEQ ID NO 120
<211> LENGTH: 1134
<212> TYPE: DNA
<213> ORGANISM: Yarrowia lipolytica
<220> FEATURE:
<223> OTHER INFORMATION: pex10 gene

<400> SEQUENCE: 120

atgtggggaa gttcacatgc attcgctggt gaatctgatc tgacactaca actacacacc     60

aggtccaaca tgagcgacaa tacgacaatc aaaaagccga tccgacccaa accgatccgg    120

acggaacgcc tgccttacgc tggggccgca gaaatcatcc gagccaacca gaaagaccac    180

tactttgagt ccgtgcttga acagcatctc gtcacgtttc tgcagaaatg gaagggagta    240

cgatttatcc accagtacaa ggaggagctg gagacggcgt ccaagtttgc atatctcggt    300

ttgtgtacgc ttgtgggctc caagactctc ggagaagagt acaccaatct catgtacact    360

atcagagacc gaacagctct accgggggtg gtgagacggt ttggctacgt gctttccaac    420

actctgtttc catacctgtt tgtgcgctac atgggcaagt tgcgcgccaa actgatgcgc    480

gagtatcccc atctggtgga gtacgacgaa gatgagcctg tgcccagccc ggaaacatgg    540

aaggagcggg tcatcaagac gtttgtgaac aagtttgaca agttcacggc gctggagggg    600

tttaccgcga tccacttggc gattttctac gtctacggct cgtactacca gctcagtaag    660

cggatctggg gcatgcgtta tgtatttgga caccgactgg acaagaatga gcctcgaatc    720

ggttacgaga tgctcggtct gctgattttc gcccggtttg ccacgtcatt tgtgcagacg    780

ggaagagagt acctcggagc gctgctggaa aagagcgtgg agaaagaggc aggggagaag    840

gaagatgaaa aggaagcggt tgtgccgaaa aagaagtcgt caattccgtt cattgaggat    900

acagaagggg agacggaaga caagatcgat ctggaggacc ctcgacagct caagttcatt    960

cctgaggcgt ccagagcgtg cactctgtgt ctgtcataca ttagtgcgcc ggcatgtacg   1020

ccatgtggac acttttctg ttgggactgt atttccgaat gggtgagaga gaagcccgag   1080

tgtcccttgt gtcggcaggg tgtgagagag cagaacttgt tgcctatcag ataa         1134

<210> SEQ ID NO 121
<211> LENGTH: 1533
```

<212> TYPE: DNA
<213> ORGANISM: artificial sequence
<220> FEATURE:
<223> OTHER INFORMATION: cardamine mustard CgKCSER gene

<400> SEQUENCE: 121

```
atgacctcta tcaacgtgaa gctgctgtac cactacgtgc tgaccaactt cttcaacctg     60
tgcctgttcc ccctgactgc ttttcctgcc ggcaaggctt ctcaactgac caccaacgac    120
ctgcaccacc tgtactctta cctgcaccac aacctgatca ccgtgaccct gctgtttgcc    180
ttcaccgtgt tcggctctat cctgtacatc gtgaccagac ccaagcctgt gtacctggtg    240
gactactctt gttacctgcc ccccagacat ctgtcttgcg gcatctctcg agtgatggag    300
atcttctacg agatccgaaa gtctgacccc tctcgagagg tgcctttcga cgacccttct    360
tctctggagt tcctgcgaaa gatccaggag cgatctggac tgggagacga gacttatgga    420
ccccagggac tggttcatga tatgcccctg cgaatgaatt ttgccgccgc ccgagaagaa    480
actgagcagg tgatcaacgg agccctggag aagctgttcg agaacaccaa ggtgaacccc    540
cgagagattg gcatcctggt ggtgaactct tctatgttca accccacccc ctctctttct    600
gccatggtgg tgaacacctt caagctgcga tctaacatca agtctttctc tctgggcggc    660
atgggatgtt ctgccggcat catcgctatc gacctggcta aggacctgct gcacgtgcac    720
aagaacacct acgccctggt ggtgtctacc gagaacatca cccactctac ctacaccggc    780
gacaaccgat ctatgatggt gtctaactgc ctgttcagaa tgggcggagc cgccattctg    840
ctgtctaaca aggctggcga ccgacgacga tctaagtaca agctggccca cactgtgaga    900
actcacaccg gcgctgacga tcagtctttc cgatgcgtgc gacaggagga tgatgacaga    960
ggcaagatcg gcgtgtgcct gtctaaagac atcaccgccg tggccggaaa aaccgtgacc   1020
aagaacatcg ctaccctggg acctcttgtg ctgcctctgt ctgagaagtt cctgtacgtg   1080
gtgtctctga tggccaagaa gctgttcaag aacaagatca agcacaccta cgtgcccgat   1140
ttcaagctgg ccatcgacca cttctgcatc catgctggcg gaagagctgt gattgacgtg   1200
ctggagaaga acctggccct gtctcctgtg gatgtggagg cttctcgatc taccctgcac   1260
cgattcggca acacctcttc ttcttctatc tggtacgagc tggcctacat cgaagccaag   1320
ggccgaatga agaagggcaa caaggtgtgg caaatcgcca tcggctctgg cttcaagtgc   1380
aactctgccg tttgggtggc cctgtgtaat gtgaagccct ctgtgaactc tccttgggag   1440
cactgcattg acagataccc cgtggagatc aactacggct cttctaagtc tgagacccga   1500
gcccaaaacg gccgatctaa ggacgagctg taa                                1533
```

<210> SEQ ID NO 122
<211> LENGTH: 1557
<212> TYPE: DNA
<213> ORGANISM: artificial sequence
<220> FEATURE:
<223> OTHER INFORMATION: Yarrowia lipolytica DGAT1ER gene

<400> SEQUENCE: 122

```
atgactatcg actcacaata ctacaagtcg cgagacaaaa acgacacggc acccaaaatc     60
gcgggaatcc gatatgcccc gctatcgaca ccattactca accgatgtga gaccttctct    120
ctggtctggc acattttcag cattcccact ttcctcacaa ttttcatgct atgctgcgca    180
attccactgc tctggccatt tgtgattgcg tatgtagtgt acgctgttaa agacgactcc    240
ccgtccaacg gaggagtggt caagcgatac tcgcctattt caagaaactt cttcatctgg    300
```

aagctctttg gccgctactt ccccataact ctgcacaaga cggtggatct ggagcccacg 360
cacacatact accctctgga cgtccaggag tatcacctga ttgctgagag atactggccg 420
cagaacaagt acctccgagc aatcatctcc accatcgagt actttctgcc cgccttcatg 480
aaacggtctc tttctatcaa cgagcaggag cagcctgccg agcgagatcc tctcctgtct 540
cccgtttctc ccagctctcc gggttctcaa cctgacaagt ggattaacca cgacagcaga 600
tatagccgtg gagaatcatc tggctccaac ggccacgcct cgggctccga acttaacggc 660
aacggcaaca atggcaccac taaccgacga cctttgtcgt ccgcctctgc tggctccact 720
gcatctgatt ccacgcttct taacgggtcc ctcaactcct acgccaacca gatcattggc 780
gaaaacgacc cacagctgtc gcccacaaaa ctcaagccca ctggcagaaa atacatcttc 840
ggctaccacc cccacggcat tatcggcatg ggagcctttg gtggaattgc caccgaggga 900
gctggatggt ccaagctctt tccgggcatc cctgtttctc ttatgactct caccaacaac 960
ttccgagtgc ctctctacag agagtacctc atgagtctgg gagtcgcttc tgtctccaag 1020
aagtcctgca aggccctcct caagcgaaac cagtctatct gcattgtcgt tggtggagca 1080
caggaaagtc ttctggccag acccggtgtc atggacctgg tgctactcaa gcgaaagggt 1140
tttgttcgac ttggtatgga ggtcggaaat gtcgcccttg ttcccatcat ggcctttggt 1200
gagaacgacc tctatgacca ggttagcaac gacaagtcgt ccaagctgta ccgattccag 1260
cagtttgtca agaacttcct tggattcacc cttcctttga tgcatgcccg aggcgtcttc 1320
aactacgatg tcggtcttgt cccctacagg cgacccgtca acattgtggt tggttccccc 1380
attgacttgc cttatctccc acaccccacc gacgaagaag tgtccgaata ccacgaccga 1440
tacatcgccg agctgcagcg aatctacaac gagcacaagg atgaatattt catcgattgg 1500
accgaggagg gcaaaggagc cccagagttc cgaatgattg agaaggacga gctgtaa 1557

<210> SEQ ID NO 123
<211> LENGTH: 1461
<212> TYPE: DNA
<213> ORGANISM: artificial sequence
<220> FEATURE:
<223> OTHER INFORMATION: Yarrowia lipolytica SCDER gene

<400> SEQUENCE: 123
atggtgaaaa acgtggacca agtggatctc tcgcaggtcg acaccattgc ctccggccga 60
gatgtcaact acaaggtcaa gtacacctcc ggcgttaaga tgagccaggg cgcctacgac 120
gacaagggcc gccacatttc cgagcagccc ttcacctggg ccaactggca ccagcacatc 180
aactggctca acttcattct ggtgattgcg ctgcctctgt cgtcctttgc tgccgctccc 240
ttcgtctcct tcaactggaa gaccgccgcg tttgctgtcg gctattacat gtgcaccggt 300
ctcggtatca ccgccggcta ccaccgaatg tgggcccatc gagcctacaa ggccgctctg 360
cccgttcgaa tcatccttgc tctgtttgga ggaggagctg tcgagggctc catccgatgg 420
tgggcctcgt ctcaccgagt ccaccaccga tggaccgact ccaacaagga cccttacgac 480
gcccgaaagg gattctggtt ctcccacttt ggctggatgc tgcttgtgcc caaccccaag 540
aacaagggcc gaactgacat ttctgacctc aacaacgact gggttgtccg actccagcac 600
aagtactacg tttacgttct cgtcttcatg gccattgttc tgcccaccct cgtctgtggc 660
tttggctggg gcgactggaa gggaggtctt gtctacgccg gtatcatgcg atacaccttt 720
gtgcagcagg tgactttctg tgtcaactcc cttgcccact ggattggaga gcagcccttc 780
gacgaccgac gaactccccg agaccacgct cttaccgccc tggtcacctt tggagagggc 840

-continued

```
taccacaact tccaccacga gttcccctcg gactaccgaa acgccctcat ctggtaccag     900

tacgacccca ccaagtggct catctggacc ctcaagcagg ttggtctcgc ctgggacctc     960

cagaccttct cccagaacgc catcgagcag ggtctcgtgc agcagcgaca gaagaagctg    1020

gacaagtggc gaaacaacct caactggggt atccccattg agcagctgcc tgtcattgag    1080

tttgaggagt tccaagagca ggccaagacc cgagatctgg ttctcatttc tggcattgtc    1140

cacgacgtgt ctgcctttgt cgagcaccac cctggtggaa aggccctcat tatgagcgcc    1200

gtcggcaagg acggtaccgc tgtcttcaac ggaggtgtct accgacactc caacgctggc    1260

cacaacctgc ttgccaccat gcgagtttcg gtcattcgag gcggcatgga ggttgaggtg    1320

tggaagactg cccagaacga aaagaaggac cagaacattg tctccgatga gagtggaaac    1380

cgaatccacc gagctggtct ccaggccacc cgggtcgaga accccggtat gtctggcatg    1440

gctgctaagg acgagctgta g                                              1461
```

<210> SEQ ID NO 124
<211> LENGTH: 1533
<212> TYPE: DNA
<213> ORGANISM: artificial sequence
<220> FEATURE:
<223> OTHER INFORMATION: Afican mustard BtFAE1ER gene

<400> SEQUENCE: 124

```
atgacctctg tgaacgtgaa gctgatctac cactacgtga tcaccaacct gttcaacctg      60

tgcttcttcc ccctgactgc tatcgttgcc ggcaaagctt ctcgactgac cattgacgac     120

ctgcaccacc tgtactactc ttacctgcag cacaacctga ttaccatcgc ccccctgttt     180

gcctttaccg tgttcggctc tgtgctgtac attgccaccc gacctaagcc tgtgtacctg     240

gtggagtact cttgttacct gccccccact cactgtcgat cttctatctc taaggtgatg     300

gacatcttct accaggtgcg aaaggccgac ccctctagaa atggcacctg cgacgactct     360

tcttggctgg acttcctgcg aaagatccag gagcgatctg gcctgggaga tgagactcat     420

ggccctgagg gactgcttca cgtgcctccc agaaaaacct ttgccgccgc tagagaagaa     480

accgagaagg tgattatcgg cgccctggag aacctgttcg agaacaccaa ggtgaacccc     540

aaggacatcg gcatcctggt ggtgaactct tctatgttca accccacccc ctctctttct     600

gccatggtgg tgaacacctt caagctgcga tctaacgtgc gatctttcaa cctgggaggc     660

atgggatgtt ctgctggcgt gatcgctatt gacctggcca aagacctgct gcacgtgcac     720

aagaacacct acgccctggt ggtgtctacc gagaacatca cctacaacat ctacgccggc     780

gacaacaagt ctatgatggt gtctaactgc ctgttccgag tgggaggagc cgctattctg     840

ctgtctaaca agccccgaga ccgacgacga tctaagtacg agctggtgca caccgtgcga     900

actcataccg gagctgacga caagtctttc cgatgcgtgc aacagggcga tgacgagtct     960

ggaaagaccg gcgtgtctct gtctaaggac atcaccgacg tggctggaag aaccgtgaag    1020

aagaacatct ctaccctggg ccctctgatt ctgcctctgt ctgagaagct gctgttcttc    1080

gtgaccttca tgggcaagaa gctgttcaag gacaagatca agcactacta cgtgcccgac    1140

ttcaagcttg ccatcgacca cttctgtatc cacgctggcg gacgagctgt gattgatgtg    1200

ctggagaaga accttggact ggcccctatt gatgtggagg cctctcgatc tacccttcac    1260

cgattcggca acacctcttc ttcttctatc tggtacgagc tggcctacat cgaagctaag    1320

ggccgaatga agaagggcaa caaggtgtgg caaatcgctc tgggctctgg cttcaagtgc    1380
```

```
aactctgccg tttgggtggc cctgagaaat gtgaaggcct ctcgaaagtc tccttgggag   1440

cactgcattg accgataccc cgtgaagatc gactacgact ctgccaagtc tgaggtgaga   1500

gtgcagaacg gccgatctaa ggacgagctg taa                                1533
```

<210> SEQ ID NO 125
<211> LENGTH: 1530
<212> TYPE: DNA
<213> ORGANISM: artificial sequence
<220> FEATURE:
<223> OTHER INFORMATION: cardamine mustard CgKCSPTS gene

<400> SEQUENCE: 125

```
atgacctcta tcaacgtgaa gctgctgtac cactacgtgc tgaccaactt cttcaacctg     60

tgcctgttcc ccctgactgc ttttcctgcc ggcaaggctt ctcaactgac caccaacgac    120

ctgcaccacc tgtactctta cctgcaccac aacctgatca ccgtgaccct gctgtttgcc    180

ttcaccgtgt tcggctctat cctgtacatc gtgaccagac ccaagcctgt gtacctggtg    240

gactactctt gttacctgcc ccccagacat ctgtcttgcg gcatctctcg agtgatggag    300

atcttctacg agatccgaaa gtctgacccc tctcgagagg tgcctttcga cgacccttct    360

tctctggagt tcctgcgaaa gatccaggag cgatctggac tgggagacga gacttatgga    420

ccccagggac tggttcatga tatgcccctg cgaatgaatt ttgccgccgc ccgagaagaa    480

actgagcagg tgatcaacgg agccctggag aagctgttcg agaacaccaa ggtgaacccc    540

cgagagattg gcatcctggt ggtgaactct tctatgttca accccacccc ctctctttct    600

gccatggtgg tgaacacctt caagctgcga tctaacatca agtctttctc tctgggcggc    660

atgggatgtt ctgccggcat catcgctatc gacctggcta aggacctgct gcacgtgcac    720

aagaacacct acgccctggt ggtgtctacc gagaacatca cccactctac ctacaccggc    780

gacaaccgat ctatgatggt gtctaactgc ctgttcagaa tgggcggagc cgccattctg    840

ctgtctaaca aggctggcga ccgacgacga tctaagtaca agctggccca cactgtgaga    900

actcacaccg gcgctgacga tcagtctttc cgatgcgtgc gacaggagga tgatgacaga    960

ggcaagatcg gcgtgtgcct gtctaaagac atcaccgccg tggccggaaa aaccgtgacc   1020

aagaacatcg ctaccctggg acctcttgtg ctgcctctgt ctgagaagtt cctgtacgtg   1080

gtgtctctga tggccaagaa gctgttcaag aacaagatca agcacaccta cgtgcccgat   1140

ttcaagctgg ccatcgacca cttctgcatc catgctggcg gaagagctgt gattgacgtg   1200

ctggagaaga acctggccct gtctcctgtg gatgtggagg cttctcgatc taccctgcac   1260

cgattcggca acacctcttc ttcttctatc tggtacgagc tggcctacat cgaagccaag   1320

ggccgaatga agaagggcaa caaggtgtgg caaatcgcca tcggctctgg cttcaagtgc   1380

aactctgccg tttgggtggc cctgtgtaat gtgaagccct ctgtgaactc tccttgggag   1440

cactgcattg acagataccc cgtggagatc aactacggct cttctaagtc tgagacccga   1500

gcccaaaacg gccgatcttc caagctgtaa                                    1530
```

<210> SEQ ID NO 126
<211> LENGTH: 1530
<212> TYPE: DNA
<213> ORGANISM: artificial sequence
<220> FEATURE:
<223> OTHER INFORMATION: African mustard BtFAE1PTS gene

<400> SEQUENCE: 126

```
atgacctctg tgaacgtgaa gctgatctac cactacgtga tcaccaacct gttcaacctg     60
```

```
tgcttcttcc ccctgactgc tatcgttgcc ggcaaagctt ctcgactgac cattgacgac    120
ctgcaccacc tgtactactc ttacctgcag cacaacctga ttaccatcgc ccccctgttt    180
gcctttaccg tgttcggctc tgtgctgtac attgccaccc gacctaagcc tgtgtacctg    240
gtggagtact cttgttacct gcccccccact cactgtcgat cttctatctc taaggtgatg    300
gacatcttct accaggtgcg aaaggccgac ccctctagaa atggcacctg cgacgactct    360
tcttggctgg acttcctgcg aaagatccag gagcgatctg gcctgggaga tgagactcat    420
ggccctgagg gactgcttca cgtgcctccc agaaaaacct ttgccgccgc tagagaagaa    480
accgagaagg tgattatcgg cgccctggag aacctgttcg agaacaccaa ggtgaacccc    540
aaggacatcg gcatcctggt ggtgaactct tctatgttca accccacccc ctctctttct    600
gccatggtgg tgaacacctt caagctgcga tctaacgtgc gatctttcaa cctgggaggc    660
atgggatgtt ctgctggcgt gatcgctatt gacctggcca aagacctgct gcacgtgcac    720
aagaacacct acgccctggt ggtgtctacc gagaacatca cctacaacat ctacgccggc    780
gacaacaagt ctatgatggt gtctaactgc ctgttccgag tgggaggagc cgctattctg    840
ctgtctaaca agccccgaga ccgacgacga tctaagtacg agctggtgca caccgtgcga    900
actcataccg gagctgacga caagtctttc cgatgcgtgc aacagggcga tgacgagtct    960
ggaaagaccg gcgtgtctct gtctaaggac atcaccgacg tggctggaag aaccgtgaag   1020
aagaacatct ctaccctggg ccctctgatt ctgcctctgt ctgagaagct gctgttcttc   1080
gtgaccttca tgggcaagaa gctgttcaag gacaagatca agcactacta cgtgcccgac   1140
ttcaagcttg ccatcgacca cttctgtatc cacgctggcg gacgagctgt gattgatgtg   1200
ctggagaaga accttggact ggcccctatt gatgtggagg cctctcgatc tacccttcac   1260
cgattcggca acacctcttc ttcttctatc tggtacgagc tggcctacat cgaagctaag   1320
ggccgaatga agaagggcaa caaggtgtgg caaatcgctc tgggctctgg cttcaagtgc   1380
aactctgccg tttgggtggc cctgagaaat gtgaaggcct ctcgaaagtc tccttgggag   1440
cactgcattg accgataccc cgtgaagatc gactacgact ctgccaagtc tgaggtgaga   1500
gtgcagaacg gccgatcttc caagctgtaa                                    1530
```

<210> SEQ ID NO 127
<211> LENGTH: 1596
<212> TYPE: DNA
<213> ORGANISM: artificial sequence
<220> FEATURE:
<223> OTHER INFORMATION: cardamine mustard CgKCSMTS

<400> SEQUENCE: 127

```
atgctttcac tacgtcaatc tataagattt ttcaagccag ccacaagaac tttgtgtagc     60
tctagatatc tgcttatgac ctctatcaac gtgaagctgc tgtaccacta cgtgctgacc    120
aacttcttca acctgtgcct gttccccctg actgcttttc ctgccggcaa ggcttctcaa    180
ctgaccacca acgacctgca ccacctgtac tcttacctgc accacaacct gatcaccgtg    240
accctgctgt ttgccttcac cgtgttcggc tctatcctgt acatcgtgac cagacccaag    300
cctgtgtacc tggtggacta ctcttgttac ctgcccccca gacatctgtc ttgcggcatc    360
tctcgagtga tggagatctt ctacgagatc cgaaagtctg acccctctcg agaggtgcct    420
ttcgacgacc cttcttctct ggagttcctg cgaaagatcc aggagcgatc tggactggga    480
gacgagactt atggacccca gggactggtt catgatatgc cctgcgaat gaattttgcc    540
```

-continued

```
gccgcccgag aagaaactga gcaggtgatc aacggagccc tggagaagct gttcgagaac    600

accaaggtga acccccgaga gattggcatc ctggtggtga actcttctat gttcaacccc    660

accccctctc tttctgccat ggtggtgaac accttcaagc tgcgatctaa catcaagtct    720

ttctctctgg gcggcatggg atgttctgcc ggcatcatcg ctatcgacct ggctaaggac    780

ctgctgcacg tgcacaagaa cacctacgcc ctggtggtgt ctaccgagaa catcacccac    840

tctacctaca ccggcgacaa ccgatctatg atggtgtcta actgcctgtt cagaatgggc    900

ggagccgcca ttctgctgtc taacaaggct ggcgaccgac gacgatctaa gtacaagctg    960

gcccacactg tgagaactca caccggcgct gacgatcagt ctttccgatg cgtgcgacag   1020

gaggatgatg acagaggcaa gatcggcgtg tgcctgtcta aagacatcac cgccgtggcc   1080

ggaaaaaccg tgaccaagaa catcgctacc ctgggacctc ttgtgctgcc tctgtctgag   1140

aagttcctgt acgtggtgtc tctgatggcc aagaagctgt tcaagaacaa gatcaagcac   1200

acctacgtgc ccgatttcaa gctggccatc gaccacttct gcatccatgc tggcggaaga   1260

gctgtgattg acgtgctgga gaagaacctg gccctgtctc ctgtggatgt ggaggcttct   1320

cgatctaccc tgcaccgatt cggcaacacc tcttcttctt ctatctggta cgagctggcc   1380

tacatcgaag ccaagggccg aatgaagaag ggcaacaagg tgtggcaaat cgccatcggc   1440

tctggcttca agtgcaactc tgccgtttgg gtggccctgt gtaatgtgaa gccctctgtg   1500

aactctcctt gggagcactg cattgacaga taccccgtgg agatcaacta cggctcttct   1560

aagtctgaga cccgagccca aaacggccga tcttaa                              1596
```

RECOMBINANT YEAST STRAIN FOR PRODUCING NERVONIC ACIDS AND APPLICATION THEREOF

TECHNICAL FIELD

The present invention belongs to the field of biotechnology. More specifically, the present invention relates to an engineered recombinant yeast strain which can efficiently produce a nervonic acid (cis-15-tetracosenoic acid, alias selacholeic acid, C24:1, Δ15) at a high concentration.

BACKGROUND

Unsaturated fatty acids are mostly essential fatty acids for the human body, which have the functions of regulating blood lipids, clearing blood clots, replenishing the brain and relieving inflammation, and mainly include monounsaturated fatty acids and polyunsaturated fatty acids. Wherein, very long chain monounsaturated fatty acid (VLCMFA) is an unsaturated fatty acid with more than 18 carbon atoms in the main carbon chain and only one double bond. Common ones are Eicosenoic acid (C20:1Δ11), Erucic acid (C22:1Δ13), Nervonic acid (C24:1Δ15) and Ximenynic acid (C26:1Δ17). Very long chain monounsaturated fatty acids have unique medicinal effects, health benefits and industrial uses. However, compared with polyunsaturated fatty acids, the application and promotion of very long chain monounsaturated fatty acids urgently need to be strengthened.

Nervonic acid (cis-15-tetracosenoic acid, alias squalene acid, C24:1Δ15) is an very long chain monounsaturated fatty acid closely related to human health. Nervonic acid mainly exists in the white matter and myelin nerve fibers of animal brain in the form of glycosphingolipid and sphingomyelin, and is an important component of biofilm. Nervonic acid plays an important role in medicine and health care, and can be used to treat neurological disorders such as multiple sclerosis. In addition, studies have shown that nervonic acid can promote the development of the nervous system, and especially plays an important role in the growth and development of brain nerve cells and optic nerve cells in infants and young children. Nervonic acid needed by the human body mainly depends on external sources. In recent years, with the continuous deepening of the understanding of nervonic acid's medicine and health benefits, the value of its resource development and utilization has been highlighted, and the demand for products is gradually expanding.

There are many natural sources of nervonic acid. The currently known animals, plants, and microorganisms that are rich in nervonic acids include sharks, *Malania oleifera, Acer truncatum*, cardamine mustard, microalgae, and a few molds. *Malania oleifera* is a peculiar plant in China that is rich in nervonic acid in nature, and the oil content of the kernel of *Malania oleifera* is about 64.5%, of which the content of nervonic acid is as high as 43.2%, but it is difficult to grow *Malania oleifera*. The nervonic acid content of *Acer truncatum* seed oil is about 5.8%, which is currently the main source of nervonic acid. *Acer truncatum* grows slowly. Artificially planted *Acer truncatum* bears fruit in 4-6 years, and it enters the full fruit period in 8-10 years. Therefore, the extraction of nervonic acid from *Acer truncatum* has the disadvantages of long growth cycle, seasonal restriction of raw material supply, and low output. Oil-producing microorganisms can synthesize fatty acids with high cell content, and after genetic engineering, they can form microbial oils with a composition similar to vegetable oils.

*Yarrowia lipolytica* is an oil-producing microorganism, the oil accumulation of which can account for 44 to 70% of the dry cell weight. And it has characteristics such as a fast growth rate, high cell fermentation density, a wide range of carbon source utilization, and simple genetic operation, and has great potential to be developed into a nervonic acid cell factory. Most of the fatty acids in *Yarrowia lipolytica* are C16 and C18 fatty acids. Due to the lack of carbon chain elongase and fatty acid desaturase necessary for the synthesis of very long chain monounsaturated fatty acids, wild strains cannot synthesize nervonic acid. Preliminary research introduced fatty acid elongase (AtFAE1, BtFAE1 and CgKCS), desaturase (SCD) and diglyceride acyltransferase (DGAT1) into *Yarrowia lipolytica* through genetic engineering methods. The constructed recombinant yeast cells can produce nervonic acid, but its content only accounts for 1.5% of the total oil content in cells, which is difficult to meet industrial needs.

SUMMARY OF THE INVENTION

In order to solve the above-mentioned technical problems, in the present invention, by overexpressing related genes such as fatty acid elongase, desaturase, diglyceride acyltransferase, etc., and optionally by regulating the triglyceride synthesis and decomposition pathways, the sphingomyelin synthesis and decomposition pathways, lipid subcellular level synthesis and decomposition pathways, and redox equilibrium pathways of the recombinant yeast strains, the constructed recombinant yeast strain has a greatly improved ability to produce nervonic acid. After fermentation optimization, the content of nervonic acid obtained by extraction accounts for 39.6% of the total fatty acid content. The specific technical solutions are as follows:

Scheme 1. The present invention provides a recombinant yeast strain characterized by overexpression of:

(a) a gene encoding a Δ9 desaturase;

(b) at least four genes encoding fatty acid elongases;

(c) a gene encoding a diglyceride acyltransferase;

(d) a gene encoding a fatty acid elongase targeting the endoplasmic reticulum;

(e) a gene encoding a diglyceride acyltransferase targeting the endoplasmic reticulum; and/or (f) a gene encoding a Δ9 desaturase targeting the endoplasmic reticulum.

The overexpressed fatty acid synthesis expression module in the recombinant yeast strain specifically comprises fatty acid elongase gene and desaturase gene related to nervonic acid production. Wherein, the fatty acid elongase gene can be selected from, but is not limited to, the *Mortierella alpina* C16 elongase gene MaLCE1, as shown in SEQ ID NO: 93; arabidopsis AtFAE1, as shown in SEQ ID NO: 94; African mustard BtFAE1, as shown in SEQ ID NO: 95; cardamine mustard CgKCS, as shown in SEQ ID NO: 96; rat fatty acid elongase 2 gene rELO2, as shown in SEQ ID NO: 97; *Cryptosporidium parvum* long-chain fatty acid elongase gene CpLCE, as shown in SEQ ID NO: 98; goat fatty acid elongase 6 gene gELOVL6, as shown in SEQ ID NO: 99. Wherein, the desaturase gene can be selected from, but is not limited to, *Yarrowia lipolytica* SCD, as shown in SEQ ID NO: 84; *Cunninghamia chinensis* Δ9 fatty acid desaturase gene D9DMB, as shown in SEQ ID NO: 100; nematode Δ9 fatty acid desaturase gene CeFAT6, as shown in SEQ ID NO: 101; *Mortierella alpina* Δ9 fatty acid desaturase gene MaOLE2, as shown in SEQ ID NO: 102; arabidopsis AtADS1, as shown in SEQ ID NO: 103; arabidopsis AtADS2, as shown in SEQ ID NO: 104.

Meanwhile, the recombinant yeast strain overexpresses a triglyceride synthesis module, specifically referring to a diglyceride acyltransferase gene, which is the enzyme that catalyzes the last step of triacylglycerol ester (TAG) synthesis and the only key enzyme and rate-limiting enzyme in the TAG synthesis process. Increasing the expression of diglyceride acyltransferase in yeast cells can increase the lipid content in the cells.

Meanwhile, the overexpression of yeast lipid synthesis and decomposition subcellular level regulation module in the recombinant yeast strain specifically refers to the regulation of the level in endoplasmic reticulum, that is, the endoplasmic reticulum retention signal peptide KDEL is added to the 3'end of the corresponding gene.

Preferably, the yeast strain described in Scheme 1 is *Yarrowia lipolytica*.

Preferably, the gene encoding a Δ9 desaturase is *Yarrowia lipolytica* SCD gene, the nucleotide sequence of which is shown in SEQ ID NO: 84;

Preferably, the four genes encoding fatty acid elongases are respectively *Mortierella alpina* C16/18 elongase gene MaLCE1, the nucleotide sequence of which is shown in SEQ ID NO: 93; arabidopsis AtFAE1 gene, the nucleotide sequence of which is shown in SEQ ID NO: 94; African mustard BtFAE1 gene, the nucleotide sequence of which is shown in SEQ ID NO: 95; cardamine mustard CgKCS gene, the nucleotide sequence of which is shown in SEQ ID NO: 96;

preferably, the gene encoding a diglyceride acyltransferase is *Yarrowia lipolytica* DGAT1 gene, the nucleotide sequence of which is shown in SEQ ID NO: 83;

preferably, the gene encoding a fatty acid elongase targeting the endoplasmic reticulum is cardamine mustard $CgKCS_{ER}$ gene with an encoding sequence for the signal peptide targeting the endoplasmic reticulum, the nucleotide sequence of which is shown in SEQ ID NO: 121;

preferably, the gene encoding a diglyceride acyltransferase targeting the endoplasmic reticulum is *Yarrowia lipolytica* $DGAT1_{ER}$ gene with an encoding sequence for the signal peptide targeting the endoplasmic reticulum, the nucleotide sequence of which is shown in SEQ ID NO: 122;

preferably, the gene encoding a Δ9 desaturase targeting the endoplasmic reticulum is *Yarrowia lipolytica* $SCD_{ER}$ gene with an encoding sequence for the signal peptide targeting the endoplasmic reticulum, the nucleotide sequence of which is shown in SEQ ID NO: 123.

In another embodiment, the present invention provides a recombinant yeast strain for the production of nervonic acid, and on the basis of the strain involved in Scheme 1, the recombinant yeast strain can further overexpress:

(a) two genes encoding fatty acid elongases targeting the endoplasmic reticulum; and/or (b) two genes encoding fatty acid elongases targeting the peroxisomes.

Preferably, the two genes encoding fatty acid elongases targeting the endoplasmic reticulum are respectively cardamine mustard $CgKCS_{ER}$ genes with an encoding sequence for the signal peptide targeting the endoplasmic reticulum, the nucleotide sequence of which is shown in SEQ ID NO: 121; African mustard $BtFAE1_{ER}$ gene with an encoding sequence for the signal peptide targeting endoplasmic reticulum, the nucleotide sequence of which is shown in SEQ ID NO: 124;

preferably, the two genes encoding fatty acid elongases targeting peroxisomes are respectively cardamine mustard $CgKCS_{PTS}$ gene with an encoding sequence for the signal peptide targeting the peroxisomes, the nucleotide sequence of which is shown in SEQ ID NO: 125; African mustard $BtFAE1_{PTS}$ gene with an encoding sequence for the signal peptide targeting the peroxisomes, the nucleotide sequence of which is shown in SEQ ID NO: 126.

In another embodiment, the present invention provides a recombinant yeast strain for the production of nervonic acid, and on the basis of the strain involved in Scheme 1, the recombinant yeast strain can further overexpress:

(a) a gene encoding an aldehyde dehydrogenase;

(b) a gene encoding a glucose-6-phosphate dehydrogenase;

(c) a gene encoding a glutathione disulfide reductase; and/or (d) a gene encoding a glutathione peroxidase.

The recombinant yeast strain further comprises a redox equilibrium regulation module, which comprises genes related in maintaining the reducing power of NADPH regeneration and oxidative stress defense in the process of nervonic acid synthesis.

The gene encoding an aldehyde dehydrogenase is preferably *E. coli* EcAldH gene, the nucleotide sequence of which is shown in SEQ ID NO: 105; the gene encoding a glucose-6-phosphate dehydrogenase is preferably *Saccharomyces cerevisiae* ScZwf gene, the nucleotide sequence of which is shown in SEQ ID NO: 106; the gene encoding a glutathione disulfide reductase is preferably *Yarrowia lipolytica* ylGSR gene, the nucleotide sequence of which is shown in SEQ ID NO: 91; the gene encoding a glutathione peroxidase is preferably *Yarrowia lipolytica* ylGPO gene, the nucleotide sequence of which is shown in SEQ ID NO: 92.

Scheme 2. The present invention provides a recombinant yeast strain characterized by overexpression of:

(a) a gene encoding a Δ9 desaturase;

(b) at least three genes encoding fatty acid elongases;

(c) a gene encoding a diglyceride acyltransferase; and/or (d) a gene encoding a phospholipase A2.

The recombinant yeast strain comprises a sphingomyelin synthesis and decomposition regulation module, specifically relating to the phospholipase A2 (PLA2) gene. PLA2 is a hydrolase that can catalyze the two-position acyl group on the phospholipid glycerol molecule, and its overexpression can increase the supply of substrates during nervonic acid synthesis. The gene encoding a phospholipase A2 can be selected from, but is not limited to, PLA2-1, as shown in SEQ ID NO: 85, PLA2-2, as shown in SEQ ID NO: 86, PLA2-3, as shown in SEQ ID NO: 87, PLA2-4, as shown in SEQ ID NO: 88, PLA2-5, as shown in SEQ ID NO: 89, and PLA2-6, as shown in SEQ ID NO: 90.

Preferably, the gene encoding a Δ9 desaturase is *Yarrowia lipolytica* SCD gene, the nucleotide sequence of which is shown in SEQ ID NO: 84;

preferably, the three genes encoding fatty acid elongases are respectively arabidopsis AtFAE1 gene, the nucleotide sequence of which is shown in SEQ ID NO: 94; African mustard BtFAE1 gene, the nucleotide sequence of which is shown in SEQ ID NO: 95; cardamine mustard CgKCS gene, the nucleotide sequence of which is shown in SEQ ID NO: 96;

preferably, the gene encoding a diglyceride acyltransferase is *Yarrowia lipolytica* DGAT1 gene, the nucleotide sequence of which is shown in SEQ ID NO: 83.

Scheme 3. The present invention provides a recombinant yeast strain characterized by overexpression of:

(a) a gene encoding a fatty acid elongase targeting the peroxisomes;

(b) a gene encoding a fatty acid elongase;

(c) a gene encoding a fatty acid elongase targeting the endoplasmic reticulum;

(d) a gene encoding a diglyceride acyltransferase targeting the endoplasmic reticulum; and/or (e) a gene encoding a Δ9 desaturase targeting the endoplasmic reticulum.

Preferably, the yeast strain is *Yarrowia lipolytica;* preferably, the gene encoding a fatty acid elongase targeting the peroxisomes is cardamine mustard $CgKCS_{PTS}$ gene with an encoding sequence for the signal peptide targeting the peroxisomes, the nucleotide sequence of which is shown in SEQ ID NO: 125;

preferably, the gene encoding a fatty acid elongase is the *Mortierella alpina* C16/18 elongase gene MaLCE1 gene, the nucleotide sequence of which is shown in SEQ ID NO: 93;

preferably, the gene encoding a fatty acid elongase targeting the endoplasmic reticulum is cardamine mustard $CgKCS_{ER}$ gene with an encoding sequence for the signal peptide targeting the endoplasmic reticulum, the nucleotide sequence of which is shown in SEQ ID NO: 121;

preferably, the gene encoding a diglyceride acyltransferase targeting the endoplasmic reticulum is *Yarrowia lipolytica* $DGAT1_{ER}$ gene with an encoding sequence for the signal peptide targeting the endoplasmic reticulum, the nucleotide sequence of which is shown in SEQ ID NO: 122;

preferably, the gene encoding a Δ9 desaturase targeting the endoplasmic reticulum is the *Yarrowia lipolytica* $SCD_{ER}$ gene with an encoding sequence for the signal peptide targeting the endoplasmic reticulum, the nucleotide sequence of which is shown in SEQ ID NO: 123.

Scheme 4. The present invention provides a recombinant yeast strain characterized by overexpression of:

(a) a gene encoding a Δ9 desaturase;

(b) a gene encoding a fatty acid elongase;

(c) a gene encoding a fatty acid elongase targeting the endoplasmic reticulum; and/or (d) a gene encoding a fatty acid elongase targeting the mitochondria.

Preferably, the yeast strain is *Yarrowia lipolytica;* preferably, the gene encoding a Δ9 desaturase is *Mortierella alpina* Δ9 fatty acid desaturase MaOLE2 gene, the nucleotide sequence of which is shown in SEQ ID NO: 102;

preferably, the gene encoding a fatty acid elongase is goat fatty acid elongase 6 gELOVL6 gene, the nucleotide sequence of which is shown in SEQ ID NO: 99;

preferably, the gene encoding a fatty acid elongase targeting the endoplasmic reticulum is cardamine mustard $CgKCS_{ER}$ gene with an encoding sequence for the signal peptide targeting the endoplasmic reticulum, the nucleotide sequence of which is shown in SEQ ID NO: 121;

preferably, the gene encoding a fatty acid elongase targeting the mitochondria is cardamine mustard $CgKCS_{MTS}$ with an encoding sequence for the signal peptide targeting the mitochondria, the nucleotide sequence of which is shown in SEQ ID NO: 127.

Scheme 5. The present invention provides a recombinant yeast strain characterized by overexpression of:

(a) two genes encoding Δ9 desaturases;

(b) three genes encoding fatty acid elongases; and/or (c) a gene encoding a diglyceride acyltransferase.

Preferably, the yeast strain is *Yarrowia lipolytica;* preferably, the two genes encoding Δ9 desaturases are respectively *Yarrowia lipolytica* SCD gene, the nucleotide sequence of which is shown in SEQ ID NO: 84; arabidopsis AtADS1 gene, the nucleotide sequence of which is shown in SEQ ID NO: 103; or the two genes encoding Δ9 desaturases are respectively *Yarrowia lipolytica* SCD gene, the nucleotide sequence of which is shown in SEQ ID NO: 84; arabidopsis AtADS2 gene, the nucleotide sequence of which is shown in SEQ ID NO: 104;

preferably, the three genes encoding fatty acid elongases are respectively arabidopsis AtFAE1 gene, the nucleotide sequence of which is shown in SEQ ID NO: 94; African mustard BtFAE1 gene, the nucleotide sequence of which is shown in SEQ ID NO: 95; cardamine mustard CgKCS gene, the nucleotide sequence of which is shown in SEQ ID NO: 96;

preferably, the gene encoding a diglyceride acyltransferase is *Yarrowia lipolytica* DGAT1 gene, as shown in SEQ ID NO: 83.

Scheme 6. The present invention provides a recombinant yeast strain, wherein the expression of peroxisome biogenesis factor 10 in the strain is down-regulated and the strain further overexpresses:

(a) a gene encoding a fatty acid elongase targeting the peroxisomes;

(b) a gene encoding a fatty acid elongase;

(c) a gene encoding a fatty acid elongase targeting the endoplasmic reticulum;

(d) a gene encoding a diglyceride acyltransferase targeting the endoplasmic reticulum; and/or (e) a gene encoding a Δ9 desaturase targeting the endoplasmic reticulum.

The recombinant yeast strain comprises a triglyceride decomposition module, specifically relating to a peroxisome biogenesis factor 10 gene knockout module. The knockout of this gene can reduce the decomposition of long-chain fatty acids.

Preferably, the yeast strain is *Yarrowia lipolytica;* preferably, the down-regulated peroxisome biogenesis factor 10 is pex10 gene, the nucleotide sequence of which is shown in SEQ ID NO: 120;

preferably, the gene encoding a fatty acid elongase targeting the peroxisomes is cardamine mustard $CgKCS_{PTS}$ gene with an encoding sequence for the signal peptide targeting the peroxisomes, the nucleotide sequence of which is shown in SEQ ID NO: 125;

preferably, the gene encoding a fatty acid elongase is the *Mortierella alpina* C16/18 elongase gene MaLCE1 gene, the nucleotide sequence of which is shown in SEQ ID NO: 93;

preferably, the gene encoding a fatty acid elongase targeting the endoplasmic reticulum is cardamine mustard $CgKCS_{ER}$ gene with an encoding sequence for the signal peptide targeting the endoplasmic reticulum, the nucleotide sequence of which is shown in SEQ ID NO: 121;

preferably, the gene encoding a diglyceride acyltransferase targeting the endoplasmic reticulum is *Yarrowia lipolytica* $DGAT1_{ER}$ gene with an encoding sequence for the signal peptide targeting the endoplasmic reticulum, the nucleotide sequence of which is shown in SEQ ID NO: 122;

preferably, the gene encoding a Δ9 desaturase targeting the endoplasmic reticulum is the *Yarrowia lipolytica* $SCD_{ER}$ gene with an encoding sequence for the signal peptide targeting the endoplasmic reticulum, the nucleotide sequence of which is shown in SEQ ID NO: 123.

Preferably, the yeast is *Yarrowia lipolytica.*

The present invention provides a use of the recombinant yeast strain constructed according to any one of the above schemes for the preparation of microbial oil or nervonic acid. Specifically, it comprises but not limited to infant milk replacers, functional foods, medical foods, medical nutrition products, dietary supplements, pharmaceutical compositions, animal feeds, and personal care products containing the microbial oil or nervonic acid.

The present invention provides a method for preparing microbial oil and/or nervonic acid using the recombinant yeast strain constructed according to any one of the above technical schemes, which specifically comprises, but is not limited to, the cultivation of microorganisms and the optimization and control of fermentation conditions. The optimization of fermentation conditions comprises the optimization of different carbon sources, carbon-nitrogen ratios and the addition of erythrose at different growth periods, wherein the control of fermentation conditions comprises, but is not limited to, the control of temperature, pH, fermentation time, dissolved oxygen, and feeding methods and so on. The extraction process of the microbial oil or/and nervonic acid comprises, but is not limited to, the isolation, fragmentation and organic solvent extraction process of the strain.

Preferably, the method for preparing microbial oil comprises:

(a) cultivating any one of the recombinant yeast strains described in Scheme 1, Scheme 2, Scheme 3, Scheme 4, Scheme 5 and/or Scheme 6 of the present invention, wherein the microbial oil containing nervonic acid is produced; and (b) recovering the microbial oil of step (a).

Preferably, the method for preparing nervonic acid comprises:

(a) cultivating any one of the recombinant yeast strains described in Scheme 1, Scheme 2, Scheme 3, Scheme 4, Scheme 5, and/or Scheme 6 of the present invention, to produce microbial oil; and (b) recovering the microbial oil of step (a), and extracting nervonic acid.

Compared with the prior art, the present invention has beneficial effects: the method of the present invention involves the metabolic pathways and fermentation regulation of the nervonic acid synthesis system, and can obtain high-quality recombinant *Yarrowia lipolytica* strains, wherein the yield of microbial oil is increased, and the concent of nervonic acid prepared accounts for 39.6% of the total fatty acid content with a nervonic acid concentration of 16 g/L, which has good industrial application prospects.

It should be understood that within the scope of the present invention, the various technical features of the present invention above and the various technical features specifically described hereinafter (as in the embodiments) may be combined with each other to constitute a new or preferred technical solution. Due to space limitations, it is not repeated here.

A: PCR verification results of CgKCS genes of different transformants in the construction of strain YL1. B: PCR verification results of MaLCE1 genes of different transformants in the construction of strain YL2. C: PCR verification results of CgKCS genes of different transformants in the construction of strain YL2-1. D: PCR verification results of BtFAE1 genes of different transformants in the construction of strain YL2-2. E: PCR verification results of CgKCS genes of different transformants in the construction of strain YL2-3. F: PCR verification results of ScZwf genes of different transformants in the construction of strain YL2-4. G: PCR verification results of CgKCS genes of different transformants in the construction of strain YL3. H: PCR verification results of PLA2-1 genes of different transformants in the construction of strain YL4-1. I: PCR verification results of PLA2-2 genes of different transformants in the construction of strain YL4-2. J: PCR verification results of PLA2-3 genes of different transformants in the construction of strain YL4-3. K: PCR verification results of PLA2-4 genes of different transformants in the construction of strain YL4-4. L: PCR verification results of PLA2-5 genes of different transformants in the construction of strain YL4-5. M: PCR verification results of PLA2-6 genes of different transformants in the construction of strain YL4-6. N: PCR verification results of gELOVL6 genes of different transformants in the construction of strain YL5. O: PCR verification results of CgKCS genes of different transformants in the construction of strain YL6. P: PCR verification results of AtADS1 genes of different transformants in the construction of strain YL7. Q: PCR verification results of AtADS2 genes of different transformants in the construction of strain YL8. R: PCR verification results of pex10 genes of different transformants in the construction of strain YL9. S: PCR verification results of CgKCS genes of different transformants in the construction of strain YL10. T: PCR verification results of DGAT1 genes of different transformants in the construction of strain YL11.

Figure 3:
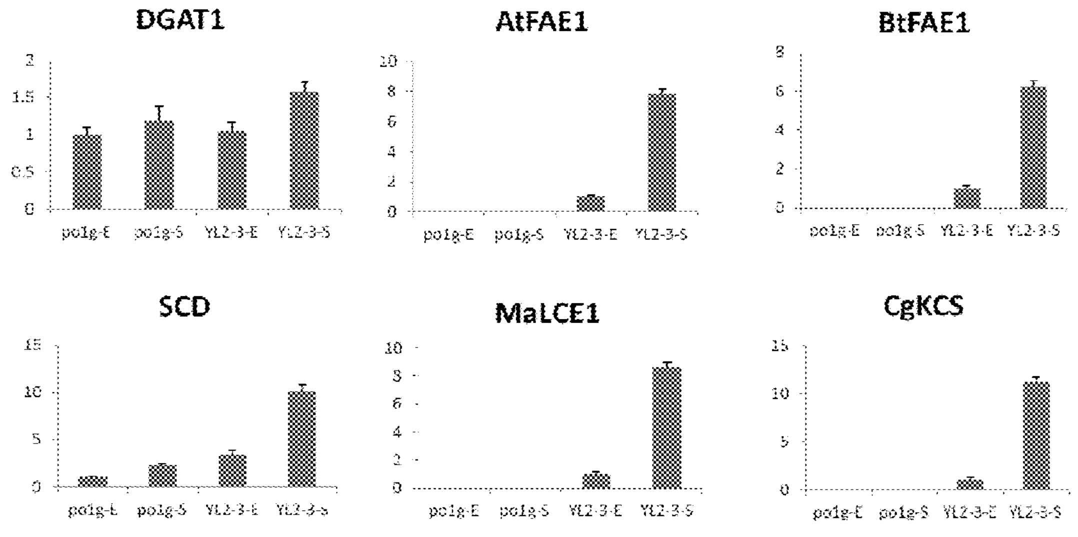

FIG. 3 is a diagram of the expression verification of the 6 genes in the YL2-3 strain provided in the example of the present invention.

Figure 4:
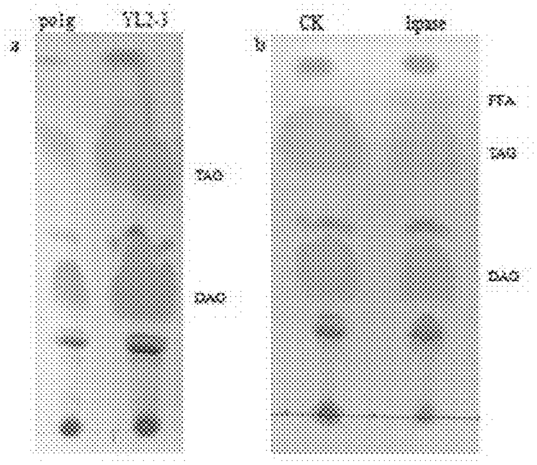

FIG. 4 shows the position specificity of nervonic acid in TAG analyzed by the TLC method provided in the example of the present invention.

Figure 5:
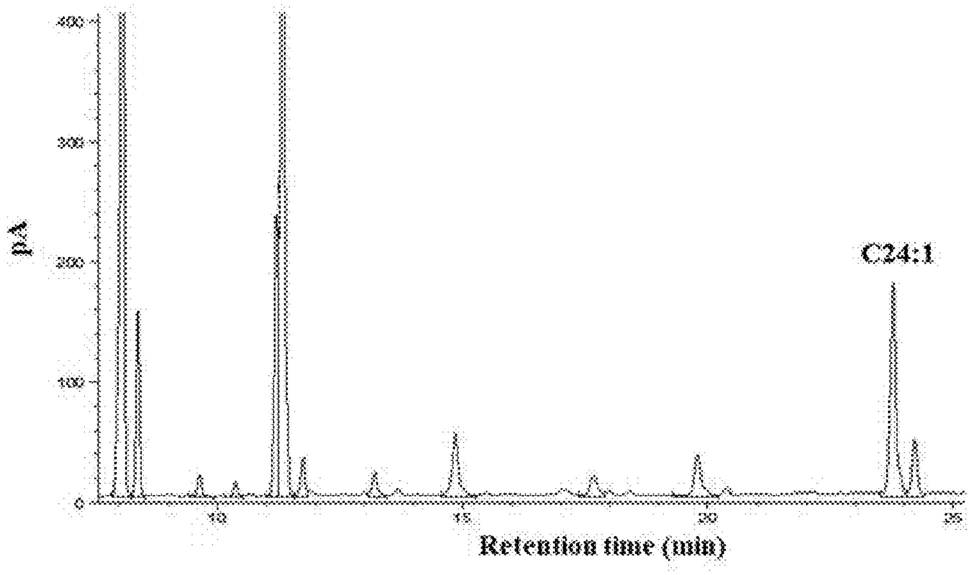

FIG. 5 is a analysis diagram showing the fatty acid compositions provided in the example of the present invention.

Figure 6:
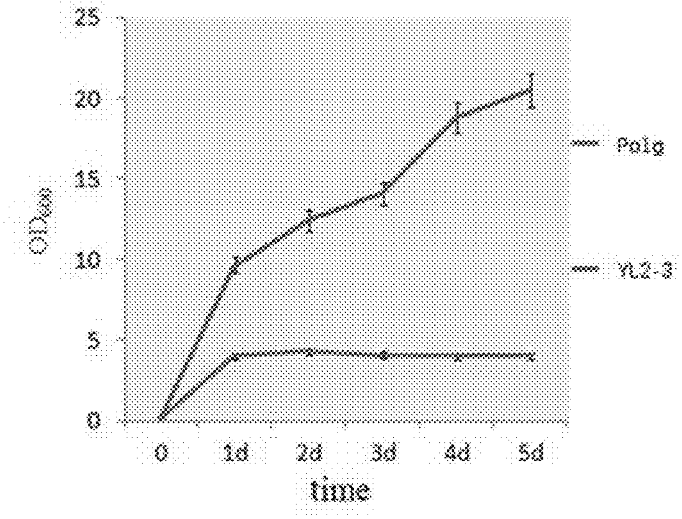

FIG. 6 is a growth curve of YL2-3 strain under the shaking flask fermentation conditions provided in the example of the present invention.

Figure 7:
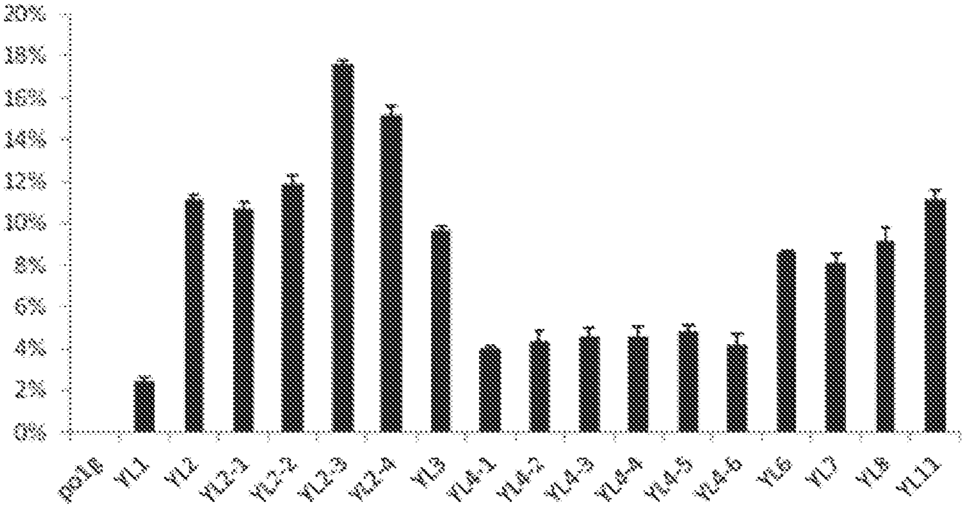

FIG. 7 is a graph showing the contents of nervonic acids of different strains under the shaking flask fermentation conditions provided in the example of the present invention.

Figure 8:
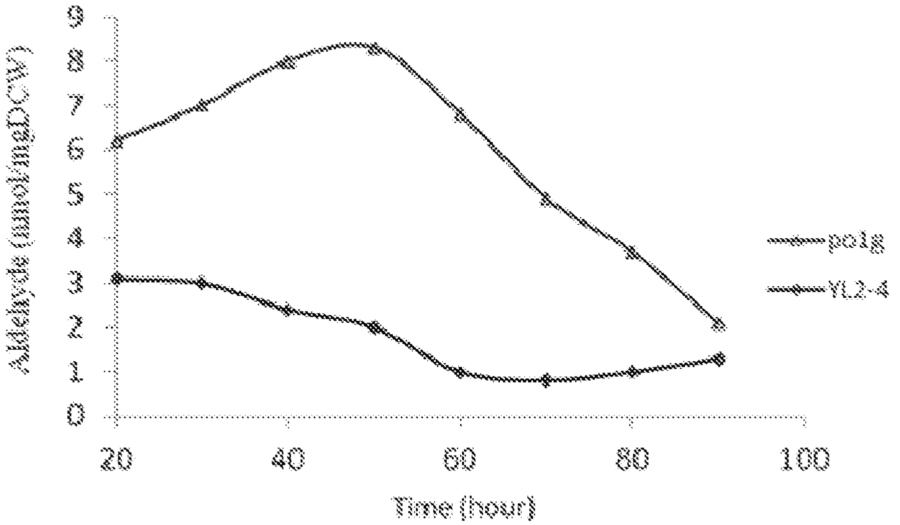

FIG. 8 shows the intracellular aldehyde levels in Po1g and YL2-4 strains provided in the example of the present invention.

Figure 9:
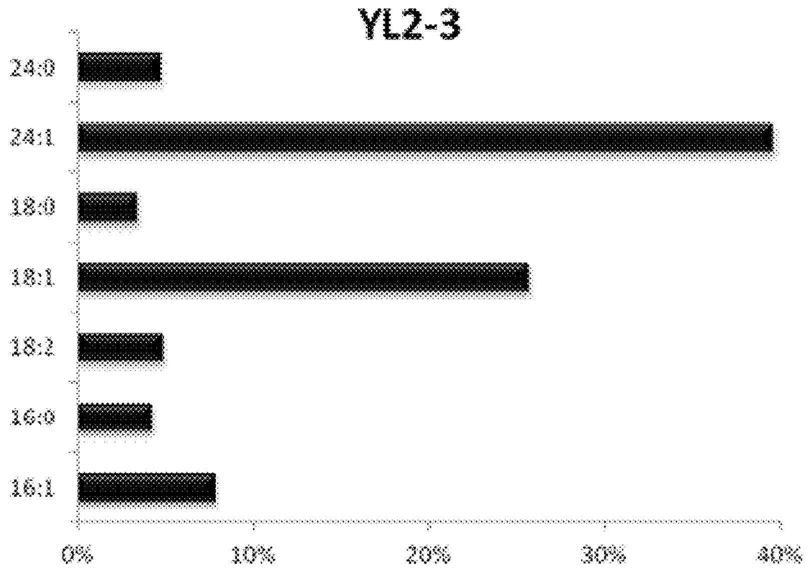

FIG. 9 shows the fatty acid compositions of strain YL2-3 under the amplifying fermentation conditions using the fermentor provided in the example of the present invention.

DETAILED DESCRIPTION

The following are definitions of terms involved in the present invention.

Desaturase refers to a polypeptide that can desaturate one or more fatty acids (i.e. introduce a double bond) to produce the fatty acid or precursor of interest. The Δ-system is used to count from the carboxyl end of the substrate to indicate the desaturase activity. Preferably, the desaturase of the present invention is a Δ9 desaturase, which desaturates fatty acids between the carbon atoms numbered $9^{th}$ and $10^{th}$ at the carboxyl end of the molecule. For example, it can catalyze the substrate fatty acid stearic acid (C18:0) to produce oleic acid (C18:1).

Fatty acid elongase refers to a polypeptide that can extend the carbon chain of a fatty acid to produce an acid that is 2 carbon atoms longer than the fatty acid substrate on which the elongase acts. Preferably, the fatty acid elongase of the present invention includes, but is not limited to, C16/18 elongase, C18/20 elongase, C20/22 elongase and C22/24 elongase. Usually, C16/18 elongase will use C16 substrates, such as *Mortierella alpina* C16/18 elongase gene MaLCE1, goat fatty acid elongase 6 gene gELOVL6. Some elongases have a wide range of specificities and therefore a single elongase can catalyze several elongase reactions. For example, cardamine mustard CgKCS not only has substrate specificity for C18 and C20 fatty acids, but also can continue to use C22 fatty acids as substrates. Therefore, CgKCS has C18/20, C20/22 and C22/24 elongase activities.

Diglyceride acyltransferase is an enzyme that catalyzes the last step of triacylglycerol ester (TAG) synthesis and is the only key enzyme and rate-limiting enzyme in the TAG synthesis process. Increasing the expression of diglyceride acyltransferase in yeast cells can increase the lipid content in the cells.

The endoplasmic reticulum, peroxisomes, and mitochondria refer to organelles that are ubiquitous in all eukaryotic cells. In order to express enzymes targeting the endoplasmic reticulum, peroxisomes, and mitochondria, the endoplasmic reticulum retention signal peptide KDEL, peroxisome targeting signal peptide SKL and mitochondrial targeting signal peptide CoxIV (MLSLRQSIRFFKPATRTLCSSRYLL) need to be added to the 3' end of the corresponding gene.

Peroxisome biosynthesis factor protein, namely peroxisome protein or Pex protein, refers to a protein involved in peroxisome biosynthesis and/or involved in the passage process of cell proteins through the peroxisome membrane by ATP hydrolysis.

An expression cassette refers to a DNA fragment containing the following sequences: the coding sequence of the selected gene and the regulatory sequences before (5' non-coding sequence) and after (3' non-coding sequence) the coding sequence required for the expression of the selected gene product. Expression cassettes are usually comprised in vectors to facilitate cloning and transformation. Different expression cassettes can be transformed into different organisms including bacteria, yeast, plants and mammalian cells, as long as the correct control sequences can be used for each host. The expression cassette usually consists of the following sequences:

1) a promoter sequence, such as GPAT, TEF1, EXP1, EYK1 and GPD, etc.;

2) a coding sequence; and 3) a 3' end non-translation region (i.e., terminator), which usually contains polyadenylic acid sites in eukaryotic cells, such as XPR2, LIP1t and PQX3t.

Microbial oil refers to a large amount of oil produced in the bacterial body by microorganisms such as yeast, mold, bacteria and algae under certain conditions, using carbohydrates, hydrocarbons or ordinary oils as carbon sources. The main components are triglycerides and free fatty acids. Preferably, the microbial oil of the present invention is produced by the fermentation of *Yarrowia lipolytica*. Through the regulation of metabolic pathways and fermentation processes, the ability of obtain high-quality strains to produce microbial oil is greatly improved, and the amount of nervonic acid prepared accounts for 39.6% of the total fatty acid content. Other fatty acids include, but are not limited to, palmitoleic acid, oleic acid, linoleic acid, palmitic acid, octadecanoic acid and tetracosanoic acid, etc.

The invention is further illustrated below in conjunction with specific embodiments. It should be understood that the examples are not intended to limit the scope of the invention. The experimental methods without specific conditions in the following examples are usually based on conventional conditions, for example the conditions described in (Sambrook and Russell et al. Molecular Cloning-A Laboratory Manual) (Third Edition) (2001) CSHL Publishing Company), or in accordance with the conditions recommended by the manufacturer. Unless otherwise stated, percentages and parts are calculated by weight. Unless otherwise stated, percentages and parts are calculated by weight. Unless otherwise specified, the experimental materials and reagents used in the following examples are commercially available.

The standard recombinant DNA technology and molecular cloning technology used in the examples are well-known in the art (Ausubel, F M et al., Current Protocols in Molecular Biology, published by Greene Publishing Assoc. and Wiley-Interscience), and materials and methods suitable for the growth of microorganisms are well known in the art. The main chemical reagents were purchased from KAPA Biosystems, New England Biolabs, TransGen Biotech, Thermo Fisher Scientific, OMEGA bio-tek, etc.

The present invention will be described in detail below in conjunction with specific embodiments.

Figure 1:
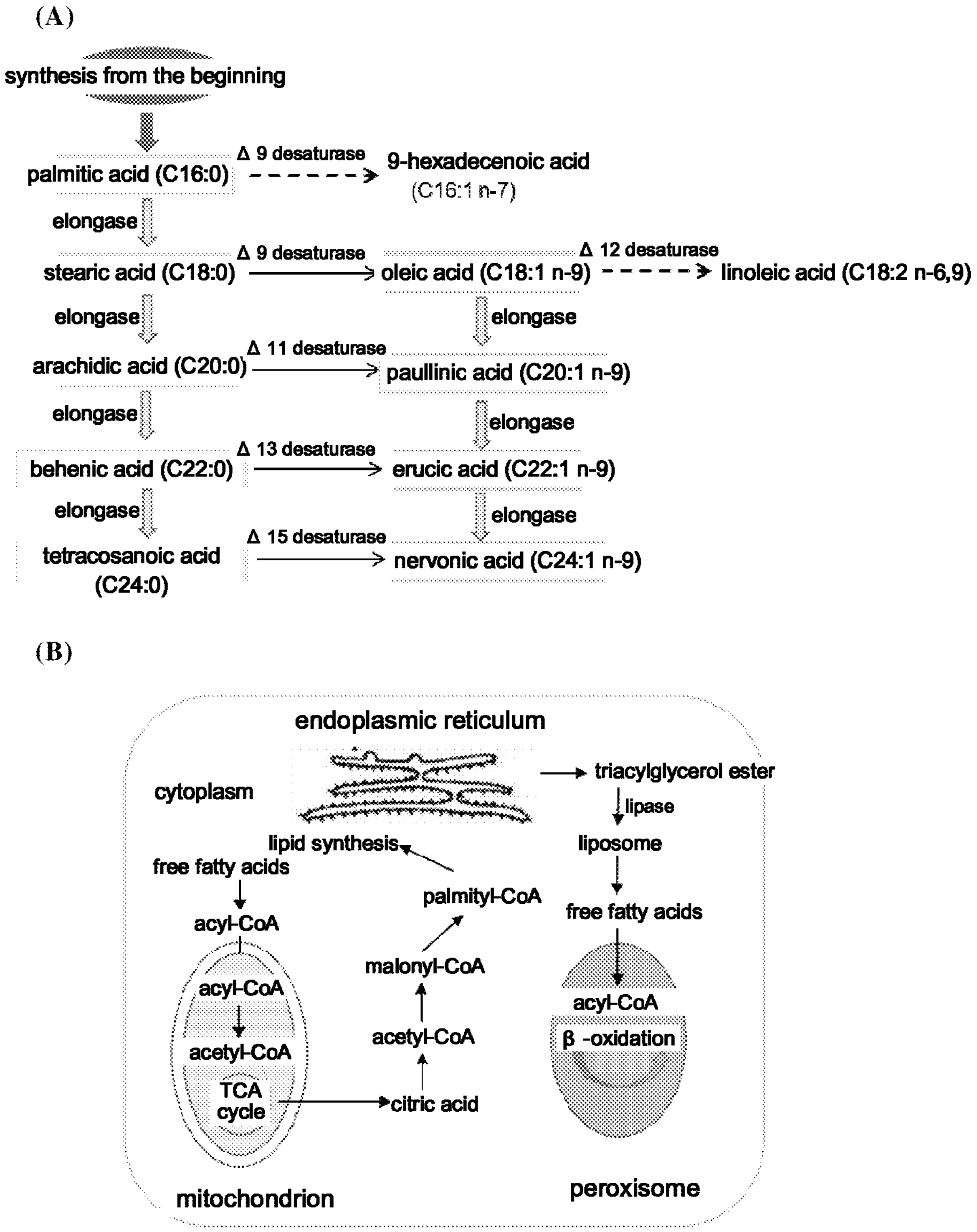
FIG. 1 is a diagram showing the nervonic acid synthesis strategy provided in the example of the present invention.

See FIG. 1 for a diagram showing the nervonic acid synthesis strategy provided in the example of the present invention.

Example 1. Plasmid Construction 1.1 Cloning of Genetic Elements

1) Acquisition of Genes DGAT1, SCD, PLA2-1, PLA2-2, PLA2-3, PLA2-4, PLA2-5, PLA2-6, ylGSR and ylGPO:

*Yarrowia lipolytica* strain (strain number was polg, purchased from Yeastern Biotech Company, Taiwan) was cultured in YPD medium (YPD medium components were glucose 20 g/L, peptone 20 g/L, yeast extract 10 g/L), and CTAB method (hexadecyltrimethylammonium bromide) was used to extract high-purity total genomic DNA. An appropriate amount of bacteria was added to liquid nitrogen to freeze, grinded into powder, and added with an appropriate amount of 2×CTAB extraction buffer (100 mmol/L Tris-HCl, pH8.0, 20 mmol/L EDTA, 1.4 mol/L NaCl, 2% (w/v) CTAB, 40 mmol/L mercaptoethanol), incubated at 65° C. for 10 minutes with intermittent shaking. Then an equal volume of chloroform/isoamyl alcohol was added, and the centrifuge tube was gently inverted to mix the mixture, centrifuged at 12000 rpm for 10 min at room temperature. The supernatant was transferred to another centrifuge tube, added with an equal volume of chloroform/isoamyl alcohol, and the centrifuge was inverted to mix the mixture and centrifuged at 12000 rpm for 10 minutes at room temperature. The upper aqueous phase was transferred to a new centrifuge tube, added with an equal volume of isopropanol to be mixed, and placed at room temperature for 30 minutes. The tube was centrifuged at 4000 rpm for 10 minutes. The supernatant was removed, and the precipitation was rinsed with 70% ethanol, added with 20 μl of TE buffer (100 mM Tris-HCl, 10 mM EDTA pH8.0) to dissolve the DNA after air drying, and stored at −20° C. for later use. The total DNA was partially digested with Sau3AI, and the digested DNA fragments were purified by electrophoresis. The gel recovery purification kit was used to recover fragments of approximately 2 to 6 kb. The recovered DNA was dissolved in 10 mmol/L Tris-HCl (pH 8.0), stored at −20° C.

The genomic DNA of *Yarrowia lipolytica* yeast was used as a template, and SEQ ID NO: 1-20 were used as the primer sequences. The genes were amplified using KAPA HiFi high-fidelity DNA polymerase (purchased from KAPA Biosystems) and PCR (Polymerase Chain Reaction, also known as polymerase chain reaction) amplifications were performed respectively. The amplification system was 25 ul, specifically comprising 12.5 ul of 2×KAPA Mix; 10 uM of primers, 0.5 ul for each; 1 ul of template; and water added to make up a totle volume of 25 ul. The amplification conditions were: 95° C. pre-denaturation for 3 minutes; 98° C. denaturation for 20 seconds, 60-72° C. annealing for 15 seconds, 72° C. extension with a extension time calculated as 30 seconds per kb, and the number of cycles was 29-35; and 72° C. extension for 10 minutes. Each gene sequence obtained was DGAT1 as shown in SEQ ID NO: 83, SCD as shown in SEQ ID NO: 84, PLA2-1 as shown in SEQ ID NO: 85, PLA2-2 as shown in SEQ ID NO: 86, PLA2-3 as shown in SEQ ID NO: 87, PLA2-4 as shown in SEQ ID NO: 88, PLA2-5 as shown in SEQ ID NO: 89, PLA2-6 as shown in SEQ ID NO: 90, ylGSR as shown in SEQ ID NO: 91 and ylGPO as shown in SEQ ID NO: 92.

2) The genes encoding exogenous fatty acid elongases were MaLCE as shown in SEQ ID NO: 93, AtFAE1 as shown in SEQ ID NO: 94, BtFAE1 as shown in SEQ ID NO: 95, CgKCS as shown in SEQ ID NO: 96, rELO2 as shown in SEQ ID NO: 97, CpLCE as shown in SEQ ID NO: 98, and gELOVL6 as shown in SEQ ID NO: 99, all obtained by Wuxi Qinglan Biotechnology Co., Ltd. through gene synthesis. Using SEQ ID NOs: 21-34 as the primer sequences can carry out PCR amplification of the above sequence.

3) The genes encoding exogenous fatty acid desaturases were D9DMB as shown in SEQ ID NO: 100, CeFAT6 as shown in SEQ ID NO: 101, MaOLE2 as shown in SEQ ID NO: 102, AtADS1 as shown in SEQ ID NO: 103, AtADS2 as shown in SEQ ID NO: 104, EcAldH as shown in SEQ ID NO: 105, and ScZwf as shown in SEQ ID NO: 106, all obtained by Wuxi Qinglan Biotechnology Co., Ltd. through gene synthesis. Using SEQ ID NOs: 35-48 as the primer sequences can carry out PCR amplification of the above sequence.

1.2 Cloning of Promoter and Terminator Elements

1) Cloning of GPAT, TEF1, EXP1, EYK1 and GPD Gene Promoters:

The genomic DNA of *Yarrowia lipolytica* was extracted by the above CTAB method, and the genomic DNA of *Yarrowia lipolytica* yeast was used as the template. SEQ ID NOs: 49-58 were used as the primer sequences, and KAPA HiFi high-fidelity DNA polymerase was used for the PCR amplification of promoters respectively. The amplification system of each was 25 ul, and the amplification conditions and the amount of amplification system were the same as those described in step 1) above. The promoter genes obtained were GPAT as shown in SEQ ID NO: 107, TEF1 as shown in SEQ ID NO: 108, EXP1 as shown in SEQ ID NO: 109, EYK1 as shown in SEQ ID NO: 110, and GPD as shown in SEQ ID NO: 111.

2) Cloning of XPR2, LIP1t and PQX3t Terminators:

Similar to the cloning of the promoters, the genomic DNA of *Yarrowia lipolytica* was used as the template, and SEQ ID NOs: 59-64 were used as the primer sequences. The terminators were amplified using KAPA HiFi high-fidelity DNA polymerase, and PCR amplifications were performed respectively. The amplification system of each was 25 ul, and the amplification conditions and the amount of amplification system were the same as those described in step 1) above. The terminator sequences obtained were XPR2 as shown in SEQ ID NO: 112, LIP1t as shown in SEQ ID NO: 113, and PQX3t as shown in SEQ ID NO: 114.

1.3 Cloning of Screening Marker Gene Elements

1) Cloning of Hygromycin Resistance Gene

The hygromycin (Hgr) resistance screening marker gene was obtained using the plasmid pAG32 (purchased from EUROSCARF) as the template, and using SEQ ID NOs: 65-66 as the primer sequences, and by PCR amplification using KAPA HiFi high-fidelity DNA polymerase. The amplification system was 25 ul, and the amplification conditions and the amount of amplification system were the same as those described in step 1) above. The hygromycin (Hgr) resistance screening marker gene obtained by PCR amplification was shown in SEQ ID NO: 115.

2) Acquisition of Leucine Synthesis Gene (LEU) and Key Gene of Uracil Synthase (URA3)

The genomic DNA of *Yarrowia lipolytica* was extracted by the above CTAB method, and the obtained genomic DNA was used as the template. SEQ ID NOs: 67-70 were used as the primer sequences, and KAPA HiFi high-fidelity DNA polymerase was used for the PCR amplification. The amplification system was 25 ul, and the amplification conditions and the amount of amplification system were the same as those described in step 1) above. Genes obtained by PCR amplification were gene LEU as shown in SEQ ID NO: 116 and gene URA3 as shown in SEQ ID NO: 117, respectively.

1.4 Cloning of DNA Homologous Recombination Fragments

In order to regulate the low expression level of pex10, homologous replacement (Verbeke J, Beopoulos A, Nicaud JM. Efficient homologous recombination with short length flanking fragments in Ku70 deficient *Yarrowia lipolytica* strains. Biotechnology Letters, 2013, 35(4): 571-576.) method was used to knock out genes. According to the *Yarrowia lipolytica* genome sequence, the DNA sequence of pex10 gene was searched, and the upstream and downstream sequences (about 1000 bp) of the target gene were selected. The genomic DNA of *Yarrowia lipolytica* was extracted by CTAB method and the obtained genomic DNA was used as the template. SEQ ID NOs: 71-78 were used as primer sequences, and KAPA HiFi high-fidelity DNA polymerase was used. The reaction system was 25 ul. The homologous recombination fragments obtained by PCR amplification were pex10-up as shown in SEQ ID NO: 118 and pex10-dow as shown in SEQ ID NO: 119, respectively.

The amplification conditions were: 95° C. pre-denaturation for 3 minutes; 98° C. denaturation for 20 seconds, 60-72° C. annealing for 15 seconds, 72° C. extension with a extension time calculated as 15 seconds per kb, and the number of cycles was 29-35; and 72° C. extension for 6 minutes.

1.5 Assembly and Construction of Plasmids

All plasmids were constructed with plasmid pYLEX1 (purchased from Yeastern Biotech Company, Taiwan) as the basic skeleton, using KAPA HiFi high-fidelity DNA polymerase, in a 25 ul reaction system. The plasmid basic skeleton fragments, target genes, promoters, terminators, screening marker genes were amplified by PCR amplification, and using Gibson Assembly method (Gibson DG. Synthesis of DNA fragments in yeast by one-step assembly of overlapping oligonucleotides. Nucleic Acids Research. 2009, 37(20): 6984-6990.) and kits (purchased from New England Biolabs), the pYLEX1 plasmid skeleton was assembled with the target gene, promoter, terminator and screening marker gene into a complete plasmid (see Table 1). Each plasmid contains a screening marker gene, one to three target genes, and each target gene has a promoter and a terminator.

The construction of pDGAT1 plasmid was taken as an example:

1) Plasmid pYLEX1 was used as the basic skeleton. pYLEX1 and *Yarrowia lipolytica* genomic DNA was used as the templates, respectively. SEQ ID NOs: 51-52, SEQ ID NOs: 59-60, SEQ ID NOs: 79-80 were used as primer sequences. PCR amplification of plasmid skeleton fragment, TEF promoter fragment and XPR2 terminator fragment were carried out, and the three DNA fragments were assembled using Gibson Assembly method to obtain plasmid pYLEX1-$P_{TEF1}$-$T_{XPR2}$. The DNA fragment concentration was controlled at 100-200 ng per reaction. The reaction system was 10 microliters, and the assembly conditions were 50° C. for 1 hour. After the reaction, 2 microliters of the reaction solution was taken to be transformed into DH5a competent cells (purchased from TransGen Biotech), and positive clones were obtained by colony PCR and DNA sequencing verification screening.

2) pYLEX1-$P_{TEF1}$-$T_{XPR2}$ and *Yarrowia lipolytica* genomic DNA were used as templates, and SEQ ID NOs: 1-2, SEQ ID NOs: 81-82 were used as primer sequences. PCR amplifications of the plasmid skeleton fragment with the promoter and the terminator, and the DGAT1 gene were carried out, and the two fragments were assembled together using the Gibson Assembly method to obtain the plasmid pYLEX1-PT-DGAT1, denoted as pDGAT1.

The constructions of the plasmids listed in Table 1 were similar to the assembly of the pDGAT1 plasmid. That is, the Gibson Assembly method was used to integrate the target gene, promoter, terminator and screening marker gene into one plasmid. Targeting genes expressed in the endoplasmic reticulum, peroxisomes and mitochondria required the addition of the endoplasmic reticulum retention signal peptide KDEL, peroxisome targeting signal peptide SKL and mitochondrial targeting signal peptide CoxIV (MLSLRQSIRFFKPATRTLCSSRYLL) to the 3'end of the corresponding genes.

TABLE 1

Description of the constructed plasmids of the present invention

| plasmid name | promoter | gene | source | terminator |
|---|---|---|---|---|
| pDGAT1 | TEF1 | DGAT1, | *Y. lipolytica* | XPR2 |
| | | Hgr (marker) | plasmid pAG32 | |
| pDS | TEF1 | DGAT1 | *Y. lipolytica* | XPR2 |
| | GPD | SCD | *Y. lipolytica* | LIP1T |
| | | Hgr (marker) | plasmid pAG32 | |
| PAtFAE1 | GPD | AtFAE1 | *Arabidopsis thaliana* | LIP1T |
| | | LEU (marker) | *Y. lipolytica* | |
| pAB | GPD | AtFAE1 | *Arabidopsis thaliana* | LIP1T |
| | TEF1 | BtFAE1 | *Brassica tournefortii* | XPR2 |
| | | LEU (marker) | *Y. lipolytica* | |
| pCgKCS | TEF1 | CgKCS | *Cardamine graeca* | XPR2 |
| | | URA (marker) | *Y. lipolytica* | |
| $pCgKCS_{ER}$ | TEF1 | $CgKCS_{ER}$ | *Cardamine graeca* | XPR2 |
| | | URA (marker) | *Y. lipolytica* | |
| $pCgKCS_{PTS}$ | TEF1 | $CgKCS_{PTS}$ | *Cardamine graeca* | XPR2 |
| | | URA (marker) | *Y. lipolytica* | |
| $pCgKCS_{MTS}$ | GPD | $CgKCS_{MTS}$ | *Cardamine graeca* | LiP1T |
| | | URA (marker) | *Y. lipolytica* | |
| $PC_{ER}C_{MTS}$ | TEF1 | $CgKCS_{ER}$ | *Cardamine graeca* | XPR2 |
| | GPD | $CgKCS_{MTS}$ | *Cardamine graeca* | LIP1T |
| | | URA (marker) | *Y. lipolytica* | |
| $PC_{ER}M$ | TEF1 | $CgKCS_{ER}$ | *Cardamine graeca* | XPR2 |
| | GPD | MaLCE1 | *Mortierella alpina* | LIP1T |
| | | URA (marker) | *Y. lipolytica* | |
| pMCSD | GPD | MaLCE1 | *Mortierella alpina* | LIP1T |
| | TEF1 | $CgKCS_{ER}$ | *Cardamine graeca* | XPR2 |
| | TEF1 | $DGAT1_{ER}$ | *Y. lipolytica* | XPR2 |
| | GPD | $SCD_{ER}$ | *Y. lipolytica* | LIP1T |
| | | URA (marker) | *Y. lipolytica* | |
| pCB | TEF1 | $CgKCS_{ER}$ | *Cardamine graeca* | XPR2 |
| | GPAT | $BtFAE1_{ER}$ | *Brassica tournefortii* | POX3T |
| | EXP1 | $CgKCS_{PTS}$ | *Cardamine graeca* | XPR2 |
| | TEF1 | $BtFAE1_{PTS}$ | *Brassica tournefortii* | XPR2 |
| | | URA (marker) | *Y. lipolytica* | |
| pPLA2-1 | TEF1 | PLA2-1 | *Y. lipolytica* | XPR2 |
| | | URA (marker) | *Y. lipolytica* | |
| pPLA2-2 | TEF1 | PLA2-2 | *Y. lipolytica* | XPR2 |
| | | URA (marker) | *Y. lipolytica* | |
| pPLA2-3 | TEF1 | PLA2-3 | *Y. lipolytica* | XPR2 |
| | | URA (marker) | *Y. lipolytica* | |
| pPLA2-4 | TEF1 | PLA2-4 | *Y. lipolytica* | XPR2 |
| | | URA (marker) | *Y. lipolytica* | |
| pPLA2-5 | TEF1 | PLA2-5 | *Y. lipolytica* | XPR2 |
| | | URA (marker) | *Y. lipolytica* | |
| pPLA2-6 | TEF1 | PLA2-6 | *Y. lipolytica* | XPR2 |
| | | URA (marker) | *Y. lipolytica* | |
| pylGSR | TEF1 | ylGSR | *Y. lipolytica* | XPR2 |
| | | URA (marker) | *Y. lipolytica* | |
| pylGPO | TEF1 | ylGPO | *Y. lipolytica* | XPR2 |
| | | URA (marker) | *Y. lipolytica* | |
| prELO2 | TEF1 | rELO2 | *Rattus norvegicus* | XPR2 |
| | | URA (marker) | *Y. lipolytica* | |
| pCpLCE | TEF1 | CpLCE | *Cryptosporidium parvum* | XPR2 |
| | | URA (marker) | *Y. lipolytica* | |

TABLE 1-continued

Description of the constructed plasmids of the present invention

| plasmid name | promoter | gene | source | terminator |
| --- | --- | --- | --- | --- |
| pgELOVL6 | EYK1 | gELOVL6 URA (marker) | *Capra hircus* *Y. lipolytica* | XPR2 |
| pMaKCS | TEF1 | MaKCS URA (marker) | *Mychonastes afer* *Y. lipolytica* | XPR2 |
| pD9DMB | TEF1 | D9DMB URA (marker) | *Cunninghamella echinulata* *Y. lipolytica* | XPR2 |
| pCeFAT6 | TEF1 | CeFAT6 URA (marker) | *Caenorhabditis elegans* *Y. lipolytica* | XPR2 |
| pMaOLE2 | TEF1 | MaOLE2 URA (marker) | *Mortierella alpina* *Y. lipolytica* | XPR2 |
| pAtADS1 | TEF1 | AtADS1 URA (marker) | *Arabidopsis thaliana* *Y. lipolytica* | XPR2 |
| pAtADS2 | TEF1 | AtADS2 URA (marker) | *Arabidopsis thaliana* *Y. lipolytica* | XPR2 |
| pEcAldH | TEF1 | EcAldH URA (marker) | *Escherichia coli* *Y. lipolytica* | XPR2 |
| pScZwf | TEF1 | ScZwf URA (marker) | *Saccharomyces cerevisiae* *Y. lipolytica* | XPR2 |
| pΔpex10 | | Δpex10 URA (marker) | *Y. lipolytica* *Y. lipolytica* | |

Note:
The marker in Table 1 is a mark.

Example 2. Construction of Engineered *Yarrowia lipolytica* Strain 2.1 Acquisition of the Expression Cassette NotI endonuclease (purchased from Thermo Fisher Scientific) was used to digest the plasmids pDS, pAB, pCgKCS, pCgKCS$_{ER}$, pCgKCS$_{PTS}$, pCgKCS$_{MTS}$, pC$_{ER}$ C$_{MTS}$, pMCSD, pCB, pPLA2-1, pPLA2-2, pPLA2-3, pPLA2-4, pPLA2-5, pPLA2-6, pylGSR, pylGPO, preELO2, pCpLCE, pgELOVL6, pMaKCS, pD9DMB, pCeFAT6, pMaOLE2, pAtADS1, pAtADS2, pEcAldH, pScZwf and pApex10 recorded in Table 1, respectively.

The specific enzyme digestion system comprised: 10×FD Green Buffer, 2 ul; NotI, 1 ul; Plasmid, <1 μg; ddH$_2$O to make up to 20 ul. The digested products were purified and recovered using Cycle Pure Kit (purchased from OMEGA bio-tek). The recovery steps were as follows. 4-5 times the volume of buffer CP was added into the digested product. The mixture was transfer to the DNA adsorption column after being mixed, and centrifuged at 13,000 g at room temperature. The filtrate was discarded and the precipitate was added with 700 μL DNA washing buffer and centrifuged at 13,000 g for 1 minute. The filtrate was discarded and the washing was repeated. The filtrate was discarded, and the empty adsorption column was centrifuged at 13,000 g for 2 minutes. The column was dried. The adsorption column was transferred to a clean 1.5 mL centrifuge tube, added with 30-50 μL of elution buffer, and centrifuged at 13,000 g to elute DNA.

The expression cassette DGAT1-SCD-Hgr or AtFAE1-BtFAE1-LEU or CgKCS-URA or CgKCS$_{ER}$-URA or CgKCS$_{PTS}$-URA or CgKCS$_{MTS}$-URA, CgKCS$_{ER}$-CgKCS$_{MTS}$-URA or MaLCE1-CgKCS$_{ER}$-DGAT1$_{ER}$-SCD$_{ER}$-URA or CgKCS$_{ER}$-BtFAE1$_{ER}$-CgKCS$_{PTS}$-BtFAE1$_{PTS}$-URA or PLA2-1-URA or PLA2-2-URA or PLA2-3-URA or PLA2-4-URA or PLA2-5-URA or PLA2-6-URA or ylGSR-URA or ylGPO-URA or rELO2-URA or CpLCE-URA or gELOVL6-URA or MaKCS-URA or D9DMB-URA or CeFAT6-URA or MaOLE2-URA or AtADS1-URA or AtADS2-URA or EcAldH-URA or ScZwf-URA or Δpex10-URA was obtained.

2.2 Transformation of *Yarrowia lipolytica*

(1) Cultivation. A single colony of the strain polg from the YPD plate medium was taken and inoculated in a 250 ml shake flask containing 50 ml of YPD medium (YPD medium components were glucose 20 g/L, peptone 20 g/L, yeast extract 10 g/L), cultured at 28° C. overnight. The above-mentioned cultured bacteria solution was inoculated into a 250 ml shake flask containing 50 ml YPD, to a final concentration of OD$_{600}$=0.5, and then cultured at 28° C. until OD$_{600}$ was 1.0, which took about 4 h.

(2) Transformation. 4 ml of the above cells were taken, and centrifuged at 5000 rpm for 3 min. The supernatant was discarded, and 1 μg of linearized gene expression cassette DNA was added, which was respectively DGAT1-SCD-Hgr or AtFAE1-BtFAE1-LEU or CgKCS-URA or CgKCS$_{ER}$-URA or CgKCS$_{PTS}$-URA or CgKCS$_{MTS}$-URA, CgKCS$_{ER}$-CgKCS$_{MTS}$-URA or MaLCE1-CgKCS$_{ER}$-DGAT1$_{ER}$-SCD$_{ER}$-URA or CgKCS$_{ER}$-BtFAE1$_{ER}$-CgKCS$_{PTS}$-BtFAE1$_{PTS}$-URA or PLA2-1-URA or PLA2-2-URA or PLA2-3-URA or PLA2-4-URA or PLA2-5-URA or PLA2-6-URA or ylGSR-URA or ylGPO-URA or rELO2-URA or CpLCE-URA or gELOVL6-URA or MaKCS-URA or D9DMB-URA or CeFAT6-URA or MaOLE2-URA or AtADS1-URA or AtADS2-URA or EcAldH-URA or ScZwf-URA or Δpex10-URA. Meanwhile, 90 μl of 50% PEG3350, 5 μl of 2M LiAC, 5 μl of 2M DTT, 2 μl of DMSO, 2.5 μl of Salman liner DNA (10 mg/ml) were added, and the solution was incubated in a 30° C. water bath for 1 h, followed with vortex and shake, then incubated in a 39° C. water bath for 10 minutes. 50 μl of the mixture of the transformation system was taken and directly applied to the screening plate. The YPD screening plates were Hgr (150 μg/ml), URA selection defective medium and LEU selection defective medium, respectively.

2.3 Engineered Strains

Figure 2:
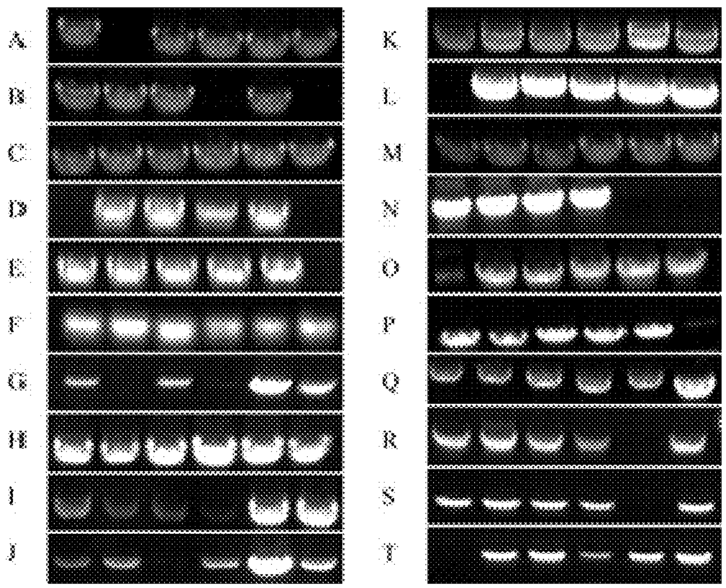
FIG. 2 shows the PCR identification of yeast transformants provided in the example of the present invention.

A single colony was taken from the screening plate, and PCR was used to verify the transformation results (FIG. 2), and RT-PCR was used to verify gene expression levels (FIG. 3 and Table 2). Positive transformants were screened and engineered strains YL1, YL2, YL2-1, YL2-2, YL2-3, YL2-4, YL3, YL4-1, YL4-2, YL4-3, YL4-4, YL4-5, YL4-6, YL6, YL7, YL8 and YL11 were obtained.

The PCR verification method was as follows. The corresponding DNA of the *Yarrowia lipolytica* transformant was used as the template, and the corresponding primers were used for PCR amplification. The amplification system was 25 ul, specifically comprising 2×Taq Mix, 12.5 ul; 10 uM primer, 0.5 ul for each; template 1 ul; water added to make up to 25 ul. Amplification conditions were: 94° C. predenaturation for 5 minutes; 94° C. denaturation for 30 seconds, 60-72° C. annealing for 30 seconds, 72° C. extension, with a extension time calculated as 1 minute per kb, and the number of cycles was 30; extended at 72° C. for 10 minutes. Detection by 1% agarose gel electrophoresis was performed after amplification.

The method of RT-PCR to verify the gene expression level was as follows. The total RNA of the above-mentioned strain was extracted by the TRizol method, and the concentration was detected by the nucleic acid analyzer ND-1000. Meanwhile the RNA degradation was detected by 1% agarose gel electrophoresis. According to the sequence of each gene, specific primers for real-time PCR were designed. Qualified RNA was reverse transcribed into cDNA and then real time-PCR was performed. For the specific steps of the real time-PCR method, see Biotium's EvaGreen® Master Mixes for qPCR quantitative detection kit. Real time-PCR amplification was completed by the Light Cycler 480 real-time PCR system produced by Roche, USA. Three replicate wells were set for each sample, and different samples were repeated three times, and the Actin gene of *Yarrowia lipolytica* was used as an internal control. Finally, the relative expression amount was calculated according to the $2^{-\Delta\Delta Ct}$ method.

On the basis of YL2, strain YL2-1 was obtained by transforming the expression cassette $CgKCS_{ER}$-URA derived from plasmid $pCgKCS_{ER}$. That is, on the basis of YL2, strain YL2-1 further overexpressed gene $CgKCS_{ER}$.

On the basis of YL2, strain YL2-2 was obtained by transforming the expression cassette $CgKCS_{ER}$-$BtFAE1_{ER}$-$CgKCS_{PTS}$-$BtFAE1_{PTS}$-URA derived from plasmid pCB. That is, on the basis of YL2, strain YL2-2 further overexpressed genes CgKCS and BtFAE1, in different organelles (endoplasmic reticulum, peroxisome).

On the basis of YL2, strain YL2-3 was obtained by transforming the expression cassette MaLCE1-$CgKCS_{ER}$-$DGAT1_{ER}$-$SCD_{ER}$-URA derived from plasmid pMCSD. That is, on the basis of YL2, strain YL2-3 further overexpressed genes MaLCE1, $CgKCS_{ER}$, $DGAT1_{ER}$ and $SCD_{ER}$. This strain was preserved in the China General Microbiological Culture Collection Center, and the preservation number is CGMCC NO. 15309.

On the basis of YL2, strain YL2-4 was obtained by transforming the expression cassettes EcAldH-URA, ScZwf-URA, ylGSR-URA and ylGPO-URA derived from plasmids pEcAldH, pScZwf, pylGSR and pylGPO. That is, on the basis of YL2, strain YL2-4 further overexpressed genes EcAldH, ScZwf, ylGSR and ylGPO.

According to the above text, strain YL3 was obtained by transforming the expression cassettes $CgKCS_{PTS}$-URA and MaLCE1-$CgKCS_{ER}$-$DGAT1_{ER}$-$SCD_{ER}$-URA derived from the plasmids $pCgKCS_{PTS}$ and pMCSD, that is, overexpressing genes $CgKCS_{PTS}$, MaLCE1, $CgKCS_{ER}$, $DGAT1_{ER}$ and $SCD_{ER}$.

TABLE 2

Gene expression levels in different strains in the stable phase

| strain | gene expression levels of mutant/control strains | | | | |
|---|---|---|---|---|---|
| YL1 | CgKCS (+) | BtFAE1 (+) | DGAT1 (3.2) | SCD (1.4) | AtFAE1 (+) |
| YL2 | CgKCS (4.5) | MaLCE1 (+) | DGAT1 (3.5) | SCD (1.9) | |
| YL2-1 | CgKCS (5.9) | | | | |
| YL2-2 | CgKCS (8.5) | BtFAE1 (5.5) | | | |
| YL2-4 | EcAldH (+) | ScZwf (+) | ylGSR (+) | ylGPO (+) | |
| YL3 | CgKCS (5.5) | MaLCE1 (+) | DGAT1 (2.9) | SCD (2.1) | |
| YL4-1 | PLA2-1 (2.5) | | | | |
| YL4-2 | PLA2-2 (5.1) | | | | |
| YL4-3 | PLA2-3 (9.5) | | | | |
| YL4-4 | PLA2-4 (3.5) | | | | |
| YL4-5 | PLA2-5 (5.9) | | | | |
| YL4-6 | PLA2-6 (2.5) | | | | |
| YL5 | gELOVL6 (+) | MaOLE2 (+) | | | |
| YL6 | CgKCS (7.5) | | | | |
| YL7 | AtADS1 (+) | | | | |
| YL8 | AtADS2 (+) | | | | |
| YL10 | CgKCS (+) | | | | |
| YL11 | CgKCS (8.5) | MaLCE1 (+) | DGAT1 (4.5) | SCD (2.5) | |

Note:
The number in ( ) indicates the multiple of up-regulation of the gene level; and + indicates that the gene level was up-regulated.

According to the above text, strain YL1 was obtained by transforming the expression cassettes DGAT1-SCD-Hgr, AtFAE1-BtFAE1-LEU and CgKCS-URA derived from plasmids pDS, pBA and pCgKCS, that is, overexpressing of genes DGAT1 and SCD, and overexpressing of exogenous genes AtFAE1, BtFAE1 and CgKCS.

On the basis of YL1, strain YL2 was obtained by transforming the expression cassette MaLCE1-$CgKCS_{ER}$-$DGAT1_{ER}$-$SCD_{ER}$-URA derived from plasmid pMCSD. That is, on the basis of YL1, strain YL2 further overexpressed genes MaLCE1, $CgKCS_{ER}$, $DGAT1_{ER}$ and $SCD_{ER}$.

On the basis of YL1, strain YL4-1 was obtained by transforming the expression cassette PLA2-1-URA derived from the plasmid pPLA2-1. That is, on the basis of YL1, strain YL4-1 further overexpressed gene PLA2-1.

On the basis of YL1, strain YL4-2 was obtained by transforming the expression cassette PLA2-2-URA derived from plasmid pPLA2-2. That is, on the basis of YL1, strain YL4-2 further overexpressed gene PLA2-2.

On the basis of YL1, strain YL4-3 was obtained by transforming the expression cassette PLA2-3-URA derived from plasmid pPLA2-3. That is, on the basis of YL1, strain YL4-3 further overexpressed gene PLA2-3.

On the basis of YL1, strain YL4-4 was obtained by transforming the expression cassette PLA2-4-URA derived from plasmid pPLA2-4. That is, on the basis of YL1, strain YL4-4 further overexpressed gene PLA2-4.

On the basis of YL1, strain YL4-5 was obtained by transforming the expression cassette PLA2-5-URA derived from plasmid pPLA2-5. That is, on the basis of YL1, strain YL4-5 further overexpressed gene PLA2-5.

On the basis of YL1, strain YL4-6 was obtained by transforming the expression cassette PLA2-6-URA derived from plasmid pPLA2-6. That is, on the basis of YL1, strain YL4-6 further overexpressed gene PLA2-6.

Strain YL5 was obtained by transforming the expression cassettes gELOVL6-URA and MaOLE2-URA derived from plasmids pgELOVL6 and pMaOLE2, that is, overexpressing exogenous genes gELOVL6 and MaOLE2.

On the basis of YL5, strain YL6 was obtained by transforming the expression cassette $CgKCS_{ER}$-$CgKCS_{MTS}$-URA derived from the plasmid $pC_{ER}C_{MTS}$. That is, on the basis of YL5, strain YL6 further overexpressed genes $CgKCS_{ER}$ and $CgKCS_{MTS}$.

On the basis of YL1, strain YL7 was obtained by transforming the expression cassette AtADS1-URA derived from pAtADS1. That is, on the basis of YL1, strain YL7 further overexpressed gene AtADS1.

On the basis of YL1, strain YL8 was obtained by transforming the expression cassette AtADS2-URA derived from pAtADS2. That is, on the basis of YL1, strain YL8 further overexpressed gene AtADS2.

According to the above text, strain YL9 was obtained by transforming the expression cassette Δpex10-URA derived from the plasmid pΔpex10, that is, knocking out gene pex10.

On the basis of YL9, strain YL10 was obtained by transforming the expression cassette $CgKCS_{PTS}$-URA derived from plasmid $pCgKCS_{PTS}$. That is, on the basis of YL9, strain YL10 further overexpressed gene $CgKCS_{PTS}$.

On the basis of YL10, strain YL11 was obtained by transforming the expression cassette MaLCE1-$CgKCS_{ER}$-$DGAT1_{ER}$-$SCD_{ER}$-URA derived from plasmid pMCSD. That is, on the basis of YL10, strain YL11 further overexpressed genes MaLCE1, $CgKCS_{ER}$, $DGAT1_{ER}$ and $SCD_{ER}$.

Example 3. Strain Cultivation and Nervonic Acid Production 3.1 Shake Flask Culture and Induction Regulation for the Strain a. Strains polg and YL2-3 were activated on the YPD solid plate respectively, and cultured at 28° C. for 1 day. Single colony was picked and inoculated into 250 ml shake flasks containing 50 ml YPD medium respectively, and cultivated at 28° C. for 1 day for seed culture solution. The seed culture solution was respectively inoculated into 250 ml shake flasks containing 50 ml YNB medium to make the initial $OD_{600}$ as 0.2, cultured at 28° C. for 6 days, and set aside.

Wherein, the compositions of YNB medium were YNB1.7 g/L, glucose 80 g/L, yeast extract 1.5 g/L, uracil 20 mg/L, and leucine 100 mg/L.

b. The seed culture solution cultivated by the above method was respectively inoculated into 250 ml shake flasks containing 50 ml induction medium to make the initial $OD_{600}$ as 0.2, cultured at 28° C. for 6 days, and set aside.

Wherein, the induction medium was YNB containing 10 g/L glucose. After 1 day of culture, when the glucose was almost completely consumed, erythritol was added as a carbon source. Then after 2 days of culture, glucose was added.

3.2 Strain Culture in Fermentation Tank (Strain YL2-3 as an Example)

The strain YL2-3 obtained above was activated and used as a seed liquid, and 3 L medium YNBF was added to a 5 L fermentor, and the dissolved oxygen in the fermentation control was greater than 20% (growth period: 0-48 h) and 0-5% (stable period). During the fermentation process, the pH value was constantly controlled at 5.5 until the end of the fermentation. The temperature was controlled at 28° C. and it was incubated for 6 days.

Wherein, the compositions of YNBF medium were 3.4 g/L yeast nitrogen source without amino acids and ammonium sulfate, 150 g/L glucose, 2 g/L yeast extract and 8.8 g/L ammonium sulfate. The inoculation amount was 10%.

3.3 Extraction of Microbial Oil 5 ml of the culture solution obtained above was taken and centrifuged. 1 g of wet bacteria was added with 10 ml of 4 mol/L hydrochloric acid, shaked well, and placed at room temperature for 30 min-1 h. The solution was put in the boiling water bath for 6-8 min, and then immediately put in −20° C. for rapid cooling for 30 min. Then 20 mL of chloroform-methanol (1:1, v/v) was added and mixed thoroughly, and the mixture was centrifuged at 4000 r/min for 10 min. The lower layer of chloroform was separated and the volume was measured. An equal volume of 0.15% sodium chloride was added, centrifuged at 4000 r/min for 10 min. The lower chloroform layer was collected and transferred to an erlenmeyer flask, dried at 70° C. for 2 hours, cooled and weighed to calculate the yield of microbial grease, which was for GC analysis.

3.4 Location-Specific Analysis of Nervonic Acid in Microbial Oil

The above acid-heat method was used to extract the total fat of the original strain and the engineered strain after fermentation and culture for 6 days. The lipase digestion method was used to detect the position of nervonic acid in TAG. The specific steps were as follows. 10 mg of oil and 10 mg of immobilized 1,3-position-specific lipase were added into 3 ml of methanol solution, and reacted at 30° C. for 8 h. Fatty acid methyl ester and 2-MAG were purified by TLC plate, and gas phase detection showed that nervonic acid was only present in the free fatty acid layer. That is, nervonic acid was located in the sn-1, 3 position of TAG (FIG. 4).

3.5 Determination of Nervonic Acid Percentage in Total Fatty Acid

After the microorganisms were weighed, 2.6 ml of methanol:sulfuric acid=98:2 solution was added to the glass tube and reacted at 85° C. for 3 h. After cooled in the refrigerator, it was added with 1 ml saturated NaCl and 1 ml n-hexane. After shaked, high-speed centrifugation (5000 rpm) was performed for 5 min. The supernatant was aspirated, filtered with an organic solvent filter membrane, and added to a gas chromatography vial.

The content of methyl nervonic acid was determined by GC method. Agilent7890B-GC instrument was used, wherein the chromatographic column used was HP-5 (30 m×0.32 mm×0.25 μm). Injection temperature: 250° C.; detector temperature: 250° C.; injection volume: 1 μL. Initial column temperature was 140° C., and kept for 1 min. Then it was increased to 180° C. at 10° C./min, and kept for 2 min. Then it was increased to 210° C. at 5° C./min, and kept for 4 min, and then it was increased to 250° C. at 5° C./min and kept for 4 min.

Under the above-mentioned heating conditions, the peak time of methyl nervonic acid detected by GC was 23.775 min (FIG. 5). Under shaking flask culture conditions, in strains YL1, YL2, YL2-1, YL2-2, YL2-3, YL2-4, YL3, YL4-1, YL4-2, YL4-3, YL4-4, YL4-5, YL4-6, YL6, YL7, YL8 and YL11, the percentages of nervonic acid contents in the total fatty acid content were 2.40%, 11.09%, 10.66%, 11.90%, 17.57%, 15.12%, 9.63%, 4.02%, 4.36%, 4.62%, 4.57%, 4.82%, 4.19%, 8.62%, 8.12%, 9.12% and 11.12% (FIG. 7). The $OD_{600}$ (YL2-3 taken as an example, as shown in FIG. 6), biomass and oil content of the strains cultured in batches of 17 strains had little difference. The biomass was about 20 g/L and the fat content was about 8.2 g/L. Under fermentation tank conditions, the maximum nervonic acid content of strain YL2-3 accounted for 30.6% of the total fatty acid content, and the maximum biomass was 82.6 g/L. The proportions of other fatty acids in the strain YL2-3 in fat were: C16:0 5.3%, C16:1 10.9%, C18:0 1.5%, C18:1 28.7%, C18:2 9.1%, and C24:0 2.8%.

3.6 Determination of Intracellular Aldehyde Levels

In order to verify the regulation of the redox balance, quantitative analysis of reactive aldehydes in the strains were performed as follows. po1g and YL2-4 cell pellets were collected by a refrigerated centrifuge and resuspended in PBS buffer. The yeast pellet was homogenized on a shaker, centrifuged at 4° C., and the supernatant was taken. Intracellular active aldehydes from the supernatant were measured according to the instructions described in Sigma's fluorescent aldehyde assay kit (MAK141-1KT). The results showed that compared with polg strain, the total lipid content of YL2-4 strain was increased by 2.5 times, and the amount of active aldehyde was significantly reduced. Wherein, the amount of active aldehyde in YL2-4 strain was about 4 times lower than that of polg strain at 50 h (FIG. 8).

Example 4. Nervonic Acid Fermentation

According to the above optimization results, the strain YL2-3 was amplified in a 500 L fermentor. The activated seed solution was inoculated at a 3% inoculum amount. The culture temperature was 28° C. The aeration rate was 5-8 L/min. The stirring speed was 300 r/min. And the fermentation pH (5.5) was adjusted with 3M NaOH solution. A total of 3 batches of fermentation were carried out, and it was found that the average biomass of strain YL2-3 was 126.56 g/L, the nervonic acid content accounted for 39.6% of the total fatty acid content, and the fat content was about 39.3 g/L. The proportions of other fatty acids in the total fatty acid content were: C16:0 4.3%, C16:1 7.9%, C18:0 3.5%, C18:1 25.7%, C18:2 4.9%, and C24:0 4.8% (FIG. 9).

All publications mentioned herein are incorporated by reference as if each individual document was cited as a reference in the present application. It should be understood that, after reading the above teachings of the present invention, those skilled in the art can make various modifications and changes. These equivalent forms are also within the scope defined by the claims appended hereto.

---

The invention claimed is:

1. A recombinant yeast strain overexpressing of at least one gene encoding fatty acid elongase wherein the fatty acid elongase is (i) cardamine mustard CgKCS gene, the nucleotide sequence of which is shown in SEQ ID NO: 96; and/or (ii) goat fatty acid elongase 6 gELOVL6 gene, the nucleotide sequence of which is shown in SEQ ID NO: 99;

and the recombinant yeast strain is a recombinant *Yarrowia* yeast strain which produces nervonic acid.

2. The recombinant yeast strain of claim 1, wherein the recombinant yeast strain overexpresses cardamine mustard CgKCS gene, the nucleotide sequence of which is shown in SEQ ID NO: 96; and the recombinant yeast strain further overexpresses goat fatty acid elongase 6 gELOVL6 gene, the nucleotide sequence of which is shown in SEQ ID NO: 99.

3. The recombinant yeast strain of claim 1, wherein the recombinant yeast strain overexpresses:

(a) a gene encoding a Δ9 desaturase;

(b) at least four genes encoding fatty acid elongases;

(c) a gene encoding a diglyceride acyltransferase;

(d) a gene encoding a fatty acid elongase targeting the endoplasmic reticulum;

(e) a gene encoding a diglyceride acyltransferase targeting the endoplasmic reticulum; and/or (f) a gene encoding a Δ9 desaturase targeting the endoplasmic reticulum.

4. The recombinant yeast strain of claim 3, wherein, the gene encoding a Δ9 desaturase is *Yarrowia lipolytica* SCD, the nucleotide sequence of which is shown in SEQ ID NO: 84;

the four genes encoding fatty acid elongases are respectively *Mortierella alpina* C16/18 elongase gene MaLCE1, the nucleotide sequence of which is shown in SEQ ID NO: 93;

arabidopsis AtFAE1 gene, the nucleotide sequence of which is shown in SEQ ID NO: 94;

African mustard BtFAE1 gene, the nucleotide sequence of which is shown in SEQ ID NO: 95;

cardamine mustard CgKCS gene, the nucleotide sequence of which is shown in SEQ ID NO: 96;

the gene encoding a diglyceride acyltransferase is *Yarrowia lipolytica* DGAT1 gene, the nucleotide sequence of which is shown in SEQ ID NO: 83;

the gene encoding a fatty acid elongase targeting the endoplasmic reticulum is cardamine mustard $CgKCS_{ER}$ gene with an encoding sequence for the signal peptide targeting the endoplasmic reticulum, the nucleotide sequence of which is shown in SEQ ID NO: 121;

the gene encoding a diglyceride acyltransferase targeting the endoplasmic reticulum is *Yarrowia lipolytica* $DGAT1_{ER}$ gene with an encoding sequence for the signal peptide targeting the endoplasmic reticulum, the nucleotide sequence of which is shown in SEQ ID NO: 122;

the gene encoding a Δ9 desaturase targeting the endoplasmic reticulum is *Yarrowia lipolytica* $SCD_{ER}$ gene with an encoding sequence for the signal peptide targeting the endoplasmic reticulum, the nucleotide sequence of which is shown in SEQ ID NO: 123.

5. The recombinant yeast strain of claim 3, wherein the recombinant yeast strain further overexpresses:

(a) two genes encoding fatty acid elongases targeting the endoplasmic reticulum; and/or (b) two genes encoding fatty acid elongases targeting the peroxisomes.

6. The recombinant yeast strain of claim 5, wherein, the two genes encoding fatty acid elongases targeting the endoplasmic reticulum are respectively cardamine mustard $CgKCS_{ER}$ gene with an encoding sequence for the signal peptide targeting the endoplasmic reticulum, the nucleotide sequence of which is shown in SEQ ID NO: 121; African mustard $BtFAE1_{ER}$ gene with an encoding sequence for the signal peptide targeting endoplasmic reticulum, the nucleotide sequence of which is shown in SEQ ID NO: 124;

the two genes encoding fatty acid elongases targeting peroxisomes are respectively cardamine mustard $CgKCS_{PTS}$ gene with an encoding sequence for the signal peptide targeting the peroxisomes, the nucleotide sequence of which is shown in SEQ ID NO: 125; African mustard $BtFAE1_{PTS}$ gene with an encoding sequence for the signal peptide targeting the peroxisomes, the nucleotide sequence of which is shown in SEQ ID NO: 126.

7. The recombinant yeast strain of claim 3, wherein the recombinant yeast strain further overexpresses:

(a) a gene encoding an aldehyde dehydrogenase;

(b) a gene encoding a glucose-6-phosphate dehydrogenase;

(c) a gene encoding a glutathione disulfide reductase; and/or (d) a gene encoding a glutathione peroxidase.

8. The recombinant yeast strain of claim 7, wherein, the gene encoding an aldehyde dehydrogenase is *E. coli* EcAldH gene, the nucleotide sequence of which is shown in SEQ ID NO: 105;

the gene encoding a glucose-6-phosphate dehydrogenase is *Saccharomyces cerevisiae* ScZwf gene, the nucleotide sequence of which is shown in SEQ ID NO: 106;

the gene encoding a glutathione disulfide reductase is *Yarrowia lipolytica* ylGSR gene, the nucleotide sequence of which is shown in SEQ ID NO: 91;

the gene encoding a glutathione peroxidase is *Yarrowia lipolytica* y1GPO gene, the nucleotide sequence of which is shown in SEQ ID NO: 92.

9. The recombinant yeast strain of claim 1, wherein the recombinant yeast strain overexpresses:

(a) a gene encoding a Δ9 desaturase;

(b) at least three genes encoding fatty acid elongases;

(c) a gene encoding a diglyceride acyltransferase; and/or (d) a gene encoding a phospholipase A2.

10. The recombinant yeast strain of claim 9, wherein, the gene encoding a Δ9 desaturase is *Yarrowia lipolytica* SCD gene, the nucleotide sequence of which is shown in SEQ ID NO: 84;

the three genes encoding fatty acid elongases are respectively arabidopsis AtFAE1 gene, the nucleotide sequence of which is shown in SEQ ID NO: 94; African mustard BtFAE1 gene, the nucleotide sequence of which is shown in SEQ ID NO: 95; cardamine mustard CgKCS gene, the nucleotide sequence of which is shown in SEQ ID NO: 96;

the gene encoding a diglyceride acyltransferase is *Yarrowia lipolytica* DGAT1, the nucleotide sequence of which is shown in SEQ ID NO: 83;

the gene encoding a phospholipase A2 is PLA2-1 gene, the nucleotide sequence of which is shown in SEQ ID NO: 85; or PLA2-2 gene, the nucleotide sequence of which is shown in SEQ ID NO: 86; or PLA2-3 gene, the nucleotide sequence of which is shown in SEQ ID NO: 87; or PLA2-4 gene, the nucleotide sequence of which is shown in SEQ ID NO: 88; or PLA2-5 gene, the nucleotide sequence of which is shown in SEQ ID NO: 89; or PLA2-6 gene, the nucleotide sequence of which is shown in SEQ ID NO: 90.

11. The recombinant yeast strain of claim 1, wherein the recombinant yeast strain overexpresses:

(a) a gene encoding a fatty acid elongase targeting the peroxisomes;

(b) a gene encoding a fatty acid elongase;

(c) a gene encoding a fatty acid elongase targeting the endoplasmic reticulum;

(d) a gene encoding a diglyceride acyltransferase targeting the endoplasmic reticulum; and/or (e) a gene encoding a Δ9 desaturase targeting the endoplasmic reticulum.

12. The recombinant yeast strain of claim 11, wherein, the gene encoding a fatty acid elongase targeting the peroxisomes is cardamine mustard $CgKCS_{PTS}$ gene with an encoding sequence for the signal peptide targeting the peroxisomes, the nucleotide sequence of which is shown in SEQ ID NO: 125;

the gene encoding a fatty acid elongase is the *Mortierella alpina* C16/18 elongase gene MaLCE1, the nucleotide sequence of which is shown in SEQ ID NO: 93;

the gene encoding a fatty acid elongase targeting the endoplasmic reticulum is cardamine mustard $CgKCS_{ER}$ gene with an encoding sequence for the signal peptide targeting the endoplasmic reticulum, the nucleotide sequence of which is shown in SEQ ID NO: 121;

the gene encoding a diglyceride acyltransferase targeting the endoplasmic reticulum is *Yarrowia lipolytica* $DGAT1_{ER}$ gene with an encoding sequence for the signal peptide targeting the endoplasmic reticulum, the nucleotide sequence of which is shown in SEQ ID NO: 122;

the gene encoding a Δ9 desaturase targeting the endoplasmic reticulum is the *Yarrowia lipolytica* $SCD_{ER}$ gene with an encoding sequence for the signal peptide targeting the endoplasmic reticulum, the nucleotide sequence of which is shown in SEQ ID NO: 123.

13. The recombinant yeast strain of claim 1, wherein the recombinant yeast strain overexpresses:

(a) a gene encoding a Δ9 desaturase;

(b) a gene encoding a fatty acid elongase;

(c) a gene encoding a fatty acid elongase targeting the endoplasmic reticulum; and/or (d) a gene encoding a fatty acid elongase targeting the mitochondria.

14. The recombinant yeast strain of claim 13, wherein, the gene encoding a Δ9 desaturase is *Mortierella alpina* Δ9 fatty acid desaturase MaOLE2 gene, the nucleotide sequence of which is shown in SEQ ID NO: 102;

the gene encoding a fatty acid elongase is goat fatty acid elongase 6 gELOVL6 gene, the nucleotide sequence of which is shown in SEQ ID NO: 99;

the gene encoding a fatty acid elongase targeting the endoplasmic reticulum is cardamine mustard $CgKCS_{ER}$ gene with an encoding sequence for the signal peptide targeting the endoplasmic reticulum, the nucleotide sequence of which is shown in SEQ ID NO: 121;

the gene encoding a fatty acid elongase targeting the mitochondria is cardamine mustard $CgKCS_{MTS}$ with an encoding sequence for the signal peptide targeting the mitochondria, the nucleotide sequence of which is shown in SEQ ID NO: 127.

15. The recombinant yeast strain of claim 1, wherein the recombinant yeast strain overexpresses:

(a) two genes encoding Δ9 desaturases;

(b) three genes encoding fatty acid elongases; and/or (c) a gene encoding a diglyceride acyltransferase.

16. The recombinant yeast strain of claim 15, wherein, the two genes encoding Δ9 desaturases are respectively *Yarrowia lipolytica* SCD gene, the nucleotide sequence of which is shown in SEQ ID NO: 84; arabidopsis AtADS1 gene, the nucleotide sequence of which is shown in SEQ ID NO: 103; or the two genes encoding Δ9 desaturases are respectively *Yarrowia lipolytica* SCD gene, the nucleotide sequence of which is shown in SEQ ID NO: 84; arabidopsis AtADS2 gene, the nucleotide sequence of which is shown in SEQ ID NO: 104;

the three genes encoding fatty acid elongases are arabidopsis AtFAE1 gene, the nucleotide sequence of which is shown in SEQ ID NO: 94; African mustard BtFAE1 gene, the nucleotide sequence of which is shown in SEQ ID NO: 95; cardamine mustard CgKCS gene, the nucleotide sequence of which is shown in SEQ ID NO: 96;

the gene encoding a diglyceride acyltransferase is *Yarrowia lipolytica* DGAT1 gene, as shown in SEQ ID NO: 83.

17. The recombinant yeast strain of claim 1, wherein the expression of peroxisome biogenesis factor 10 in the strain is down-regulated and the strain further overexpresses:

(a) a gene encoding a fatty acid elongase targeting the peroxisomes;

(b) a gene encoding a fatty acid elongase;

(c) a gene encoding a fatty acid elongase targeting the endoplasmic reticulum;

(d) a gene encoding a diglyceride acyltransferase targeting the endoplasmic reticulum; and/or (e) a gene encoding a Δ9 desaturase targeting the endoplasmic reticulum.

18. The recombinant yeast strain of claim 17, wherein, the down-regulated peroxisome biogenesis factor 10 is pex10 gene, the nucleotide sequence of which is shown in SEQ ID NO: 120;

the gene encoding a fatty acid elongase targeting the peroxisomes is cardamine mustard $CgKCS_{PTS}$ gene with an encoding sequence for the signal peptide targeting the peroxisomes, the nucleotide sequence of which is shown in SEQ ID NO: 125;

the gene encoding a fatty acid elongase is the *Mortierella alpina* C16/18 elongase gene MaLCE1, the nucleotide sequence of which is shown in SEQ ID NO: 93;

the gene encoding a fatty acid elongase targeting the endoplasmic reticulum is cardamine mustard $CgKCS_{ER}$ gene with an encoding sequence for the signal peptide targeting the endoplasmic reticulum, the nucleotide sequence of which is shown in SEQ ID NO: 121;

the gene encoding a diglyceride acyltransferase targeting the endoplasmic reticulum is *Yarrowia lipolytica* $DGAT1_{ER}$ gene with an encoding sequence for the signal peptide targeting the endoplasmic reticulum, the nucleotide sequence of which is shown in SEQ ID NO: 122;

the gene encoding a Δ9 desaturase targeting the endoplasmic reticulum is the *Yarrowia lipolytica* $SCD_{ER}$ gene with an encoding sequence for the signal peptide targeting the endoplasmic reticulum, the nucleotide sequence of which is shown in SEQ ID NO: 123.

19. The recombinant yeast strain of claim 1, wherein the yeast is *Yarrowia lipolytica.*

20. The recombinant yeast strain of claim 1, wherein the recombinant yeast strain overexpresses one or more exogenous fatty acid elongases wherein at least one of fatty acid elongases is goat fatty acid elongase 6 gELOVL6 gene, the nucleotide sequence of which is shown in SEQ ID NO: 99.

* * * * *